US010136955B2

(12) United States Patent
Tsekos et al.

(10) Patent No.: US 10,136,955 B2
(45) Date of Patent: Nov. 27, 2018

(54) ROBOTIC DEVICE FOR IMAGE-GUIDED SURGERY AND INTERVENTIONS

(71) Applicant: University of Houston System, Houston, TX (US)

(72) Inventors: Nikolaos V. Tsekos, Houston, TX (US); Michael Heffernan, Katy, TX (US)

(73) Assignee: University of Houston System, Houston, TX (US)

( * ) Notice: Subject to any disclaimer, the term of this patent is extended or adjusted under 35 U.S.C. 154(b) by 0 days.

(21) Appl. No.: 15/402,135

(22) Filed: Jan. 9, 2017

(65) Prior Publication Data
US 2017/0135772 A1    May 18, 2017

Related U.S. Application Data

(63) Continuation-in-part of application No. 14/010,155, filed on Aug. 26, 2013, now Pat. No. 9,539,058, and a continuation-in-part of application No. 14/011,574, filed on Aug. 27, 2013, now Pat. No. 9,855,103.

(60) Provisional application No. 61/692,943, filed on Aug. 24, 2012, provisional application No. 61/693,534, filed on Aug. 27, 2012.

(51) Int. Cl.
*B25J 3/00* (2006.01)
*A61B 34/30* (2016.01)
*B25J 9/10* (2006.01)
*B25J 9/14* (2006.01)

(52) U.S. Cl.
CPC ............. *A61B 34/30* (2016.02); *B25J 9/102* (2013.01); *B25J 9/106* (2013.01); *B25J 9/144* (2013.01)

(58) Field of Classification Search
CPC .... B25J 3/04; B25J 3/00; B25J 9/1689; A61B 19/2203; A61B 2019/2223; A61B 2019/262; A61B 2019/5227; A61B 2019/5229; A61B 2019/5297; A61B 2090/374; A61B 2090/378; A61B 90/39
See application file for complete search history.

(56) References Cited

U.S. PATENT DOCUMENTS

| | | | | |
|---|---|---|---|---|
| 6,167,292 | A * | 12/2000 | Badano | A61B 90/39 600/407 |
| 2003/0233039 | A1* | 12/2003 | Shao | G06T 7/20 600/407 |
| 2004/0009459 | A1* | 1/2004 | Anderson | G06F 19/3481 434/262 |

(Continued)

FOREIGN PATENT DOCUMENTS

WO    WO 2007005367 A2 *    1/2007    ............. A61B 34/75

*Primary Examiner* — Elmer Chao
(74) *Attorney, Agent, or Firm* — Eric P. Mirabel

(57) ABSTRACT

Provided herein are actuation transmission lines used for robotic systems, for example, MRI guided robots, for image-guided robot-assisted surgical and medical intervention procedures. This actuation transmission lines may include any of the following: one or more sections of a flexible channel; one or more sections of a rigid channel in a connecting relationship with the one or more sections of a flexible channel; solid media disposed inside the channel; one or more mechanical links in contact with the solid media inside the channel electronically or mechanically linked to a power source; a fine-tuning module disposed in the flexible channel; and one or more media motion sensors.

19 Claims, 104 Drawing Sheets

(56) References Cited

U.S. PATENT DOCUMENTS

| | | | |
|---|---|---|---|
| 2007/0156122 A1* | 7/2007 | Cooper | B25J 19/0016 606/1 |
| 2008/0004632 A1* | 1/2008 | Sutherland | A61B 34/75 606/130 |
| 2008/0287783 A1* | 11/2008 | Anderson | A61B 6/12 600/429 |
| 2008/0287963 A1* | 11/2008 | Rogers | A61B 1/00039 606/130 |
| 2009/0112082 A1* | 4/2009 | Piferi | A61B 5/055 600/411 |
| 2011/0077504 A1* | 3/2011 | Fischer | A61B 34/30 600/411 |
| 2011/0107270 A1* | 5/2011 | Wang | G06F 19/3481 715/850 |

* cited by examiner

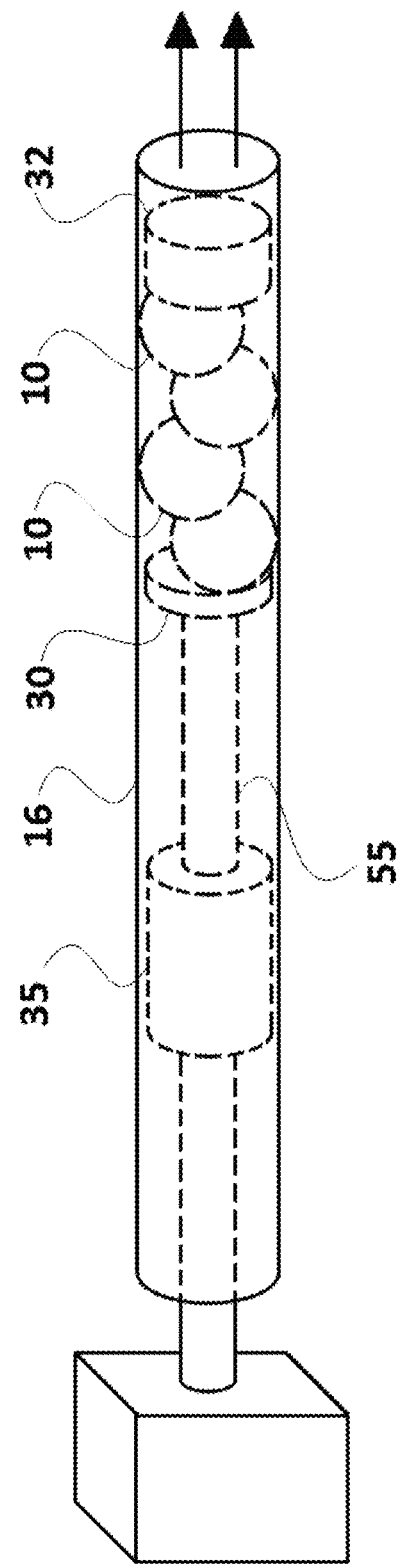

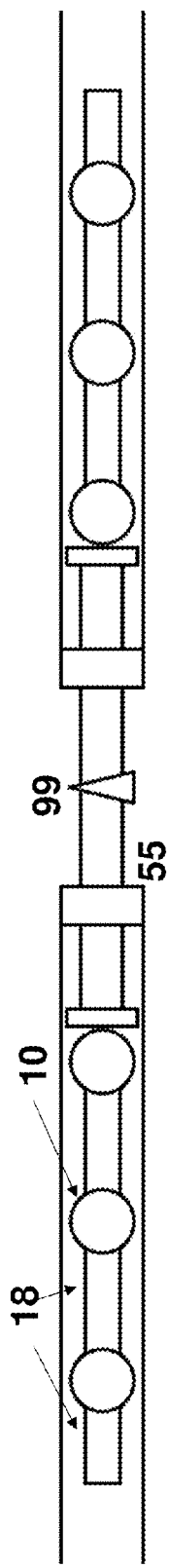

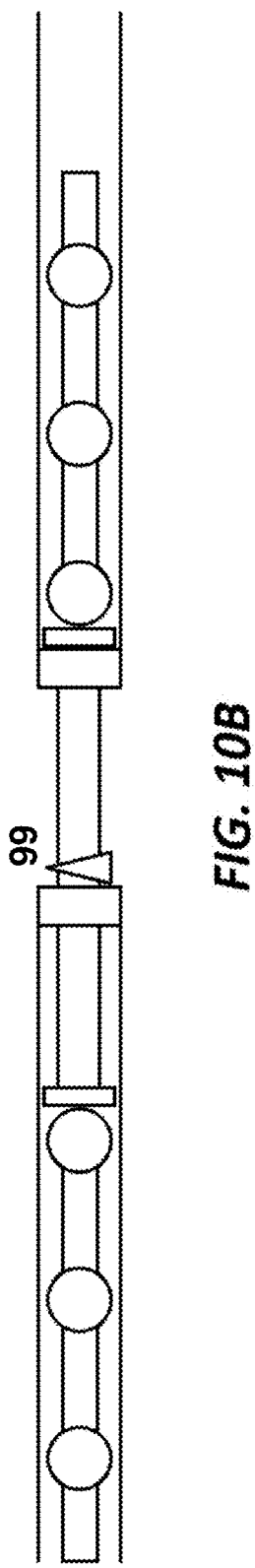

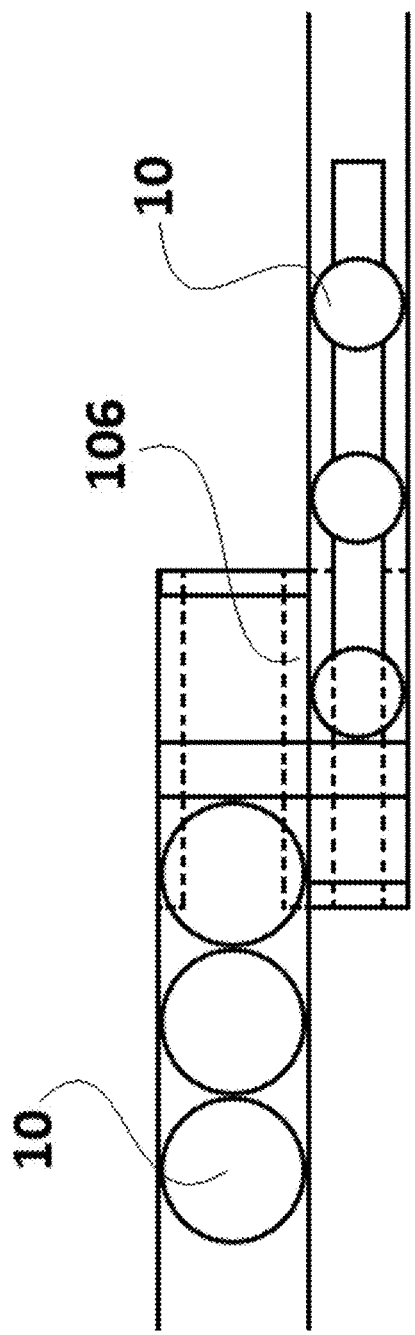

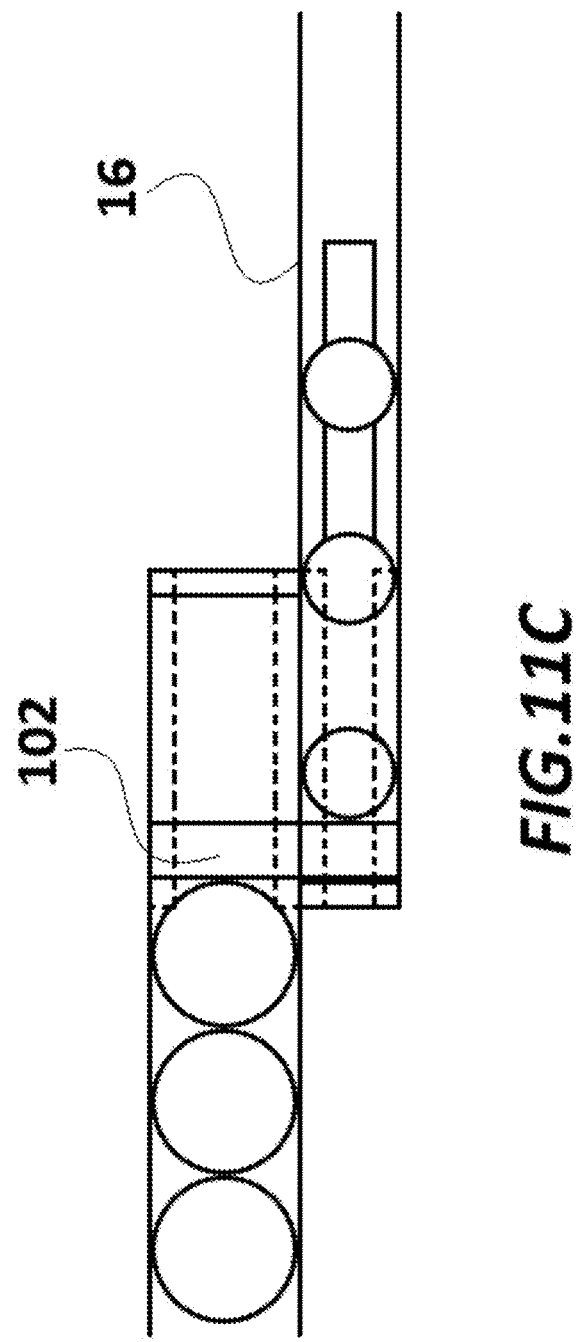

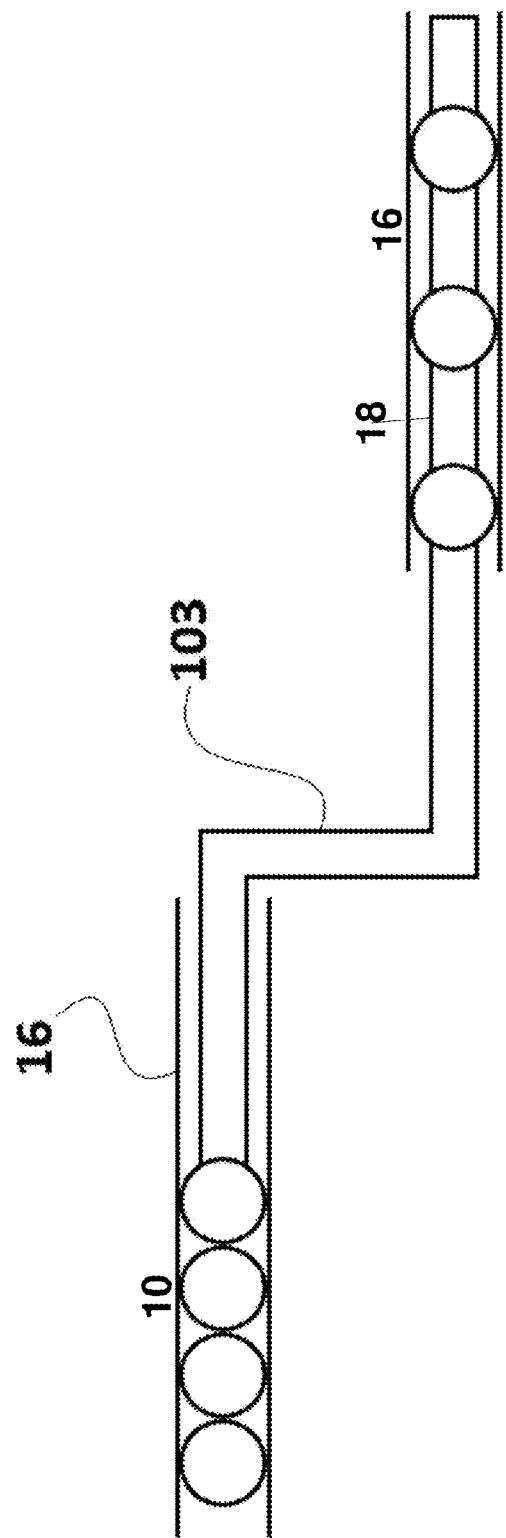

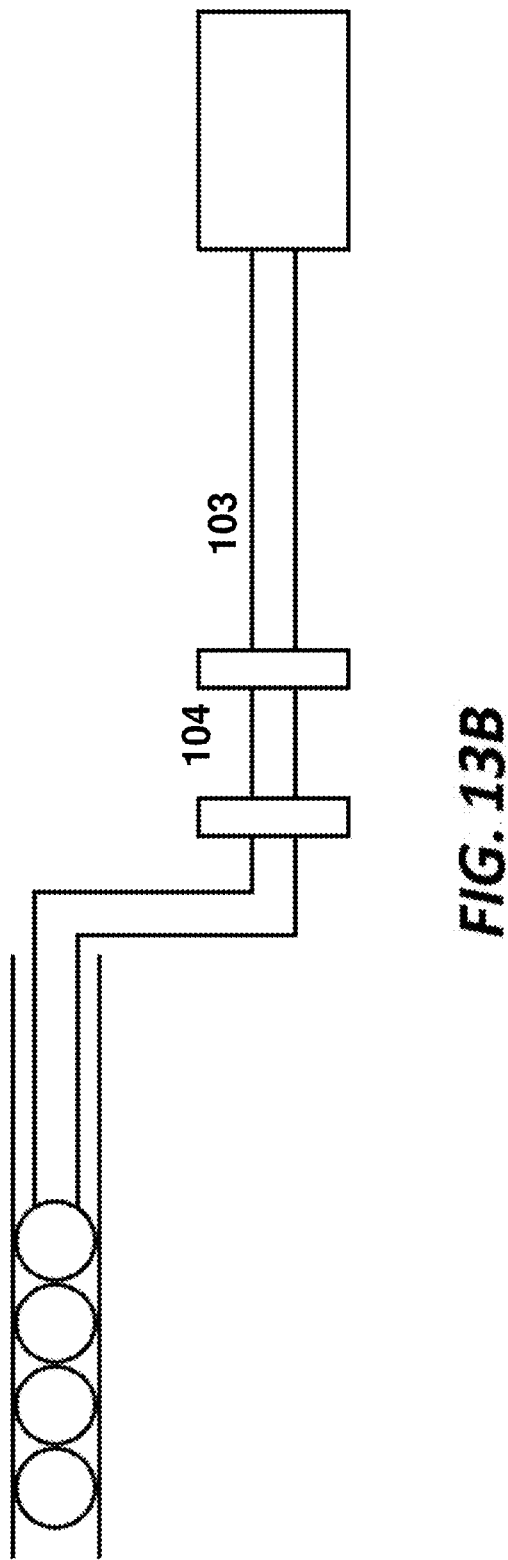

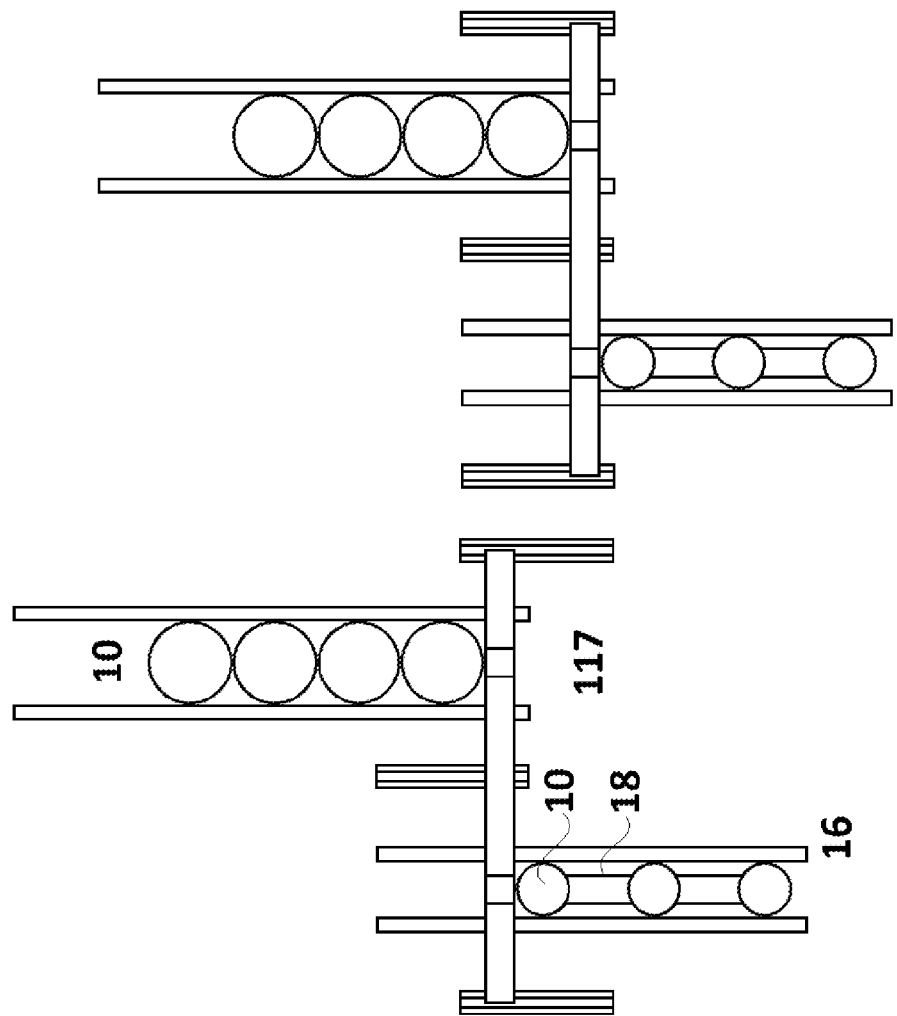

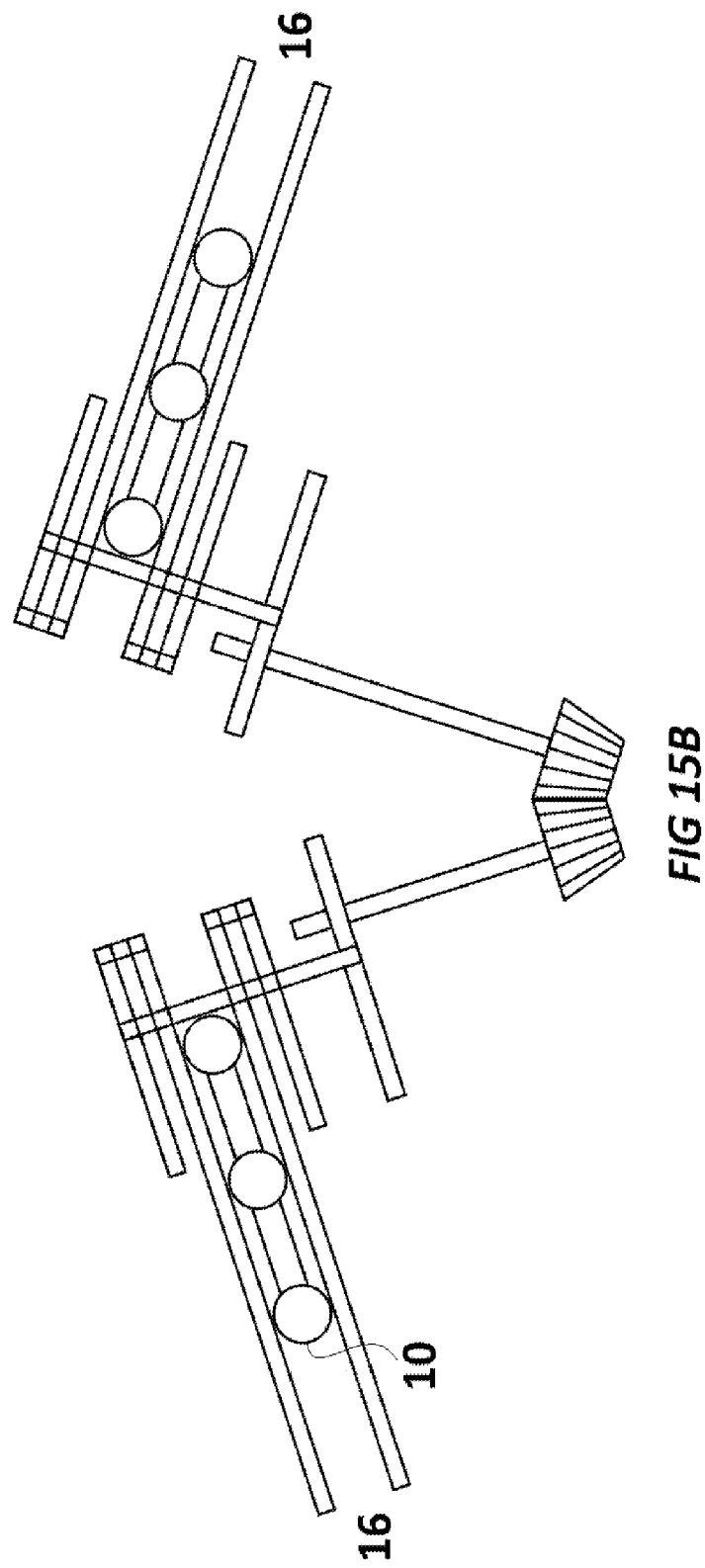

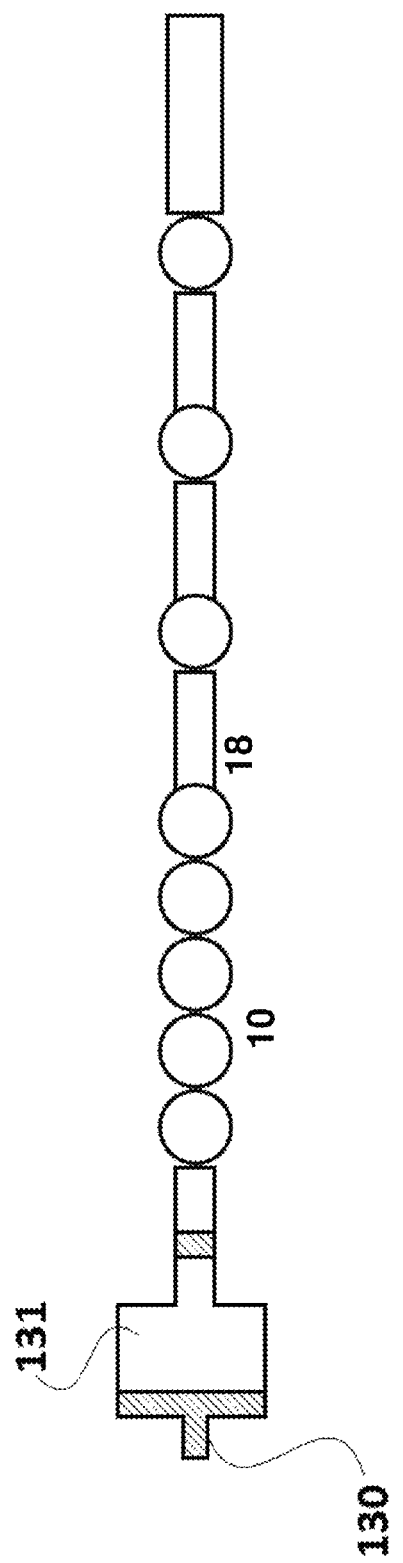

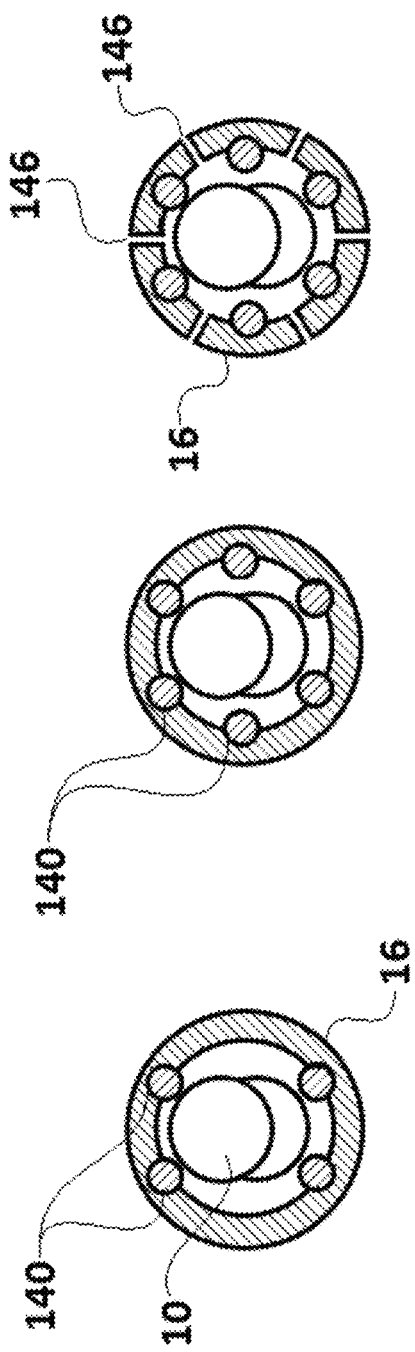

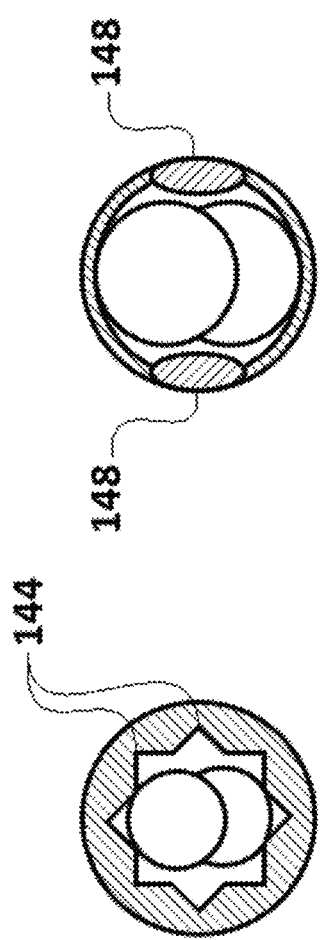

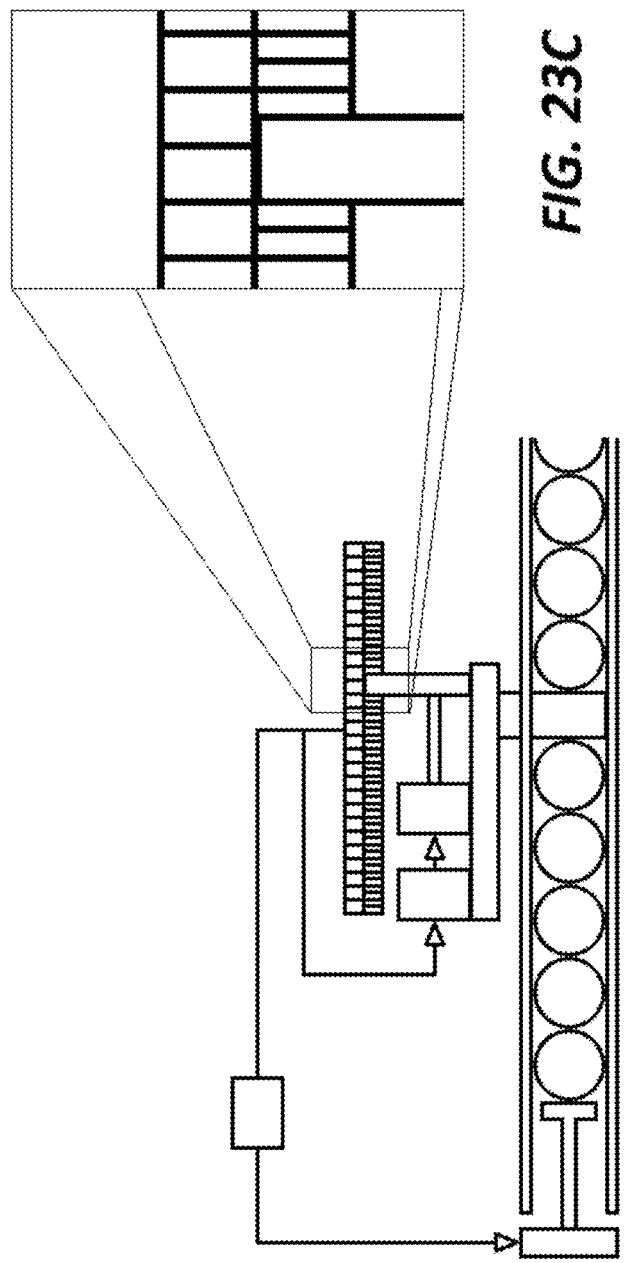

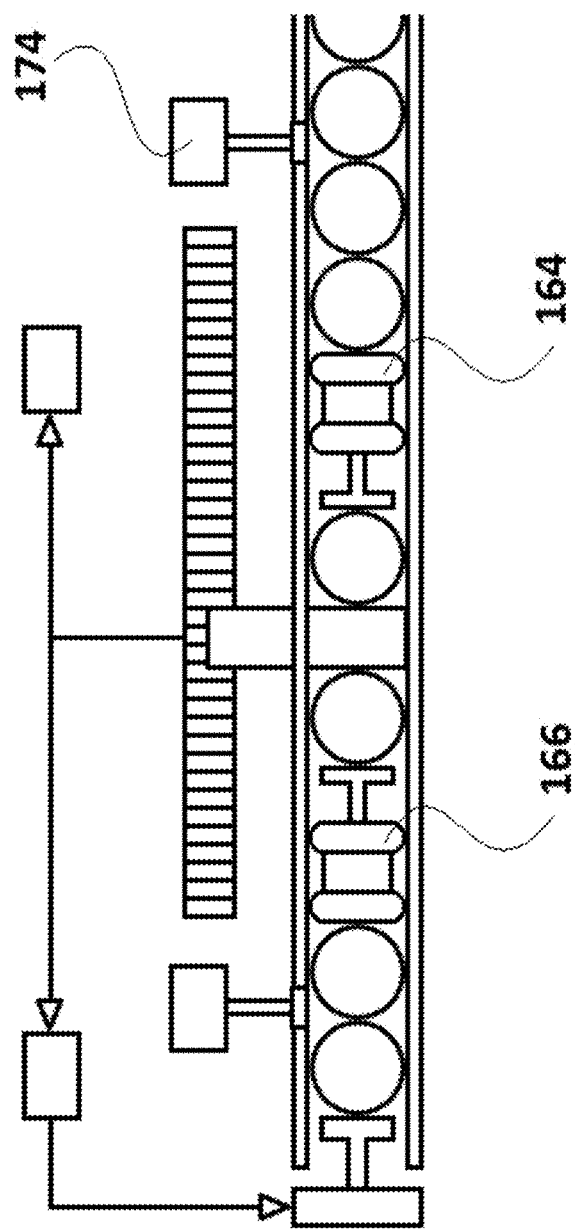

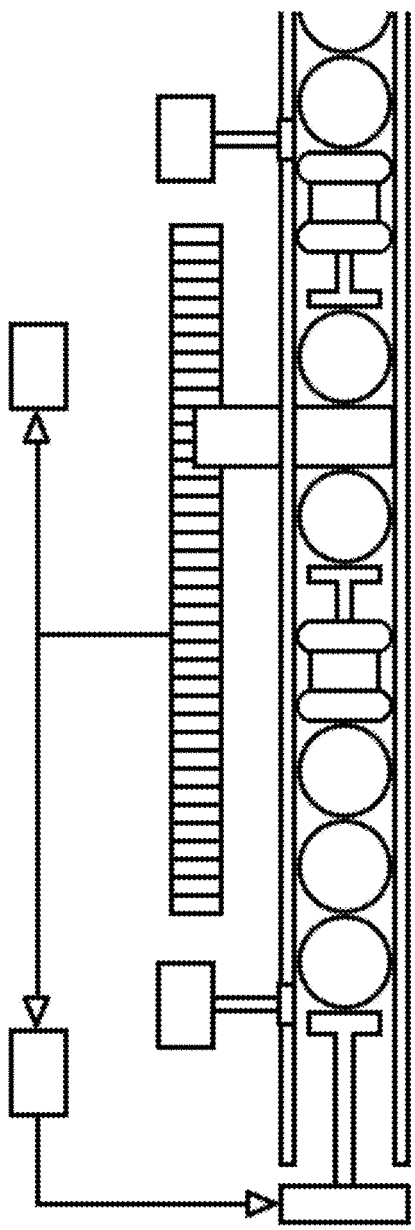

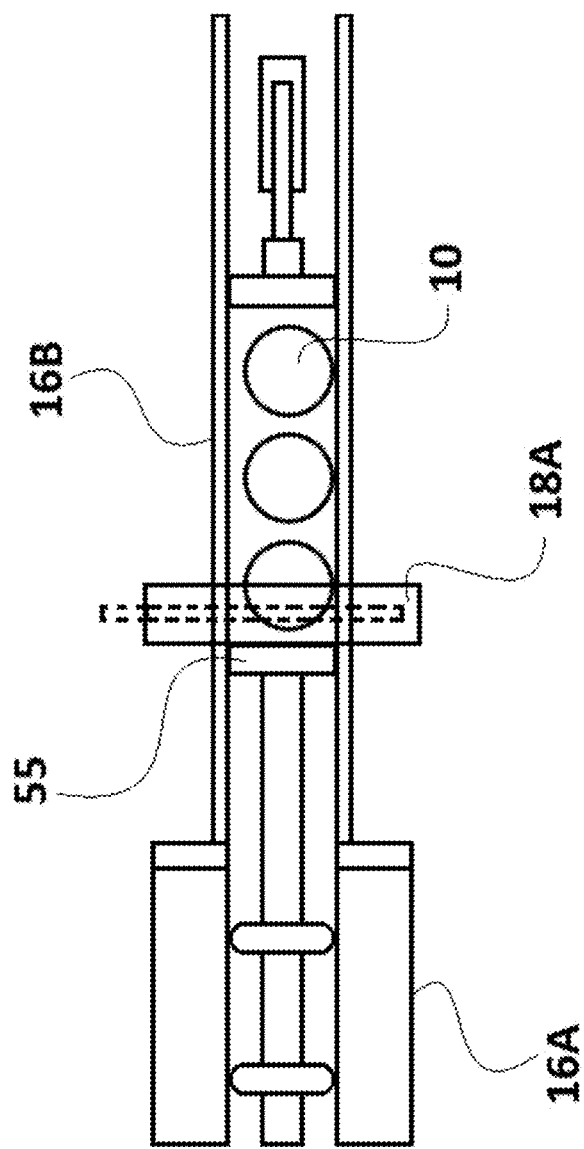

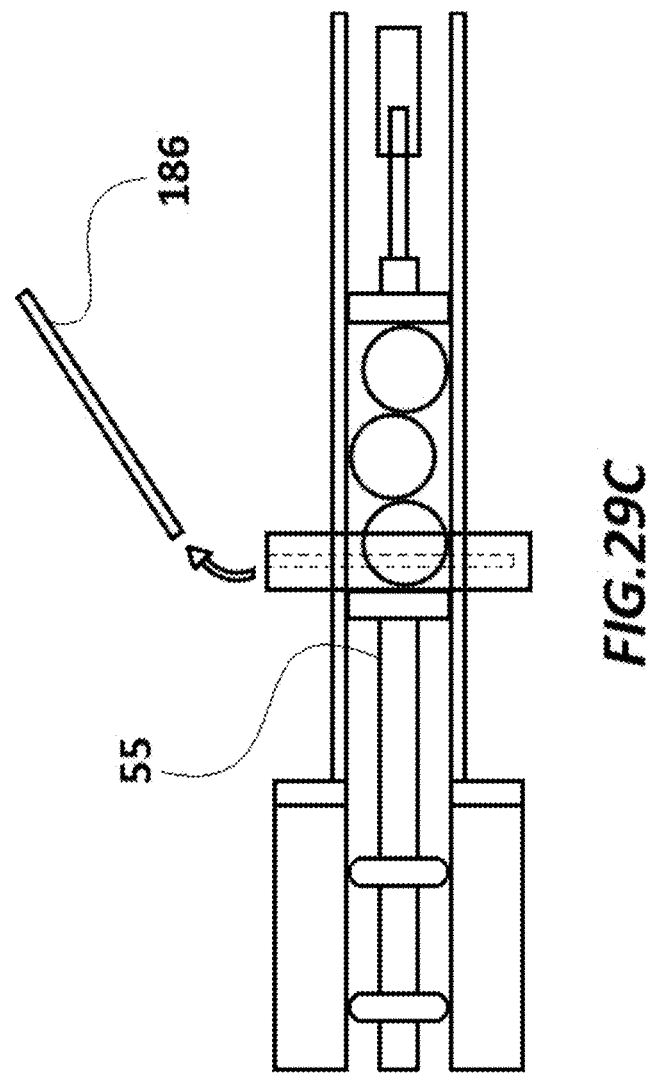

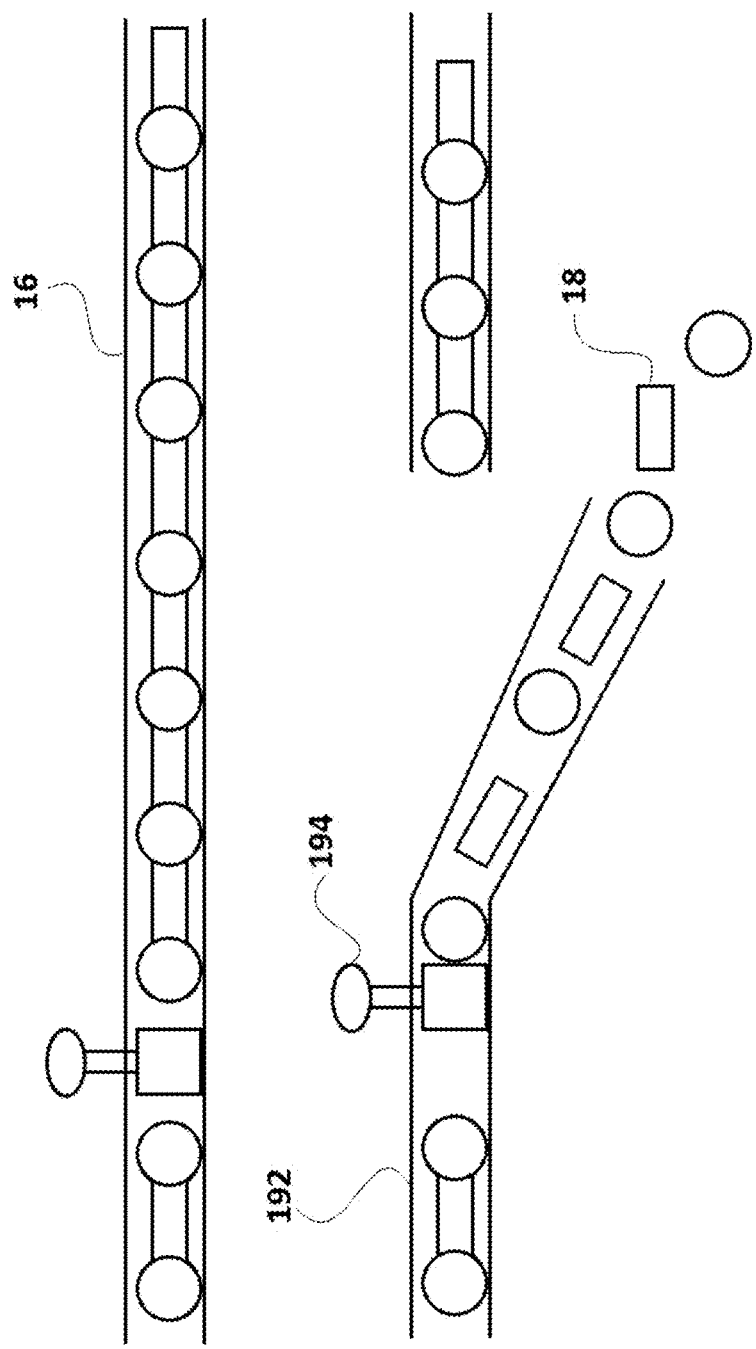

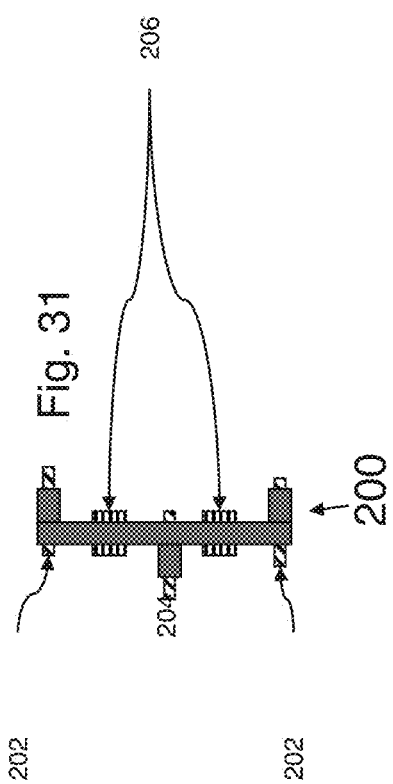

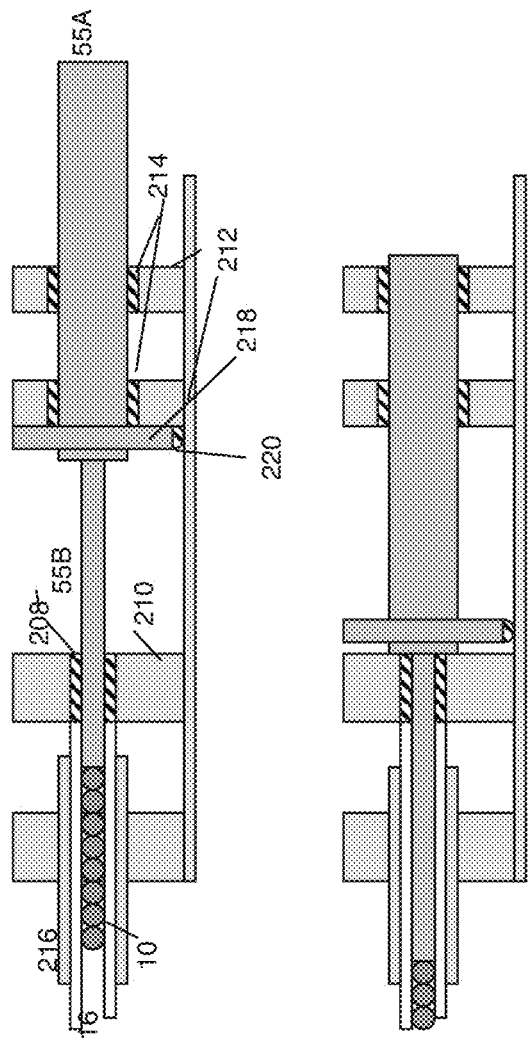

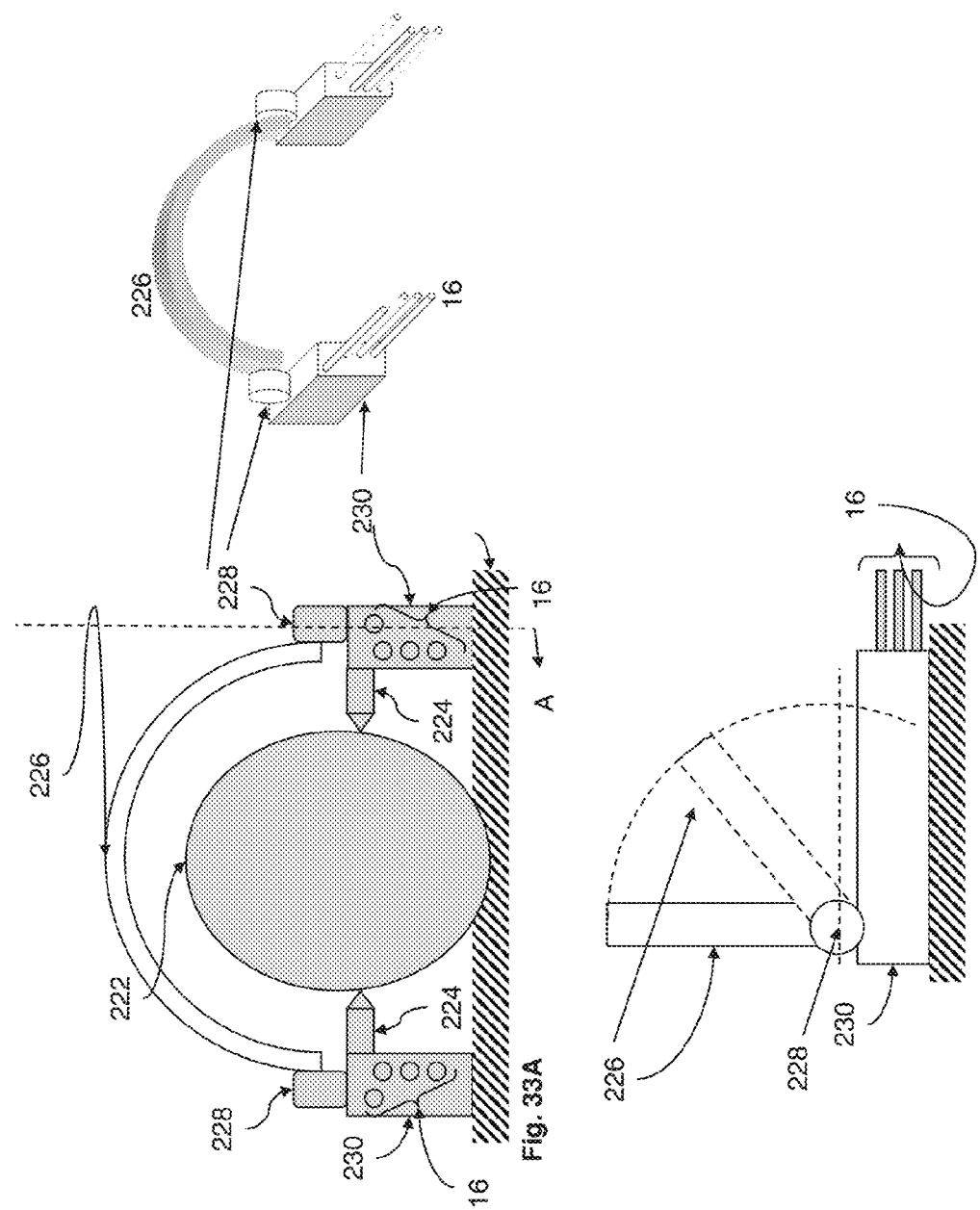

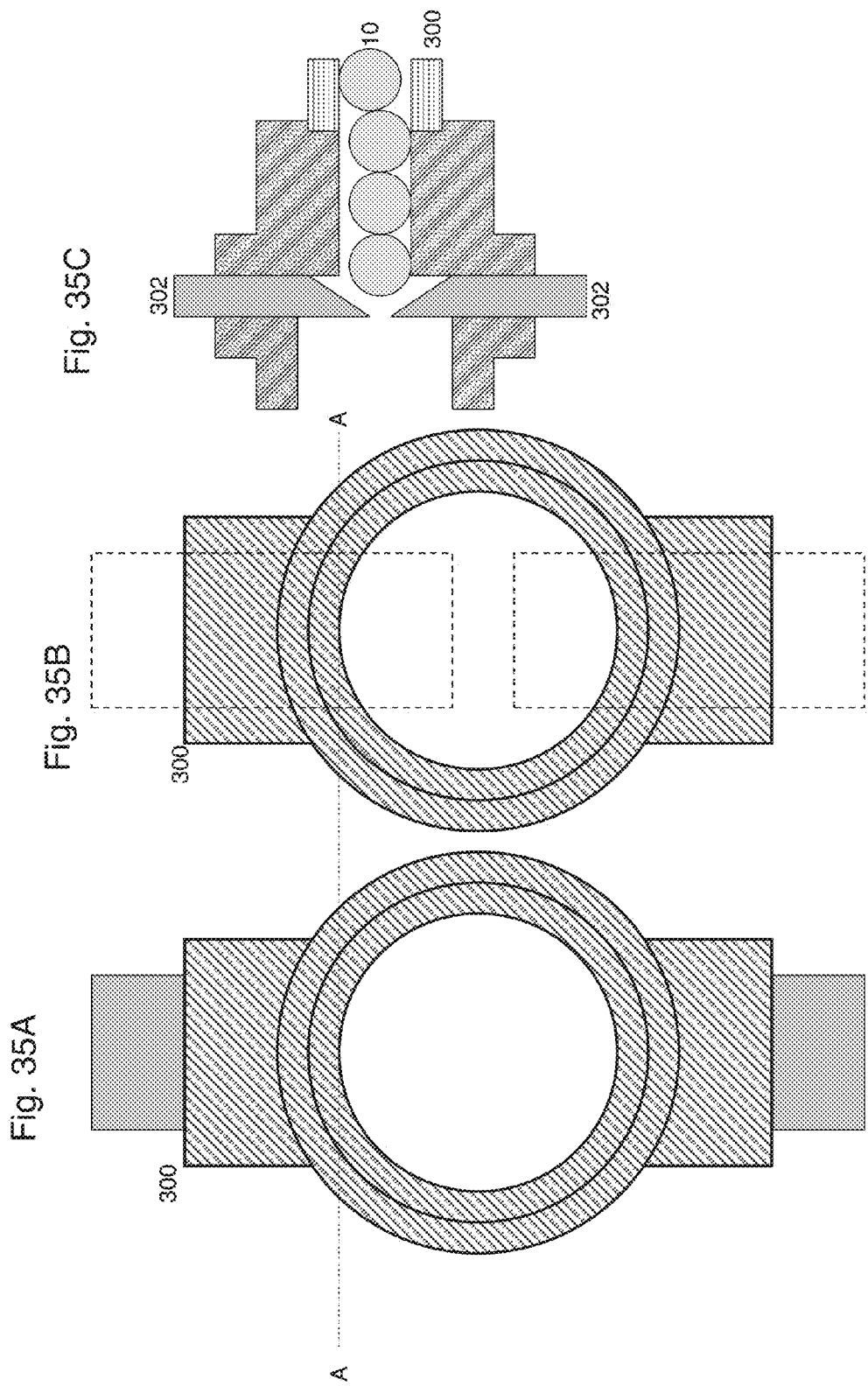

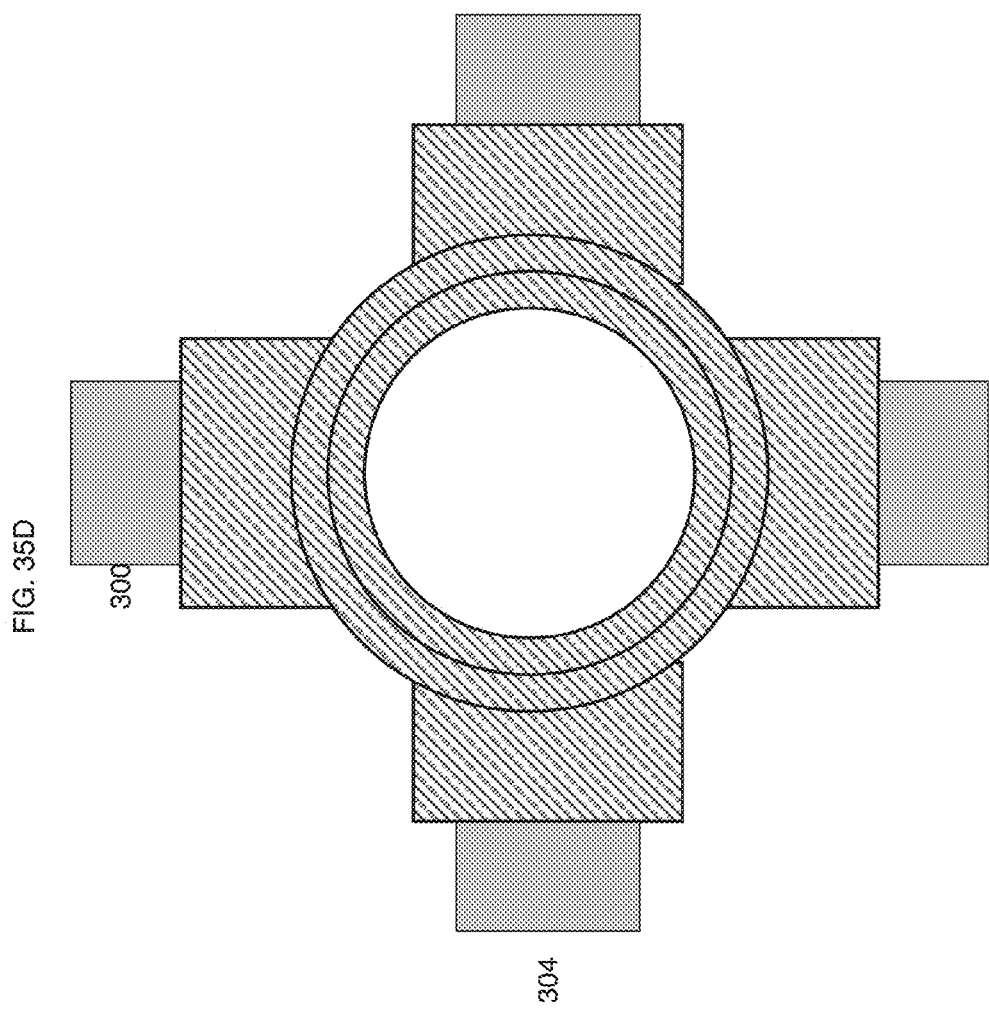

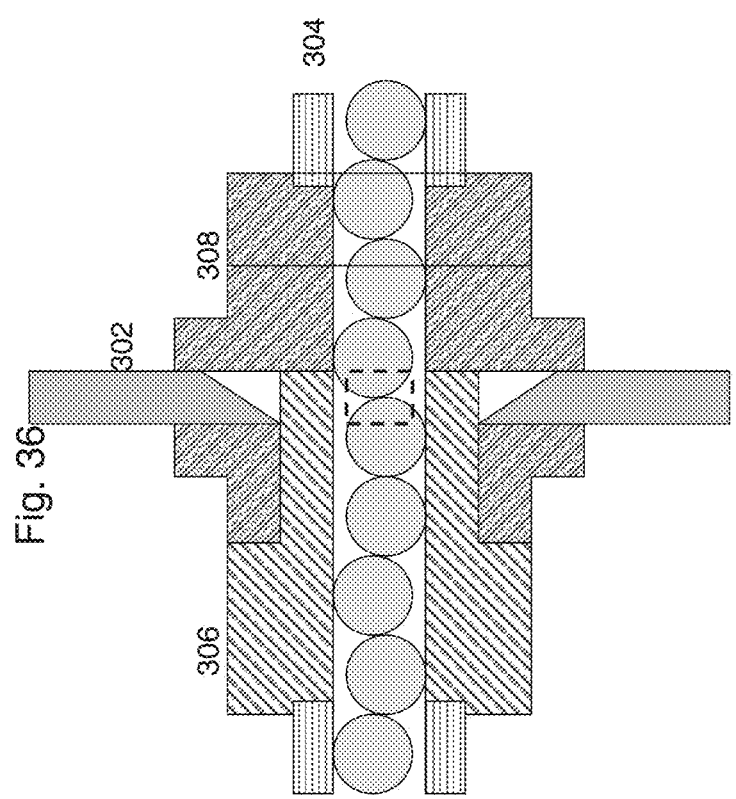

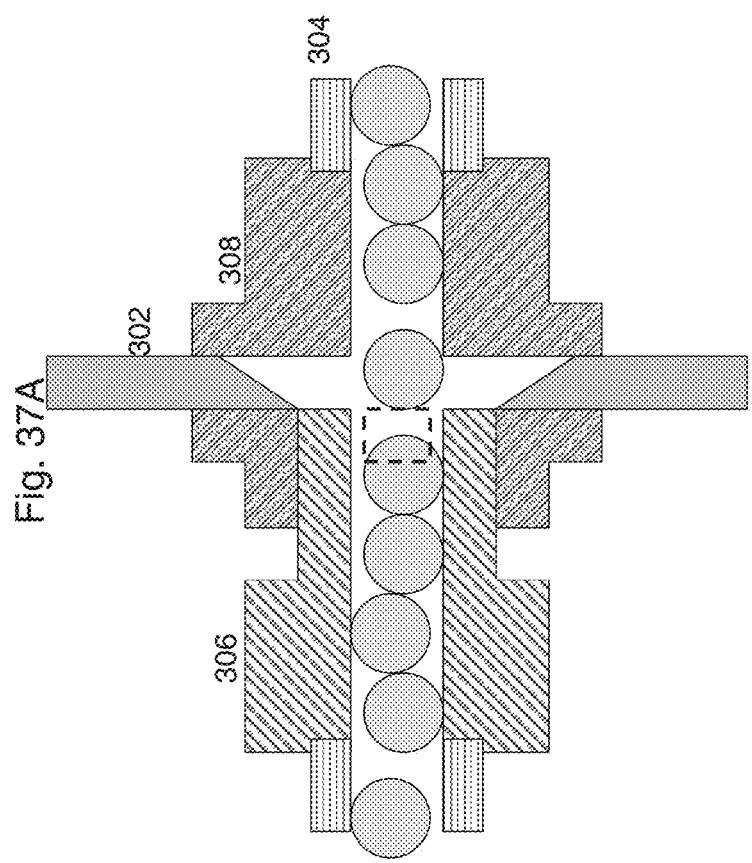

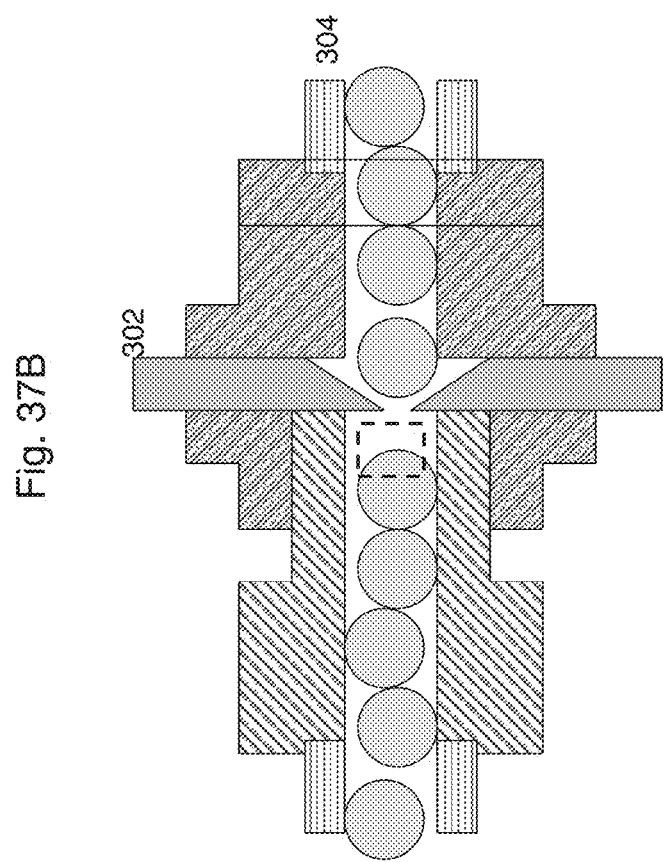

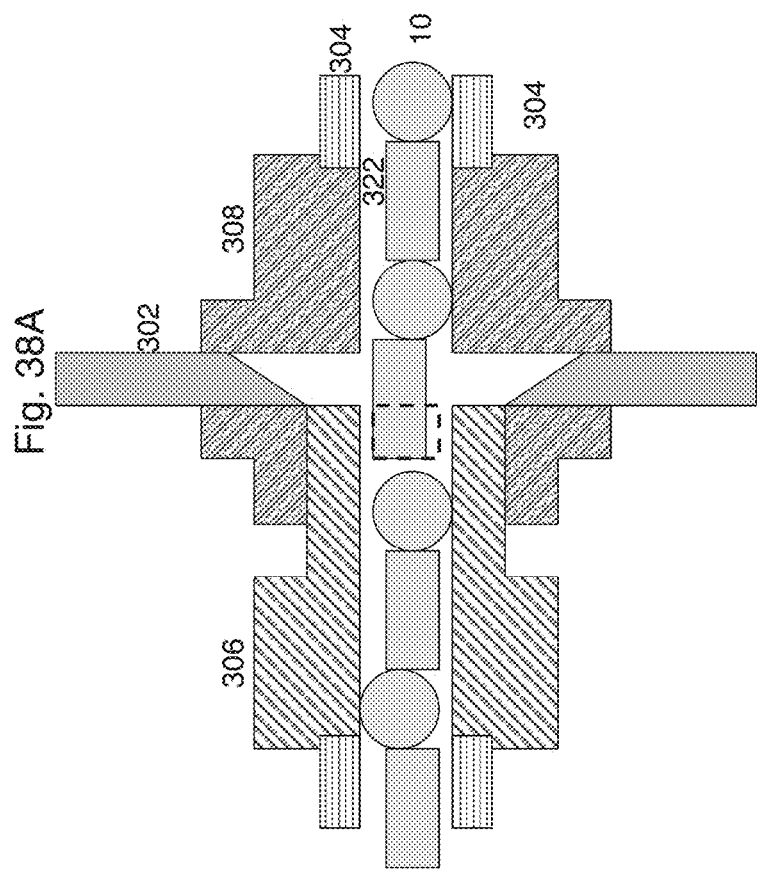

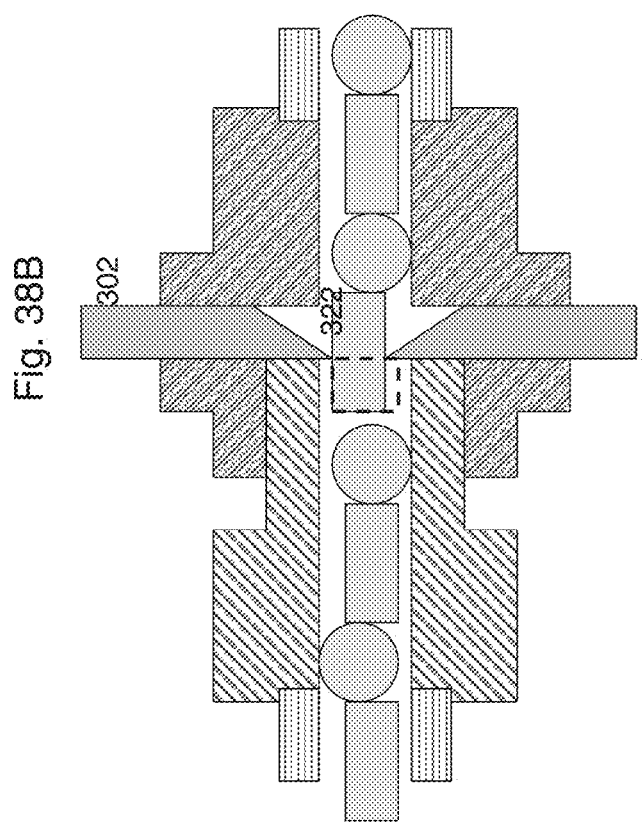

ROBOTIC DEVICE FOR IMAGE-GUIDED SURGERY AND INTERVENTIONS

CROSS-REFERENCE TO RELATED APPLICATIONS

This is a continuation-in-part patent application of pending nonprovisional patent applications U.S. Ser. No. 14/010,155, filed Aug. 26, 2013, and U.S. Ser. No. 14/011,574, filed Aug. 27, 2013.

FEDERAL FUNDING LEGEND

This invention was made with governmental support under Grant Numbers CNS-0932272 and STTR-1622946 awarded by the National Science Foundation. The government has certain rights in the invention.

FIELD OF THE INVENTION

The present invention relates to the fields of robotics and robot assisted medical interventions and surgical procedures.

BACKGROUND

Robotic assistance in minimally invasive procedures, including Single Port Access ("SPA") surgeries and percutaneous interventions, is emerging as a more patient-friendly, practice-enhancing and, eventually, cost-effective alternative to traditional open surgeries or free-hand interventions. Such a paradigm shift requires robust, scalable and efficient methodology for integrating multimodal sensing, e.g., tissue and molecular level imaging, controlled systems such as robots and haptic devices, and, the surgeon. Several factors may contribute to viable systems, including the seamless integration of real-time image guidance that can locally assess the tissue pathology and function, with operator interfacing allowing precise control of movement of surgical instruments.

Real-Time Image Guidance RTIG offers unique features for assessing the Area of Procedure (AoP), including assessing real-time tissue deformation and motion, secondary to the procedure or natural motion, related to, e.g. breathing or heartbeat; monitoring the tools in 3D; and updating the pathophysiology information of the targeted tissue. Real-Time Image Guidance may facilitate a methodological leap from current approaches of "keyhole" visualization, i.e. endoscopy or laparoscopy, and pre-operative imaging guidance, to a more global and informational-rich perception of the AoP, which can enable more complex surgeries, and better outcomes with conventional surgeries. Extensive groundbreaking work has been performed with different imaging modalities, including ultrasound ("US"), and magnetic resonance imaging ("MRI"), for both free-hand and robot-assisted procedures.

Another problem which must be addressed for robot-assisted procedures is how to guide the surgical instrument precisely to the desired location by an appropriate route. Where MRI is used as the imaging system for real time position monitoring, the surgery must be carried out in the space constraints of an MRI scanner, and must be operable in a large magnetic field. These issues are addressed by the systems of the present invention.

SUMMARY

The invention relates to controlling movement of surgical instruments, where the instruments are moved by objects forced along a channel, hereinafter referred to as an actuation transmission line. The actuation transmission line is preferably flexible (so the system can bend to be accommodated in confined spaces) with solid media disposed inside. The line can be sectioned so as to bend and accommodate the contours of the patient or the operational space (e.g., inside an MRI chamber and/or around a patient's body).

Movement of the solid media is preferably driven by a piston or other attachment linked to a power source, either extending axially into the channel or otherwise engaging one or more of the solid media inside the channel. Preferably, there are additional movement-controlling mechanisms (which may, for example, be electronically linked to a fine tuning module) to exert added fine control over the media movement.

Pistons, or other types of attachments, can be used to mechanically connect channels which are not axially aligned. Force enhancement mechanisms (e.g., hydraulics or gearing or blocking/unblocking of channel sections) may also be included to enhance fine control of the movement of the media and of the surgical instrument. Inserts in the lumen of the channel can assist in maintaining the aligned position of the media. A mechanism to allow changing the movement direction of the media can also be included. It is also preferable to have a solid media release mechanism, such that the media can be removed from the actuation line, and the surgical instrument can then be manually moved (or its further motion arrested).

The flexible channel can also include rigid sections, and preferably also includes media motion position, velocity or acceleration detectors, which feed back encoded information to allow enhanced control of the movement actuators.

Other and further aspects, features and advantages of the present invention will be apparent from the drawings and detailed description which follows, and from the published parent applications, US Publ'n Nos. 20140058407 and 20140058406.

BRIEF DESCRIPTION OF THE DRAWINGS

So that the matter in which the above-recited features, advantages and objects of the invention, as well as others which will become clear are attained and can be understood in detail, more particular descriptions and certain embodiments of the invention briefly summarized above are illustrated in the appended drawings. However, the drawings illustrate preferred embodiments are not to be considered as limiting the invention scope.

FIG. 1A is an axial sectional view illustrating that pressure from the ends can cause spheres to move out of axial alignment. FIG. 1B shows a sectional view of line 16 taken along lines A-A'. FIG. 1C is an axial sectional view of a line filled with spacers between the spheres. FIG. 1D shows an axial sectional view of the line packed with oblong-shaped solid media. FIG. 1E shows an axial sectional view of a line packed with mating oblong-shaped media.

FIGS. 3A-3C illustrate the use of a piston loader that is substantially located inside the lumen of the channel for packing media into the lumen. FIG. 3A shows an initial loader position with respect to the solid media, where it is unpacked. FIG. 3B illustrates that extending the piston closes the gaps between the media by forcing the media against a media blocker. FIG. 3C shows that the packed solid media is able to drive the media blocker along the lumen.

FIG. 4A shows an initial position of the loader with respect to the solid media, where it is unpacked. FIG. 4B illustrates that moving the loader to the right closes the gaps between the media by forcing the media against a media blocker. FIG. 4C shows the continuous and packed solid media is able to drive the media blocker.

FIG. 5A shows an initial position of both loader motors, where the actuation motor moves along a path/rail. FIG. 5B demonstrates that moving the actuation motor closes the gaps between the solid media. FIG. 5C shows that the secondary motor can further drive the solid media after the movement of the actuation motor reaches a limit.

FIG. 9A shows the initial position of the size converter piston. FIG. 9B shows the actuation line in the process of transmitting the actuation force from the smaller sized solid media to the larger sized solid media. FIG. 9C shows the end position of the piston fully pushed toward the larger sized solid media.

FIGS. 10A-10C depicts two sections of a transmission line connected by a two-headed piston, which is moved by attaching its central portion to a power source. FIG. 10A demonstrates an initial position for the. FIG. 10B shows the piston is in the process of pushing the solid media toward left. FIG. 10C shows the piston is in the process of pushing the solid media toward right.

FIGS. 11A-11C show the implementation of an alternative type of line size converter with the input and output line overlapping at the section of a reciprocating mechanical link. FIG. 11A shows the initial position of the solid media and the size converter mechanical link. FIG. 11B shows the process of the actuation transmission from smaller sized line to larger sized line. FIG. 11C depicts the mechanical link travels the full range of the opening slots on the lines, until it reaches the end of the smaller line.

FIGS. 12A-12B demonstrate the use of a mechanical link formed by two pistons linked together with their respective axes offset. FIG. 12A shows the initial position of two sections of an actuation line offset like the pistons of the link. FIG. 12B shows the final position of mechanical link and solid media when the actuation is transmitted from the higher line to the lower line.

FIG. 13B shows two actuation lines of FIG. 13A, in a final position.

FIGS. 14A-14C show that that members driving spheres in lines can be guided on external rails. FIG. 14A is a partially ghosted elevational view and FIG. 14B is an un-ghosted elevational view. FIG. 14C is a plan view of a similar but different arrangement of rails and lines.

FIGS. 15B and 15C show cross-sectional views of a mechanical link that is two angled gears, to enable two independent lines with offset and/or non-parallel axes to be mechanically linked.

FIG. 16A depicts the initial positions for the solid media in the transmission lines. FIG. 16B the end position of the solid media and the pistons when the single line is used to actuate multiple lines.

FIGS. 18A-18B depict units in the solid media transmission line which used to amplify the transmitted force. FIG. 18A illustrates a self-contained hydraulic fluidic pressure amplifier FIG. 18B illustrates using gears to move pistons in opposite directions, where use of different gear ratios (a smaller diameter gear) can be used to amplify force.

FIGS. 19A-19F are sectional views depicting structures of the internal surface of the line to interact with the media. FIG. 19A shows a cross section of a line with four cylindrical bars embedded therein. FIG. 19B shows a cross section of a line with six cylindrical bars embedded therein. FIG. 19C shows a cross section of a line with six cylindrical bars and a multitude of openings for equilibrating the pressure inside and outside the tube. FIG. 19D shows a line with internal longitudinal inserts. FIG. 19E shows a cross section of a line with two structures embedded along the inside of the lumen where the structures include channels for housing material or wiring. FIG. 19F shows a cross section of a tube with one longitudinal opening.

FIG. 20B is a cross section of the device in FIG. 20A taken along the lines B-B.

FIG. 21B shows a cross section taken along the lines B-B of FIG. 21A. FIG. 21D shows an cross section taken along the lines A-A. FIG. 21C is a cross section of a related arrangement for linking two solid media channels like those in FIG. 21A. FIGS. 21E and 21F show the operation of the double channel mechanism of FIGS. 21A to 21D using pistons, where FIG. 21E shows a starting position, and FIG. 21F shows the media of the lower line translated to the left, which moves the media of the upper line to the left as well. FIG. 21G shows a similar arrangement to FIGS. 21A to 21F, except that the upper channel is open. FIG. 21H is a sectional view taken along lines A-A of FIG. 21G. FIGS. 21I and 21J are similar to FIGS. 21A to 21F, except that the channels are side by side, not one on top of the other.

FIG. 23B illustrates a similar arrangement to FIG. 23A to allow fine tuning control of the movement of media in the line. FIG. 23C illustrates a related arrangement for interlocking teeth on mating members to aid in fine movement control.

FIG. 25A depicts a similar arrangement to FIGS. 22A-23C, but with a wireless power source. FIG. 25B depicts the mechanism of FIG. 25A in a different position.

FIG. 27A shows a long axis cross-sectional view of the media and a blocker unit. FIG. 27B shows a cross section of the connector and the blocking unit. FIG. 27C shows a cross section of the connector and an alternative blocking unit that enters into a slot in the body of the connector. FIG. 27D shows an exploded view of a locking mechanism for lines and shows the two lines attached through the locking mechanism in FIG. 27E.

FIGS. 29A to 29C illustrates the connection of two sections of lines in three steps, where the blockers are removed in the final step. FIG. 29A illustrates the two sections un-connected. FIG. 29B illustrates the two sections connected. FIG. 29C illustrates the two sections connected and the blocker removed.

FIGS. 30A-30G illustrates the operation of a safety or emergency release mechanisms for releasing the solid media in the line. FIG. 30B is a sectional view along the plane A-A of FIG. 30A. FIG. 30D is a sectional view along the plane B-B of FIG. 30C. FIGS. 30E and 30F depict alternative release mechanisms. FIG. 30G illustrates use of a spring to move media in the line before or after release.

FIG. 31 illustrates multichannel lines comprising one input channel, two output channels, pistons and a set of loader screws for advancing media in the lines.

FIGS. 32A and 32B illustrate a system for guiding a piston as it moves in a line, in a two-piston, two-line system. FIG. 32A shows a starting position and FIG. 32B shows the final position of the mechanism.

FIGS. 33A and 33B illustrate a system for guiding an instrument in a defined path around a patient. FIG. 33A is an elevational view of the mechanism, and FIG. 33B is a sectional view along the lines A-A.

FIG. 34A shows a mechanism with an angled face. FIG. 34B shows the mechanism of FIG. 34A attached to a guide mechanism. FIG. 34C shows a similar mechanism to FIG. 34A.

FIGS. 35 to 35D illustrate a system of line connectors and line blockers, which can be selectively actuated. FIG. 35A is an elevational view of a connector. FIG. 35B is an elevational view of a connector with a blocker in place. FIG. 35C is an sectional view of a connector with a blocker in place. FIG. 35D is an elevational view of a connector for transverse lines.

FIG. 36 depicts the locking mechanism of FIGS. 35 to 35D in a fully locked position, blocking the line.

FIGS. 37A and 37B depict the locking mechanism in a partially locked position, with the line unblocked in FIG. 37A and the line blocked in FIG. 37B.

FIGS. 38A and 38B depict the same locking mechanism as in FIGS. 37A and 37B, but with spacers as well as spheres in the lines. FIG. 38A shows the line unblocked and FIG. 38B shows the line blocked.

DETAILED DESCRIPTION

Figure 1A:
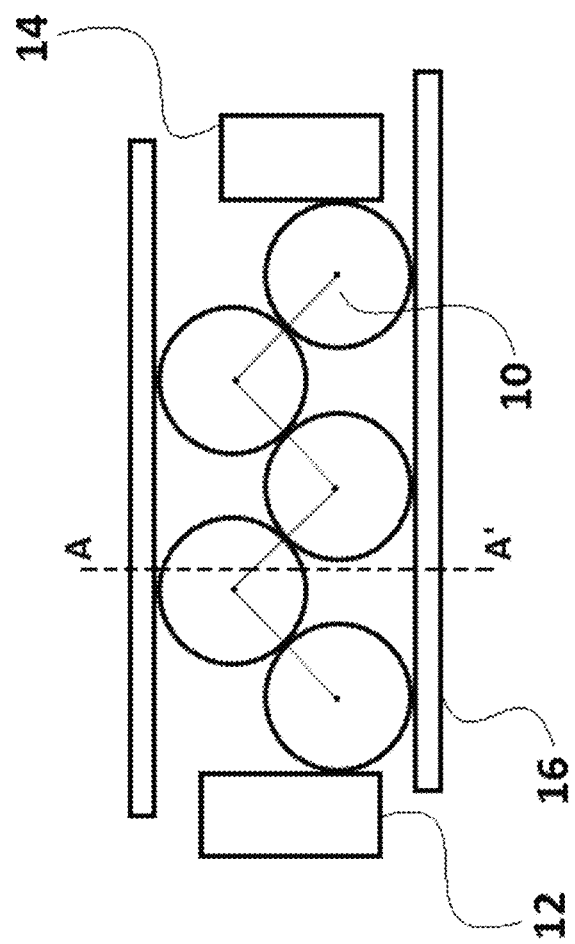
FIGS. 1A-1E illustrate solid media packed inside a lumen of a line.

As used herein, the term "a" or "an", when used in conjunction with the term "comprising" in the claims and/or the specification, may refer to "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "or" in the claims refers to "and/or" unless explicitly indicated to refer to alternatives only or the alternatives are mutually exclusive, although the disclosure supports a definition that refers to only alternatives and "and/or."

As used herein, the terms "computer" refers to one or more machines that comprise at least a memory, a processor and at least one wired and/or wireless network connection. A computer may comprise a desktop or laptop machine or other electronic media, for example, a smartphone or tablet, as are standard and currently known in the art. Without being limiting, any software, modules, applications, add-ons, plug-ins, programs and/or databases, etc. necessary for implementation of, but not limited to, the robot system, including the robotic manipulator, robotic sensors, etc., may be programmed into one or more computer, may be retrieved over the network connection or may be retrieved from a media storage device tangibly storing the same, may be tangibly stored in computer memory or other electronic media memory and are executable by the processor.

As used herein, the terms "instrument" refers to any surgical or non-surgical interventional tool, device, instrument or object, including blades, scalpels, scissors, syringes or biopsy apparatus.

As used herein, the terms "robot" or "robotic manipulator" interchangeably refer to the remotely actuated manipulator for performing, for example, but not limited to, manipulator-assisted surgical, minimally invasive surgical and interventional diagnostic or therapeutic or a combination of diagnostic and therapeutic procedures, as described herein.

As used herein, the term "patient" refers to any mammal, preferably a human, that is the subject of a surgical procedure or intervention utilizing the image-guided robotic device and system described herein.

The parent application, Ser. No. 14/010,155 describes guided robots, for image-guided robot-assisted surgical and intervention procedures, which use solid media movable in an actuation transmission line (or channel) to move surgical instruments or other portions of the robot. The parent application Ser. No. 14/011,574 describes software for such robots. Familiarity with these disclosures is assumed, insofar as they relate to or aid in understanding the subject matter below.

The actuation transmission line is preferably flexible, but may include rigid sections. The actuation transmission line may include a loader mechanism for maintaining solid media under axial pressure before and/or during operation. Providing a known axial pressure is useful and important in determining the efficiency of force applied to generating movement of the media. In a preferred embodiment, the loader can include pistons or other apparatus extending into the line, from the ends or from a slot in a region between the ends.

Figure 1B:
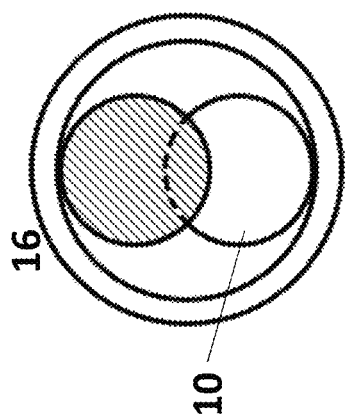
Figure 1C:
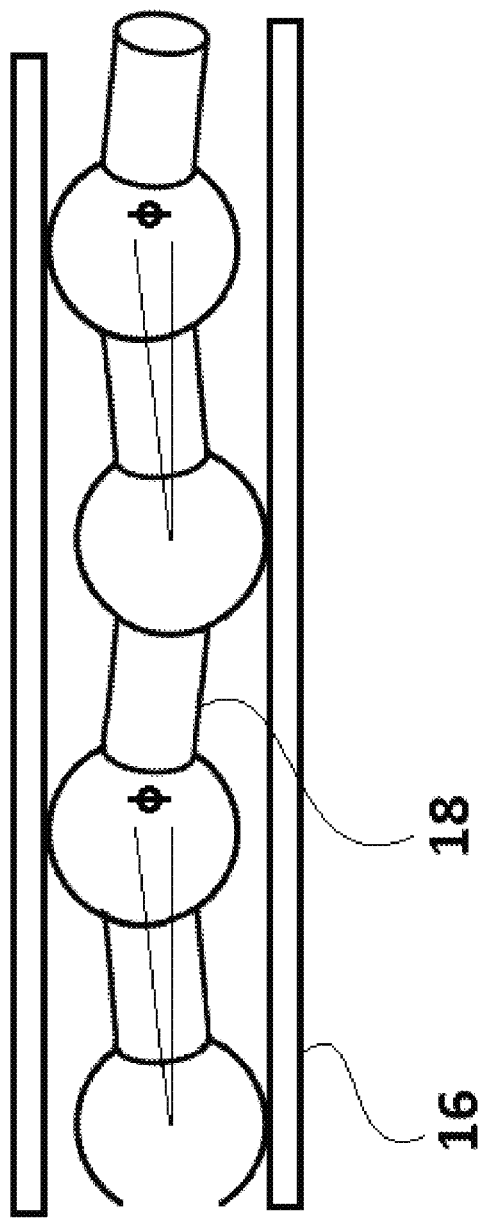

FIGS. 1A and 1B show that spheres 10 loaded by squeezing them between two members 12 and 14, generates some level of riding up on an adjacent sphere, thus generating lines joining the sphere's centers lying at an angle Φ from the horizontal. If the spheres rise up and touch the upper portion of the line 16 (as shown), there is additional friction, and sphere-sphere contact, which generates any vertical sphere component of motion will also significantly increase friction. So loading significantly affects the force required for moving the spheres through the line, and therefore, the efficiency of force transfer from a power unit to the robot or instrument.

Figure 1D:
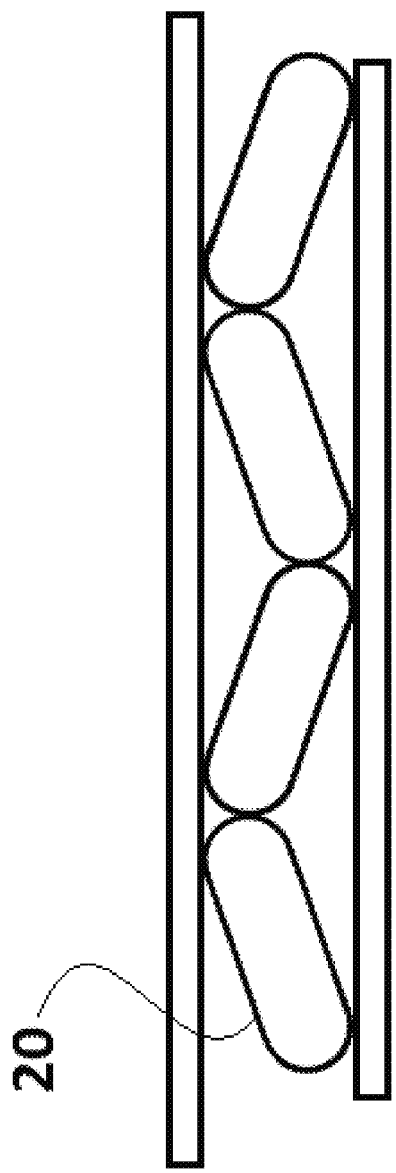
Figure 1E:
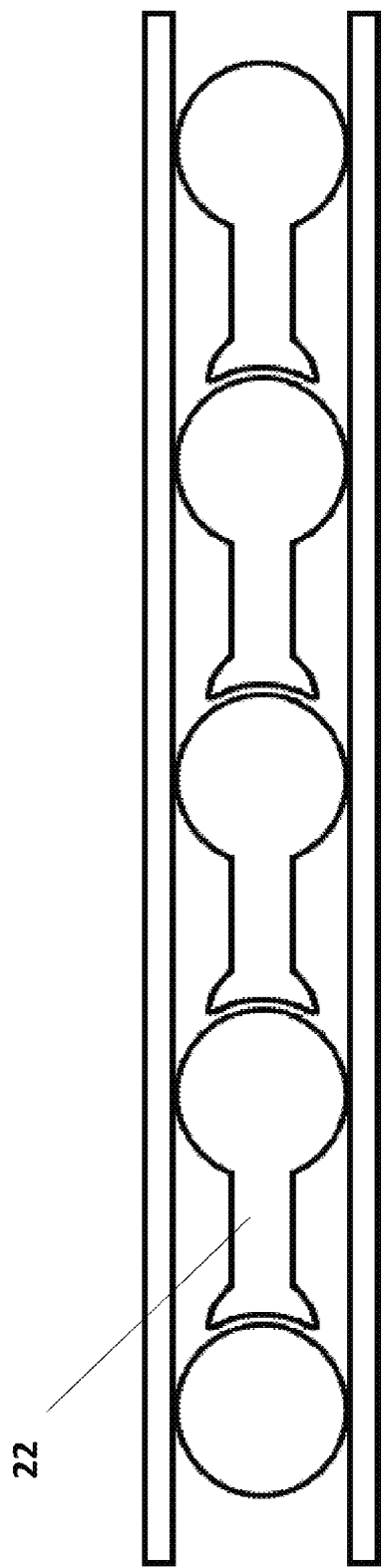
Figure 10C:
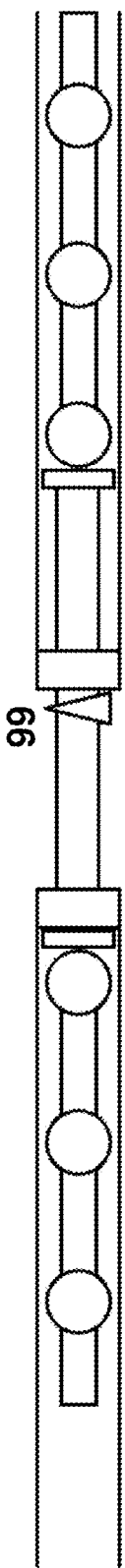

FIG. 10 shows spheres 10 separated in line 16 by cylindrical spacers 18. FIG. 1D shows oblong-shaped media 20 in line 16. FIG. 1E shows media 22 having mating surfaces between adjacent media in line 16.

Figure 2:
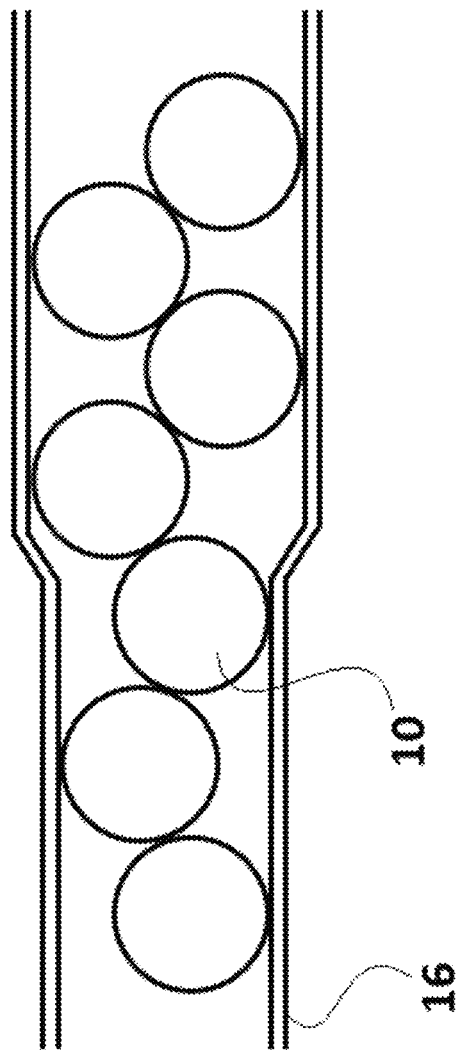
FIG. 2 is an axial sectional view of a line having two sections, each with a different internal diameter.

FIG. 2 represents that for lines joining the centers of spheres, their angle Φ from the horizontal will increase in sections of line 16 where the inner diameter is expanded. Again such effects can significantly affect the friction and the force required for moving the spheres through the line, and therefore, the efficiency of force transfer from a power unit to the robot or instrument.

Figure 3A:
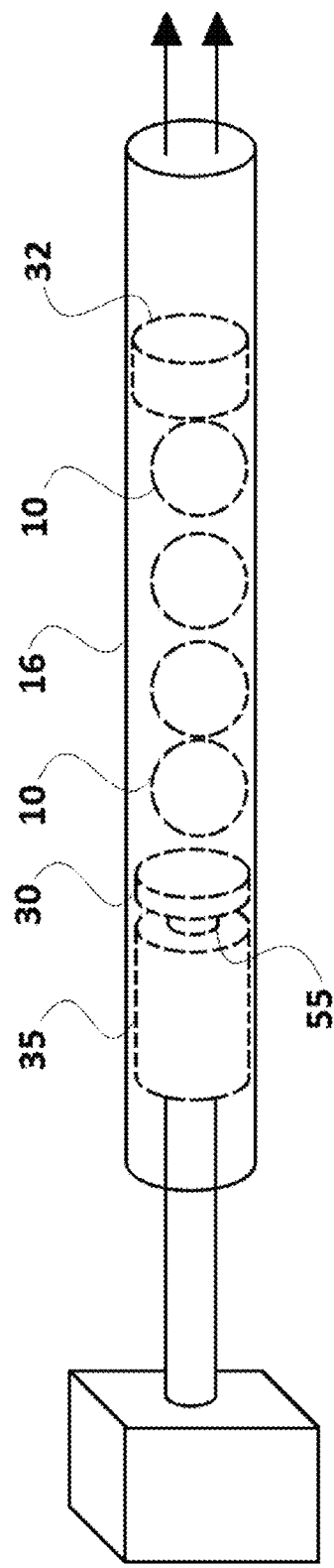
Figure 3B:
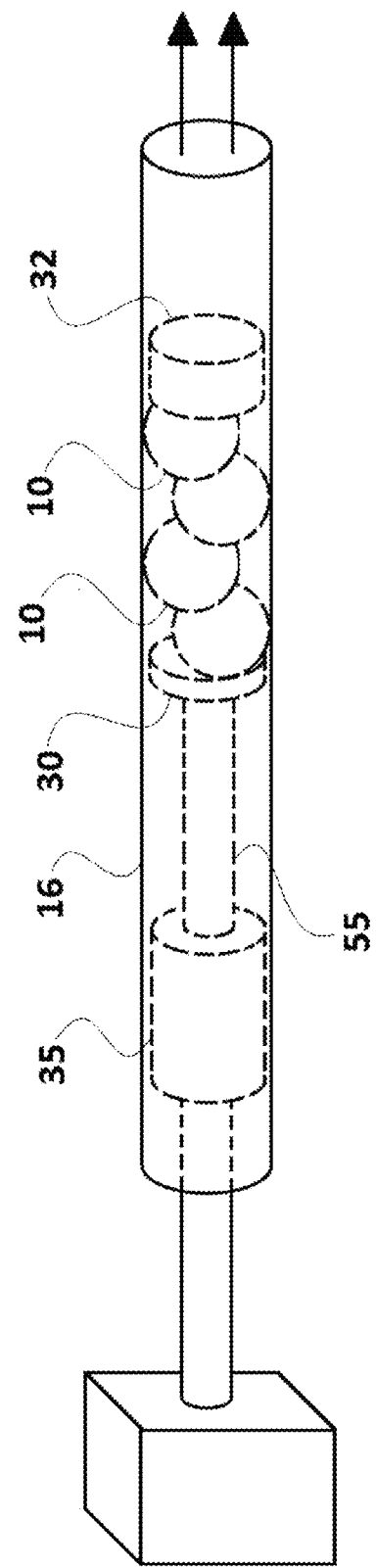

FIG. 3A shows a loader with piston-like portion 55 in starting position in line 16, and going through actuation in FIGS. 3B and 3C. A driving source 35 for turning the tensioning screw portion (upstream of source 35) and pushing the piston-like structure 55, such as manual force, includes an electric motor and hydraulic lines and chambers. One face of each of media blockers 30 and 32 contact spheres 10. The outside face of blocker 32 transmits force to other portions of the robot or to the instrument.

FIG. 3B depicts that the loader has bridged these gaps between spheres 10 by compressing them together. FIG. 3C depicts that the pre-packed actuation transmission line 16 is able to more accurately transmit actuation due to the closed gaps between spheres 10.

Figure 4A:
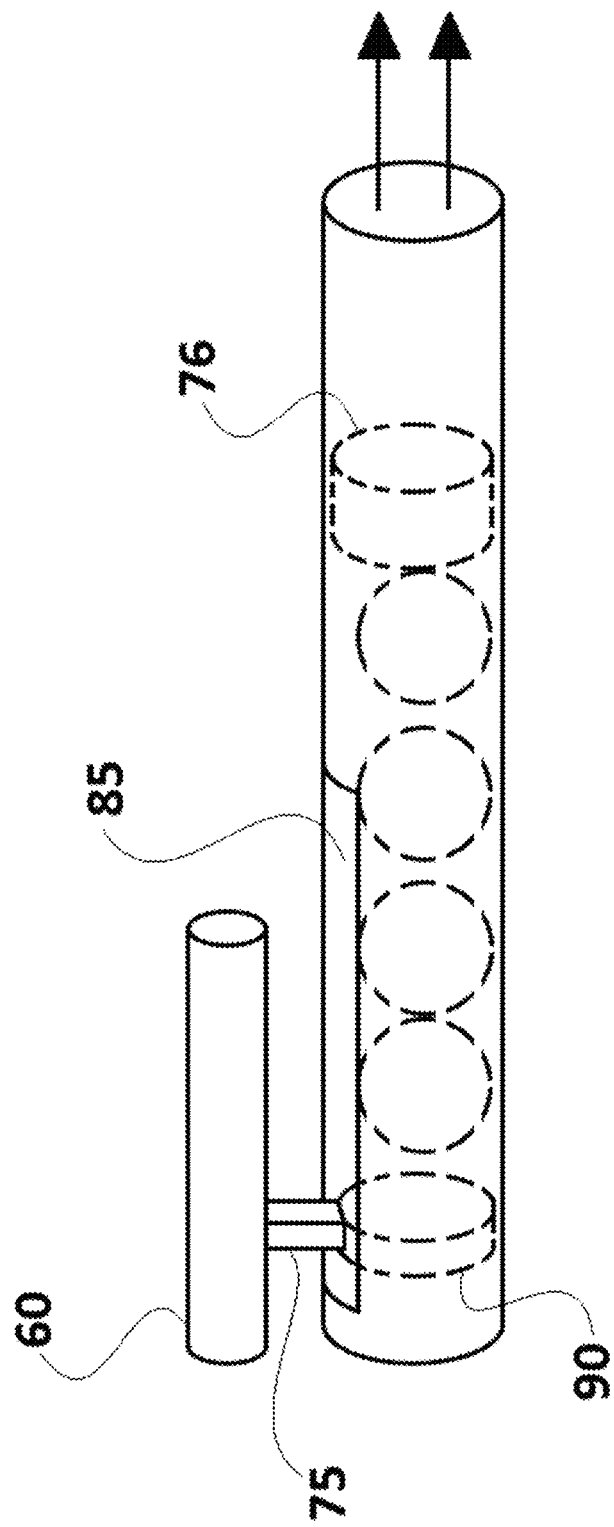
FIGS. 4A-4C illustrate an alternative type of loader that is substantially located outside the lumen but linked into the lumen for packing media into the channel.
Figure 4B:
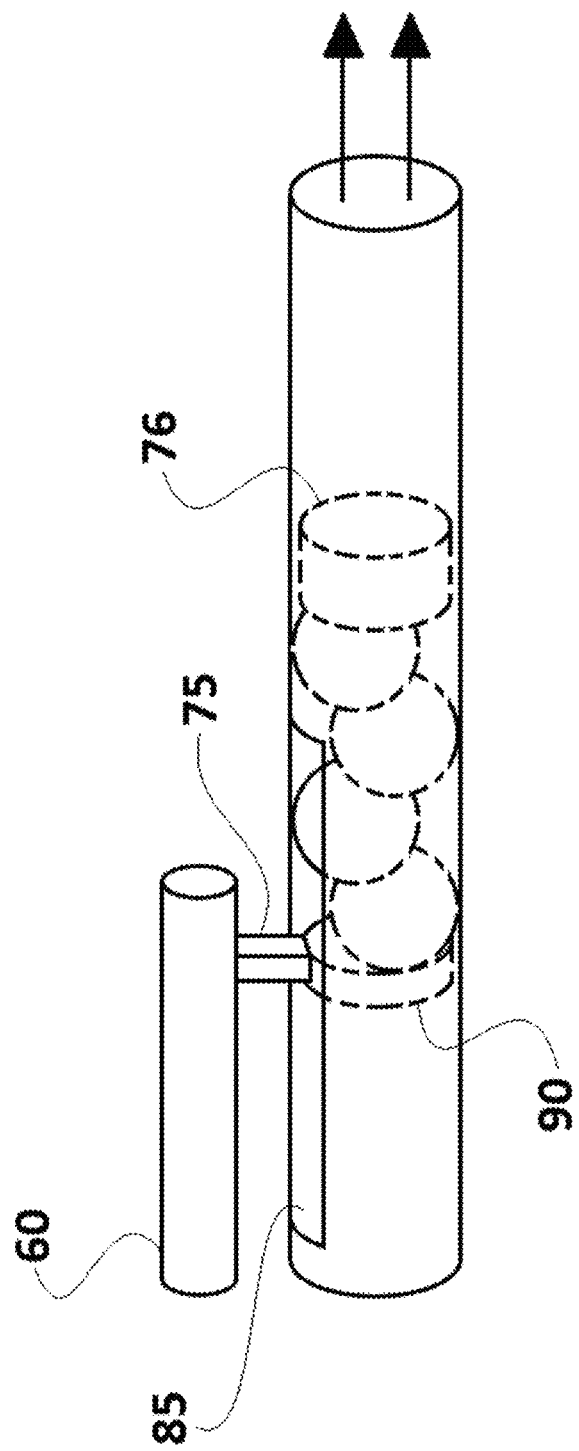
Figure 4C:
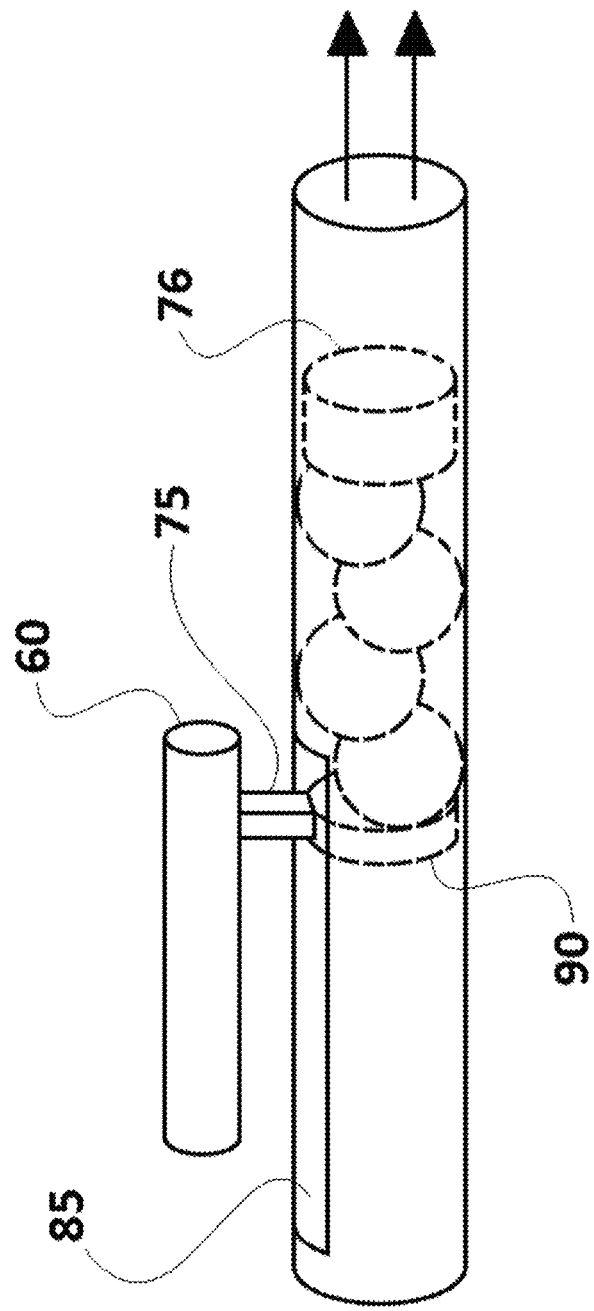

FIGS. 4A to 4C depict a loader mechanism including power unit 60, leg 75, which slides in gap 85, and leg 75 attached to plate 90, which contacts spheres 10. Moving leg 75 to the right along gap 85 first compresses the spheres 10 (FIG. 4A) and then moves them to the right (FIG. 4C) with the opposing blocker 76.

Figure 5A:
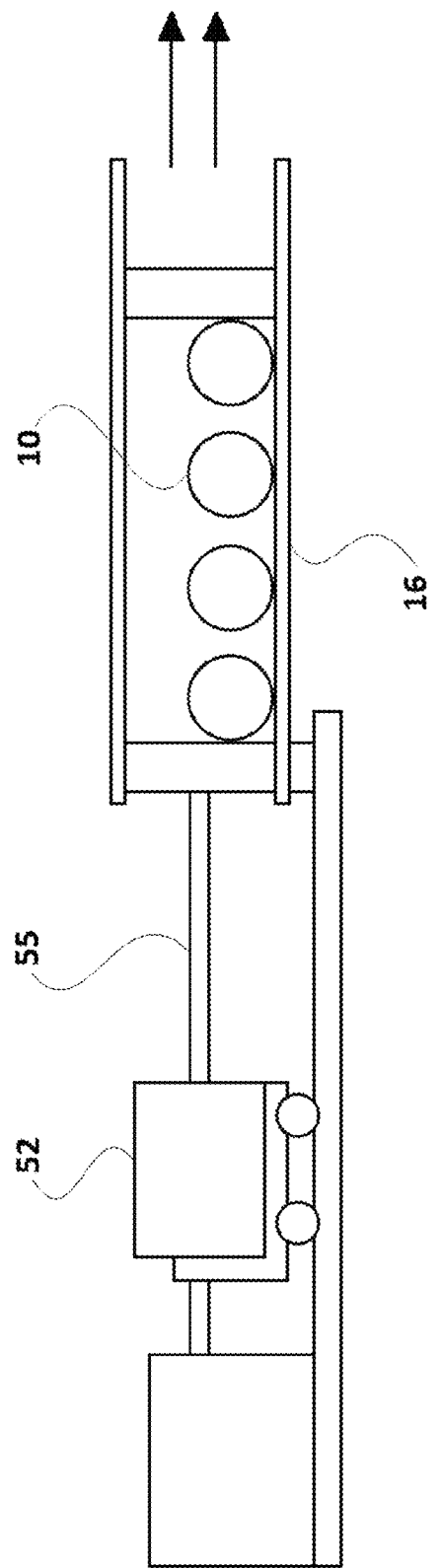
FIGS. 5A-5C illustrate the implementation of an alternative type of dual-motor loader that packs media.
Figure 5B:
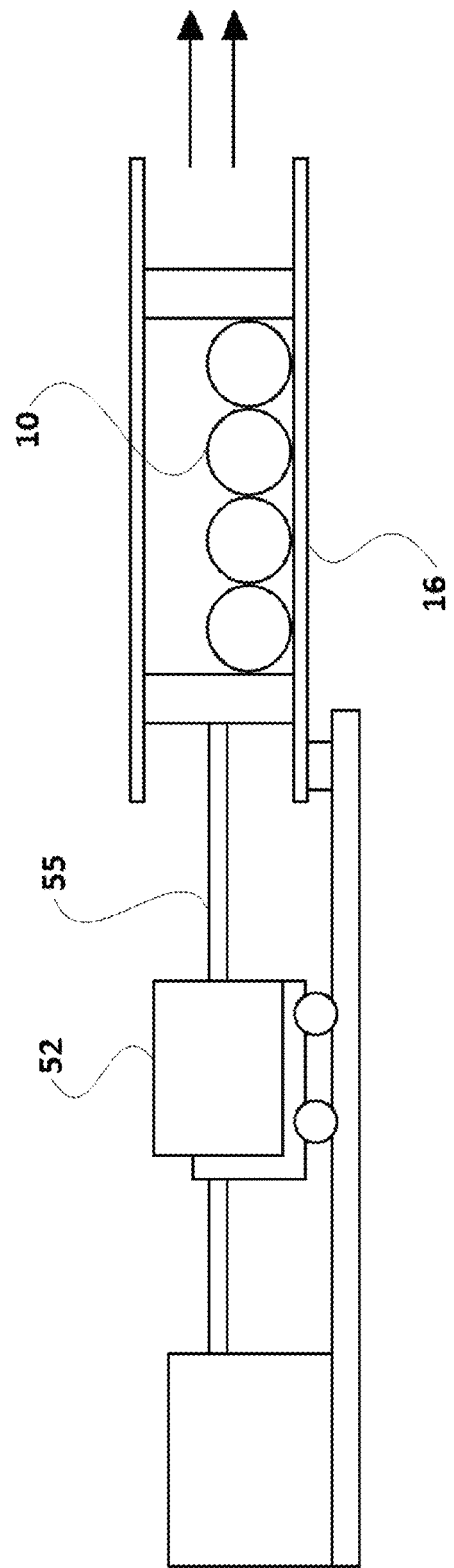
Figure 5C:
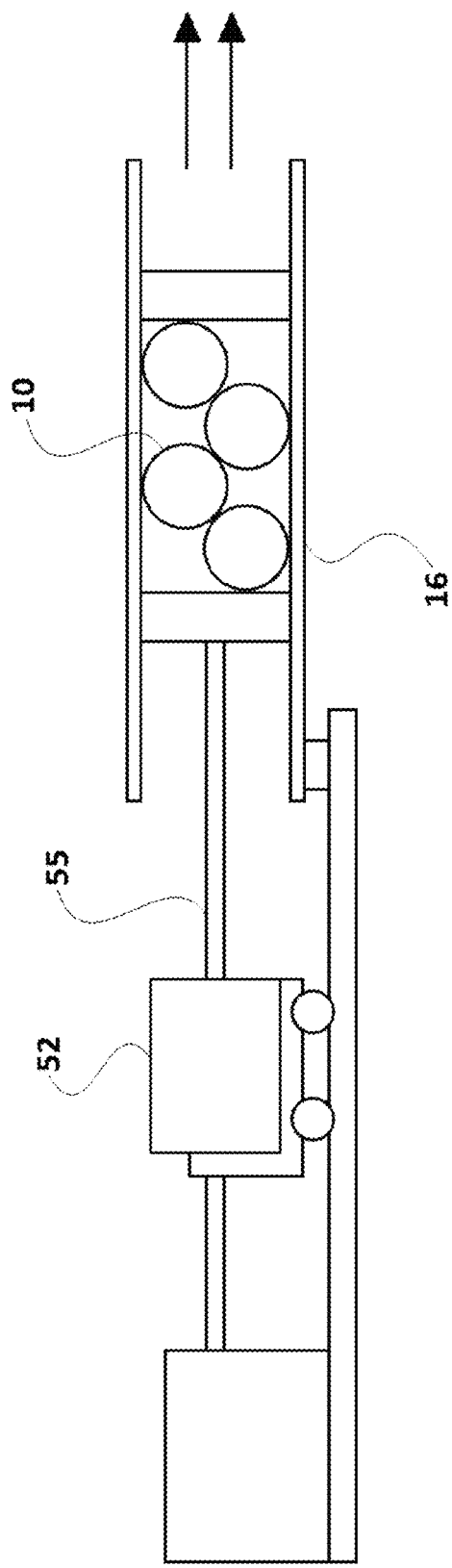

FIGS. 5A to 5C depict a similar loader mechanism to that in FIGS. 3A to 3C, except that it employs power movable vehicles 52, which slide towards the spheres 10 and can further extend a piston 55 to contact spheres 10.

Figure 6A:
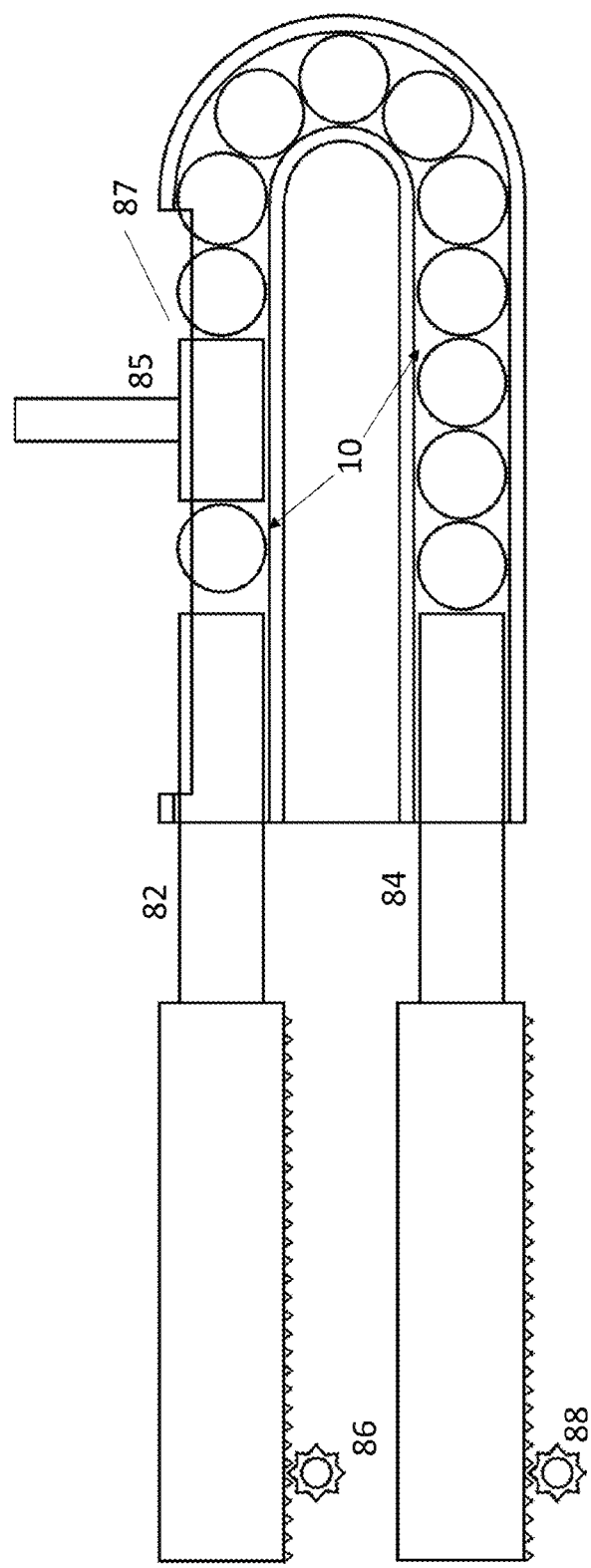
FIG. 6A illustrates use of two gears to drive pistons inside a lumen in opposite directions.
Figure 6B:
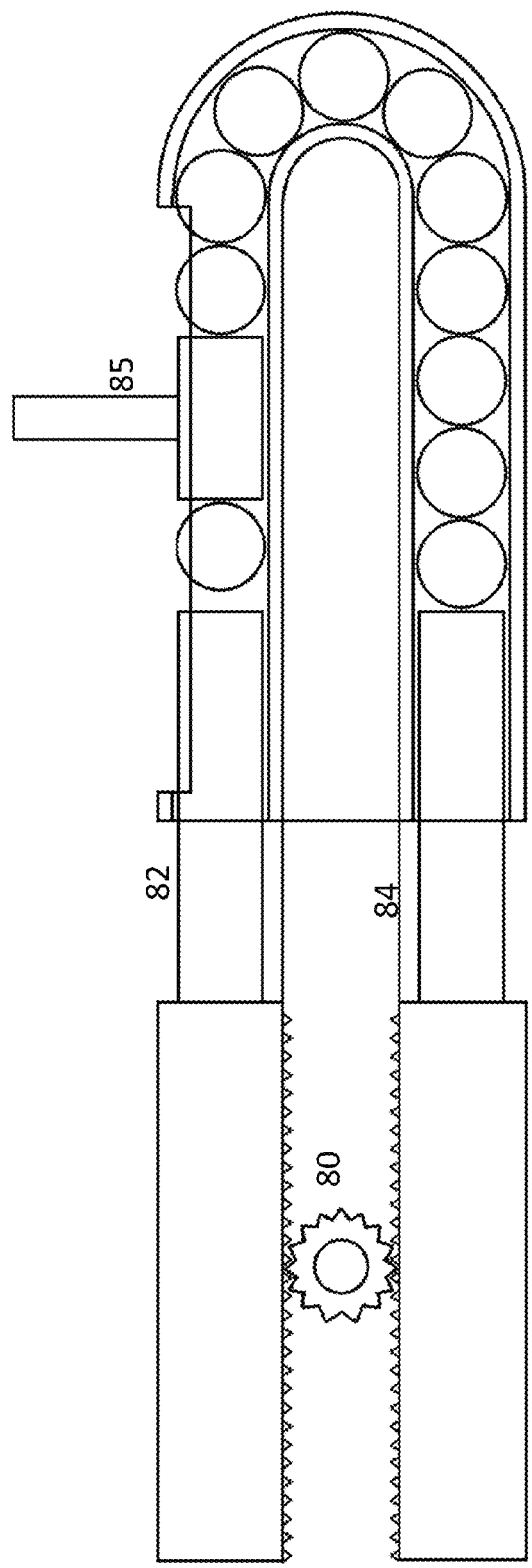
FIG. 6B illustrates use of one gear to drive pistons inside a lumen in opposite directions.

FIG. 6A demonstrates that one can use two oppositely rotating gears (86 and 88) to advances piston 82 in the direction of spheres 10 while withdrawing piston 84; or, to advance piston 84 while withdrawing piston 82. FIG. 6B shows a fixed gear 80 which, depending on direction of rotation, achieves the same effect as oppositely rotating gears 86 and 88. Either system can be used in a closed loop (as shown) where bi-directional motion of spheres 10 is needed. Alternatively, instead of driving rotations of the gears (80, 86 or 88) one can move the spheres 10 by moving member 85 along its slot 87.

Figure 7A:
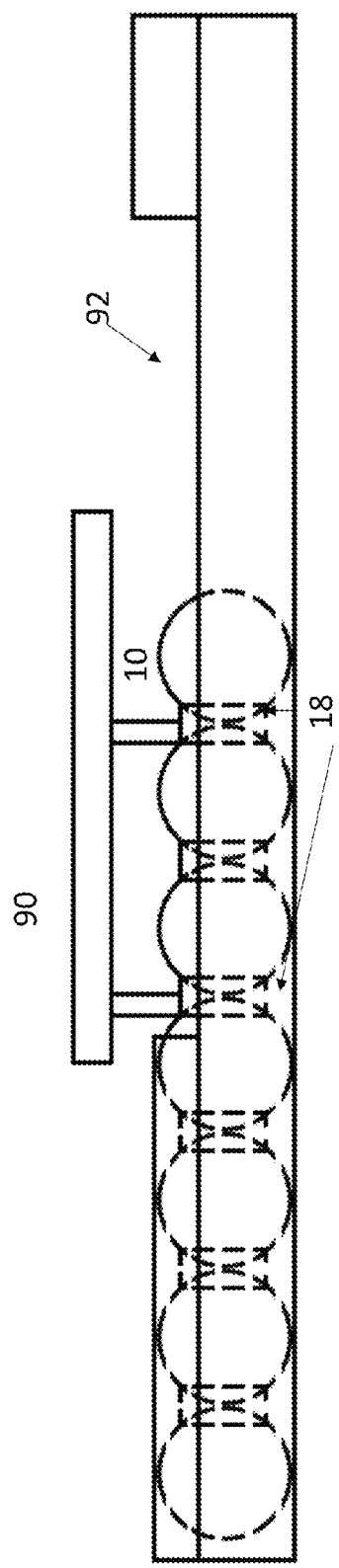
FIG. 7A illustrates axial sections views of a line with a slit along a section of its length and an apparatus to drive solid media in the lines.
Figure 7B:
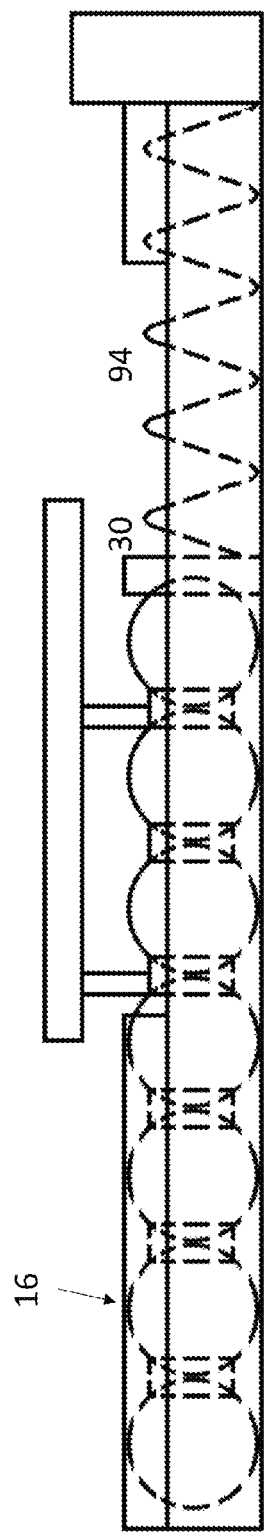
FIG. 7B depicts the same drive apparatus as FIG. 7A and including a spring in the line.

FIG. 7A shows spheres 10 in tube 16 separated by spacers 18, and where two of the spacers 18 are attached to a bar 90. Bar 90 can be moved by a power source along slot 92. FIG. 7B shows a similar configuration to FIG. 7A, but with a spring 94 between a blocker 30 and the end of line 16. Spring 94 provides loading force on spheres 10.

Figure 7C:
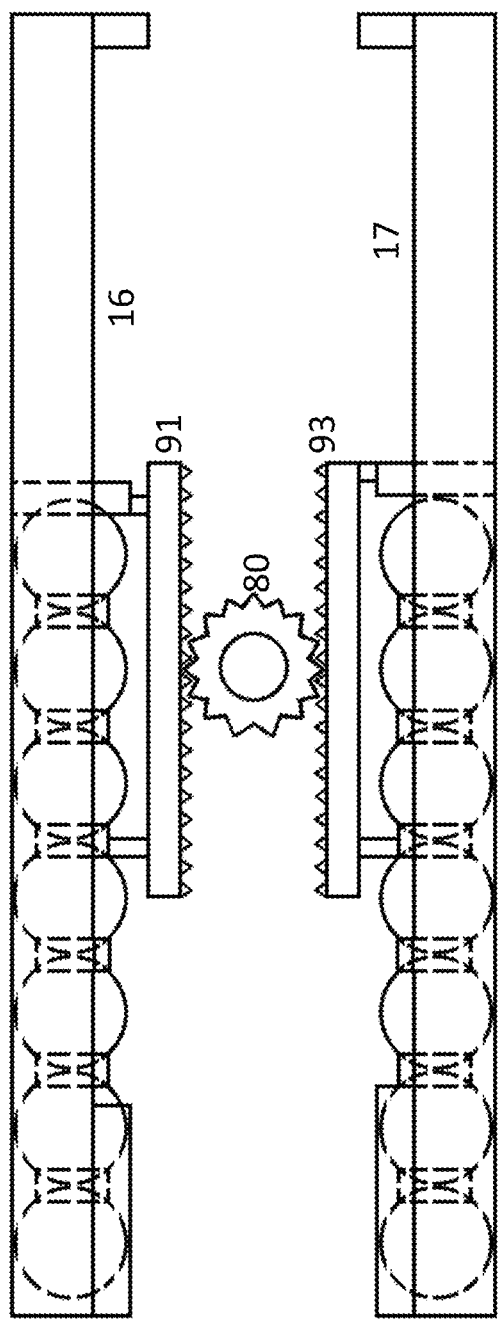
FIG. 7C depicts a similar drive apparatus as FIG. 7A and with a single gear to move the apparatus.

FIG. 7C shows a similar arrangement of components to that shown in FIG. 7A, but with a fixed gear 80 moving bars 91 and 93 of the upper and lower lines 16 and 17, respectively, in opposite directions. Such a system is particularly preferable in a closed-loop system, where one end of each of upper and lower lines 16, 17 are connected.

Figure 7D:
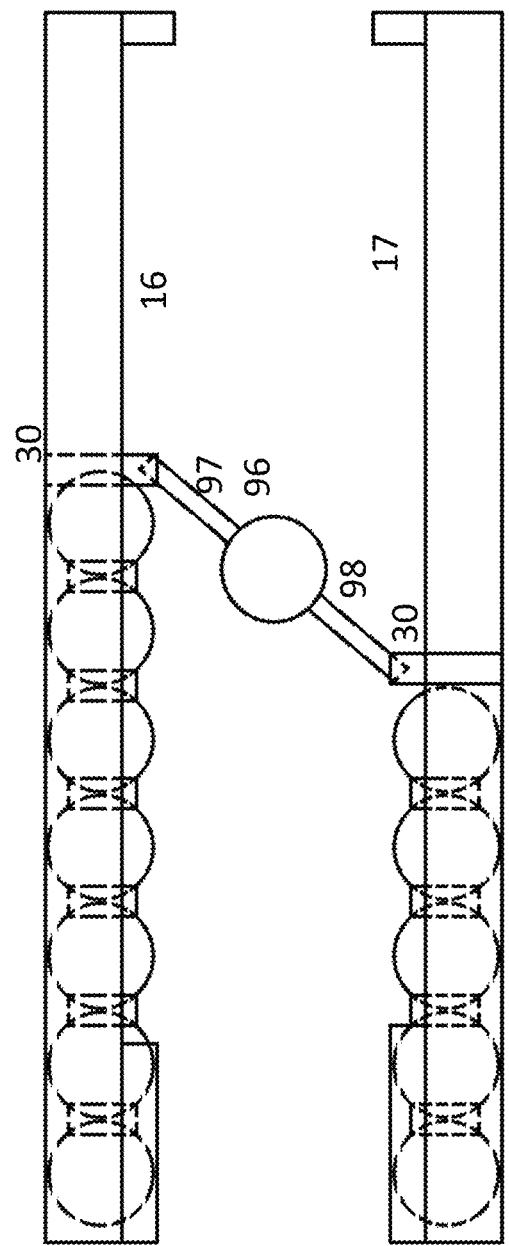
FIG. 7D depicts a drive apparatus which can move solid media in two different lines simultaneously.

FIG. 7D shows that blockers 30 in the upper and lower tubes 16, 17 can be linked with a member 96, having telescoping or other means of passively extending and contracting its arms 97, 98, where member 96 can be driven by a rotating gear connected behind its central portion (not shown). Such a member 96 can also be used to drive spheres 10 in opposite directions inside upper and lower lines 16, 17.

Figure 7E:
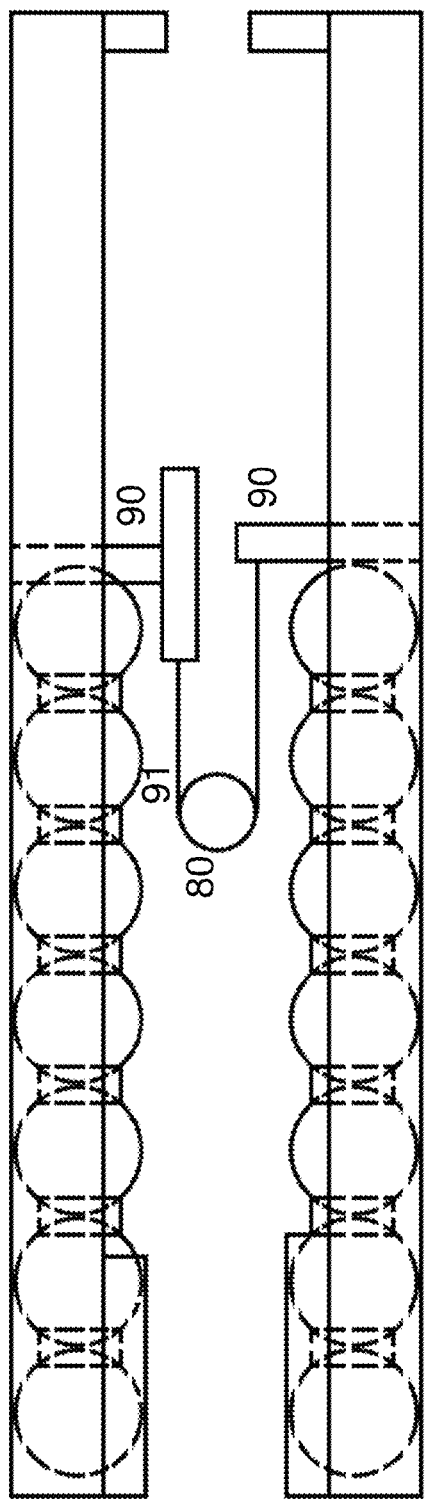
FIG. 7E depicts another type of drive apparatus which can move solid media in two different lines with a belt drive system.
Figure 7F:
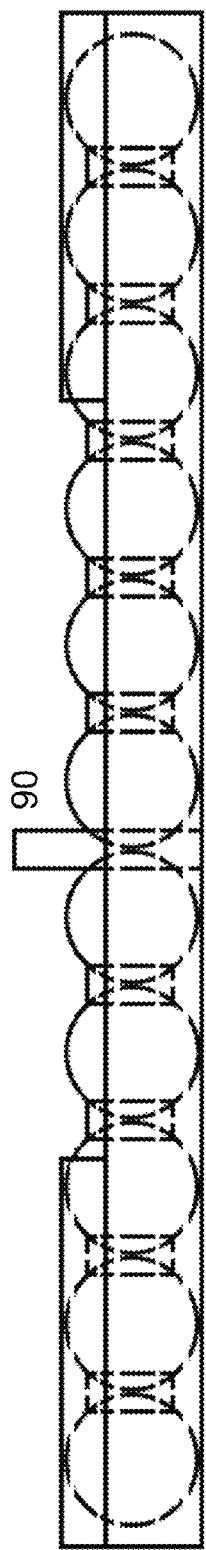
FIG. 7F depicts another type of drive apparatus.
Figure 7G:
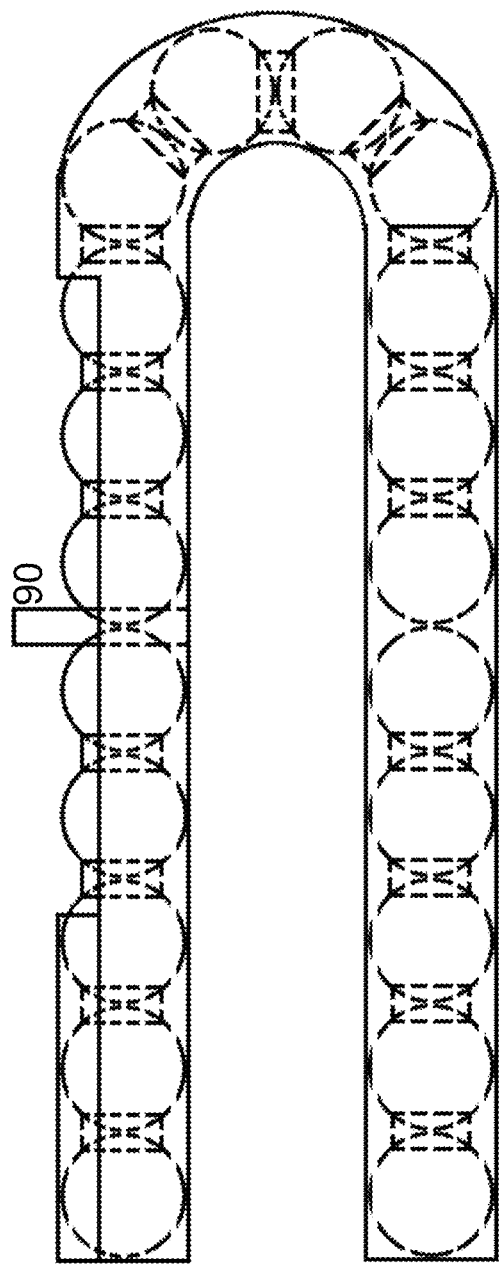
FIG. 7G depicts another type of drive apparatus and line arrangement for moving solid media in opposite directions.
Figure 7H:
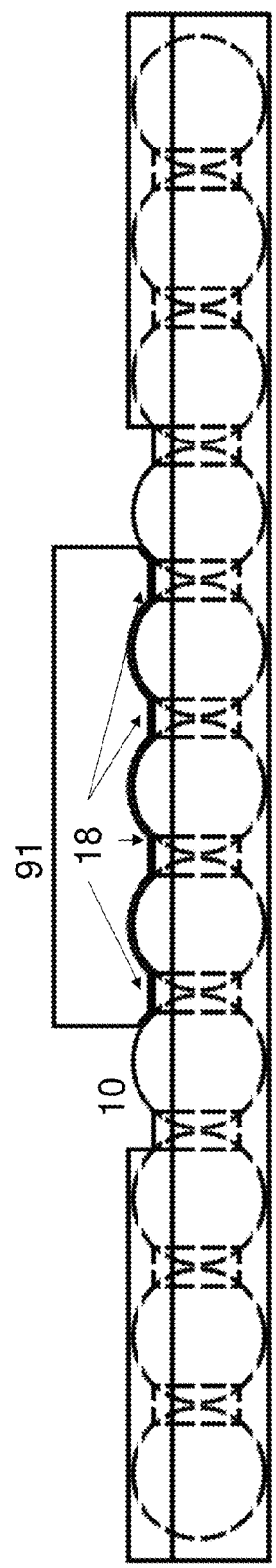
FIG. 7H depicts a different attachment for a different drive apparatus than shown in FIGS. 7A to 7G.

FIG. 7E shows a similar bi-directional motion system to FIG. 7C, except that a belt 91 is linked to bars 90, and the belt is driven by gear 80. FIG. 7F illustrates using a bar 90 which can be moved by a power source to generate bi-directional sphere motion in a non-looped system, and FIG. 7G illustrates using bar 90 to generate bi-directional motion in a looped system. FIG. 7H represents attaching an axial member 91 to spacers 18 whereby member 91 can be linked to a power source to move spheres 10 bi-directionally.

Figure 8A:
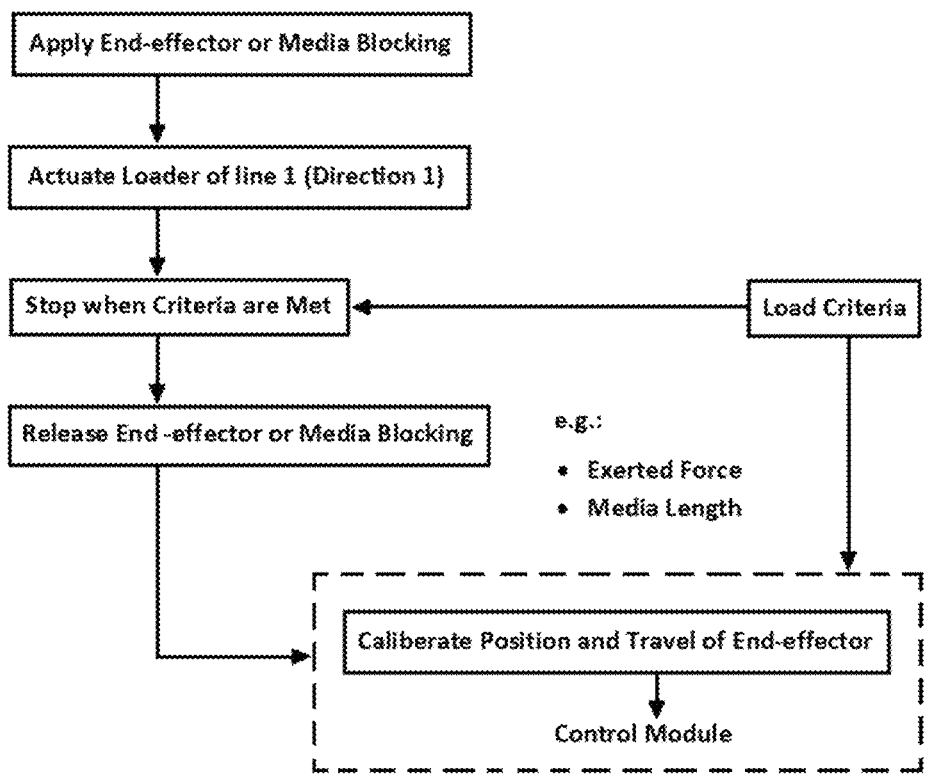
FIG. 8A is a flowchart for using loaders to adjust force applied to media, and monitoring travel to a selected point, with one motor for a bidirectional line.
Figure 8B:
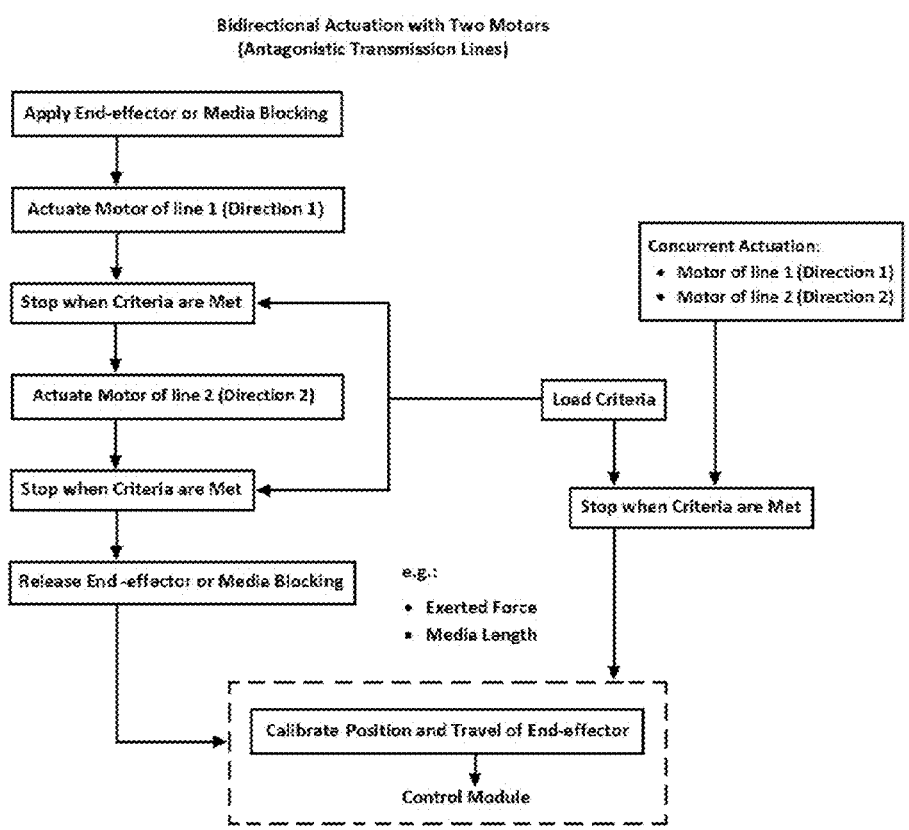
FIG. 8B is a flowchart for using loaders to adjust force applied to media, and monitoring travel to a selected point, with one motor for each of two one-directional lines, where each line moves the media in the opposite direction.

FIG. 8A is a flow chart showing the steps in actuation of a line of solid media using one motor or power source, and allowing adjusting the loading and the relative position of the media in relation to each other based on travel of a blocking member. FIG. 8B is a flow chart showing the steps in actuation of a line of solid media using one motor or power source, in a looped system (antagonistic to opposing directions of travel of spheres), and allowing adjusting the loading and the relative position of the media in relation to each other based on travel of a blocking member.

Figure 9A:
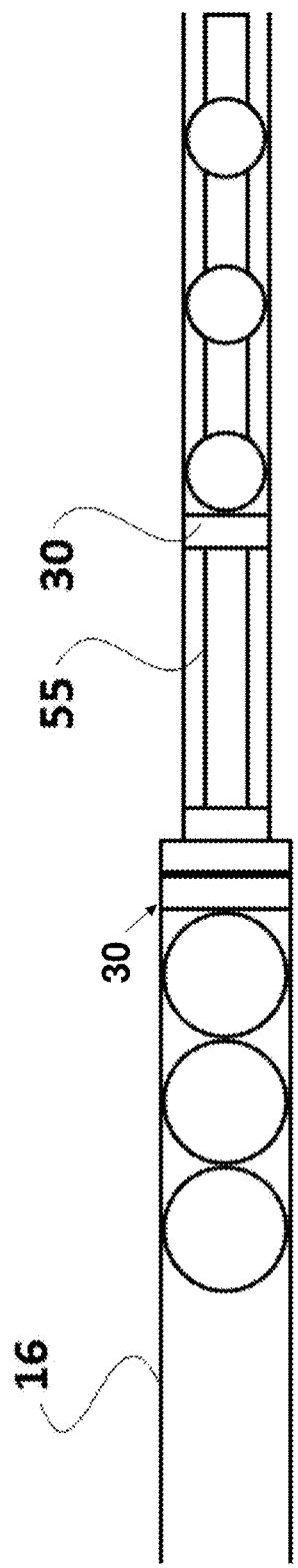
FIGS. 9A-9C illustrate that tubes of two different sizes are connected by a line size converter piston.
Figure 9B:
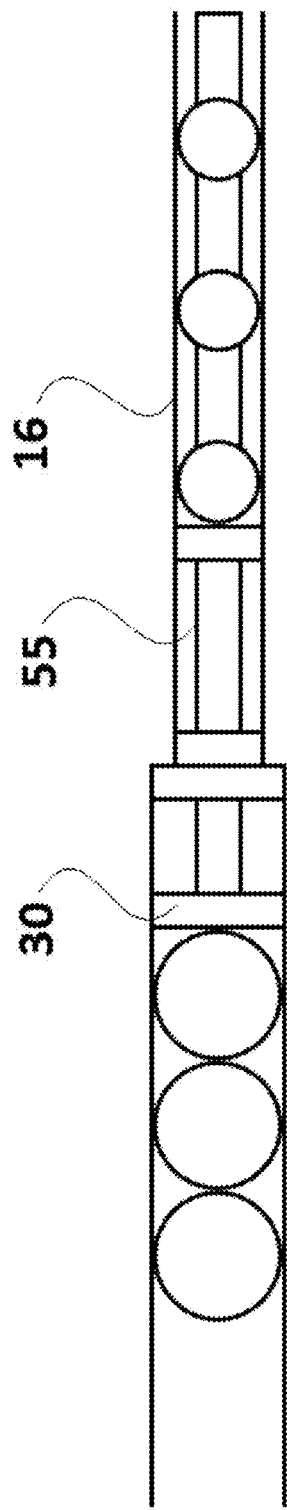
Figure 9C:
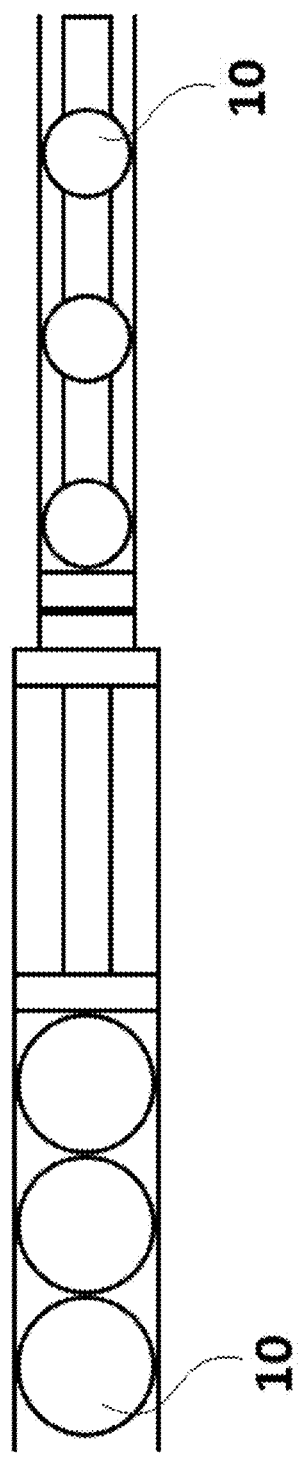

FIGS. 9A to 9C show a line 16 having a wider and a narrower section (left to right), and including a piston 55 with heads 30 pushing solid media 10. The piston is pushed from right to left in FIGS. 9A to 9C. FIGS. 10A to 10O show a similar arrangement of spheres 10 and spacers 18 to FIGS. 9A to 9C, but here, the piston 55 is moved by linking member 99 to a power source.

Figure 11A:
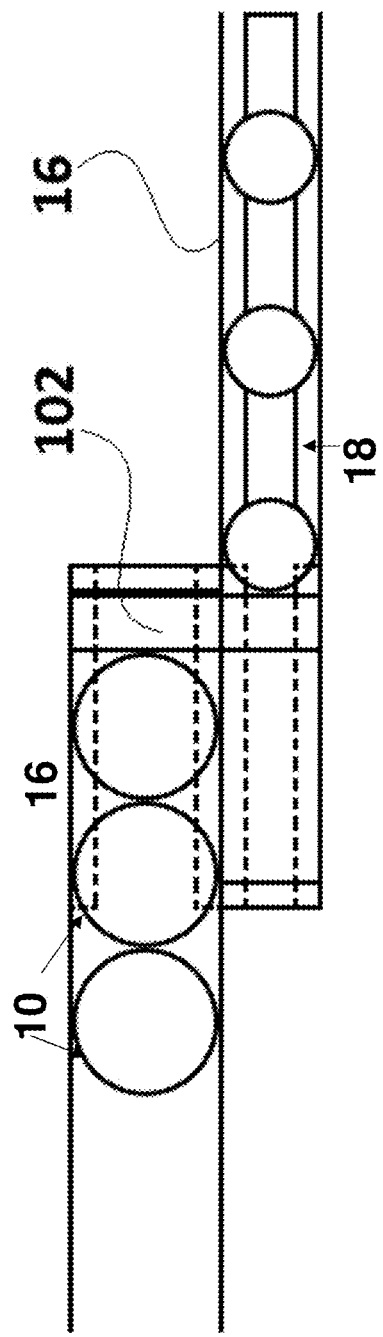

FIGS. 11A to 11O depict another mechanism to move spheres 10 (with or without spacers 18) in two different sections of line 16. Blocker 102 slides in slots 106, and slots 106 run along both the lower side of upper line 16, and along the upper side of lower line 16. Optionally, slots may also be in the upper side of upper line 16 and in the lower side of lower line 16, as shown.

Figure 12B:
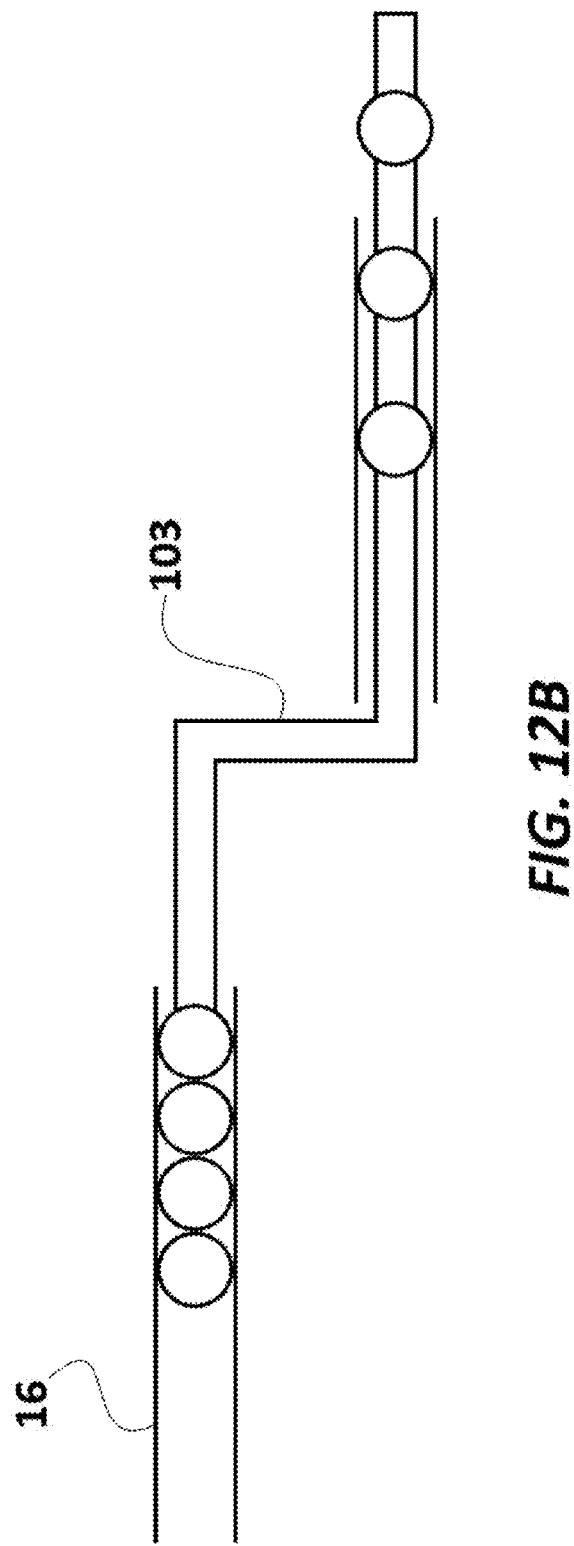
Figure 13A:
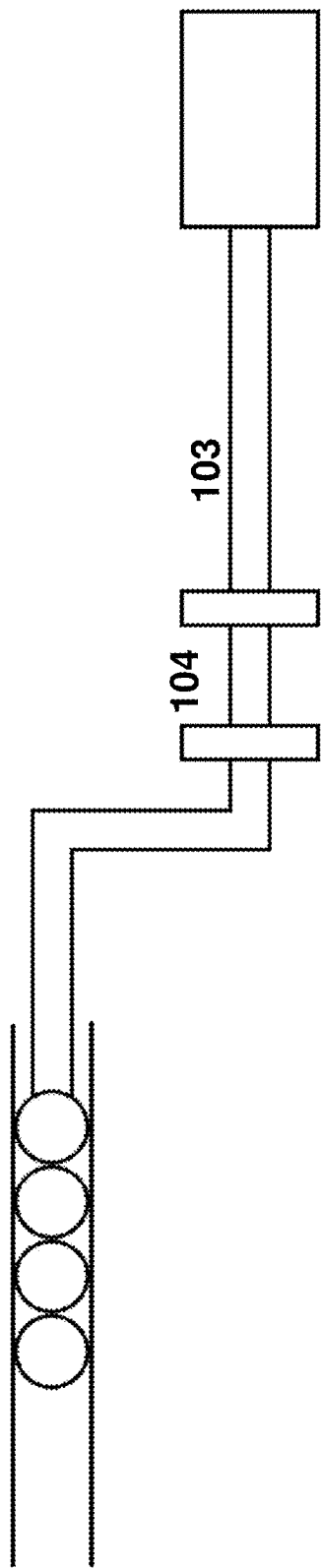
FIG. 13A shows two actuation lines at a offset axes, linked by offset pistons as in FIGS. 12A-12B, and including bearings for ease of link movement, in a starting position.

FIGS. 12A and 12B depict a two-headed piston 103 configured with two horizontal sections and one vertical section, which can transmit movement of spheres 10 in the upper section of line 16 to spheres 16 and spacers 18 in the lower section of line 16, and vice-versa. FIGS. 13A and 13B depict a similar two-headed piston 103 which includes bearings 104 to assist in movement of the piston by reducing the friction between its perimeter and the inner wall of the lower section of line 16.

Figure 14A:
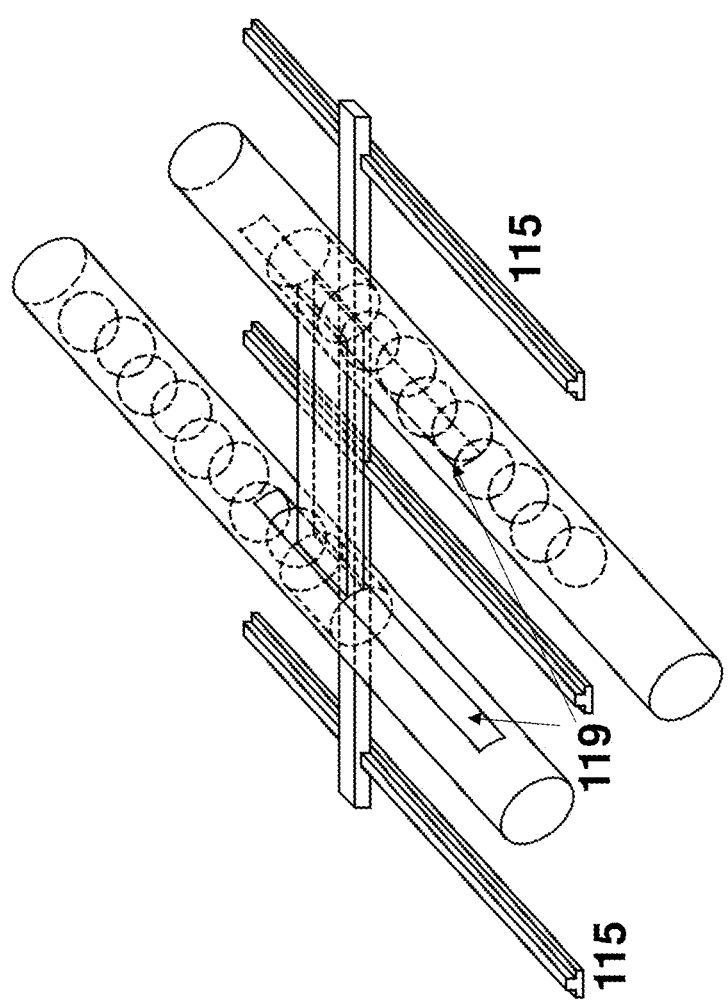
Figure 14B:
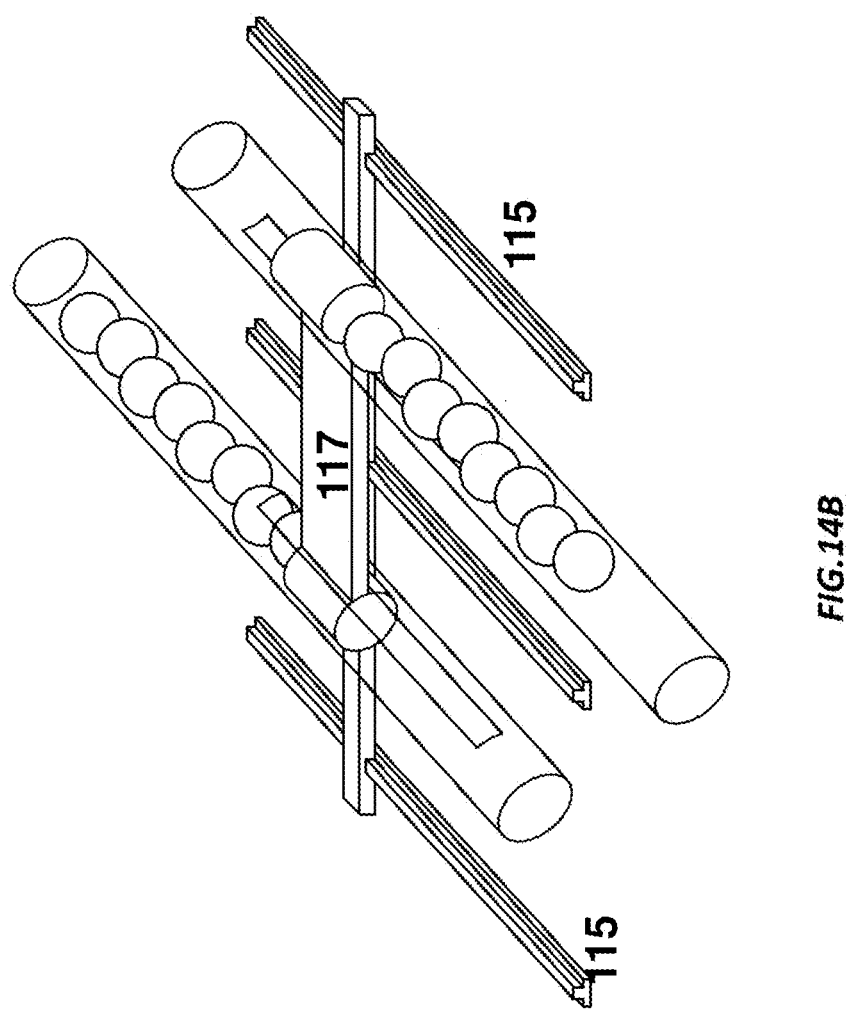

FIGS. 14A to 14C depict a similar arrangement of parallel lines 16 to that in FIGS. 11A to 11O, but also including rails 115 for guiding motion of the blocker 117 which slides in slots 119 in lines 16. The arrangement of lines in FIG. 14C is different from that in FIGS. 14A and 14B, and one set of the lines 16 in FIG. 14C include spacers 18 with spheres 10.

Figure 15A:
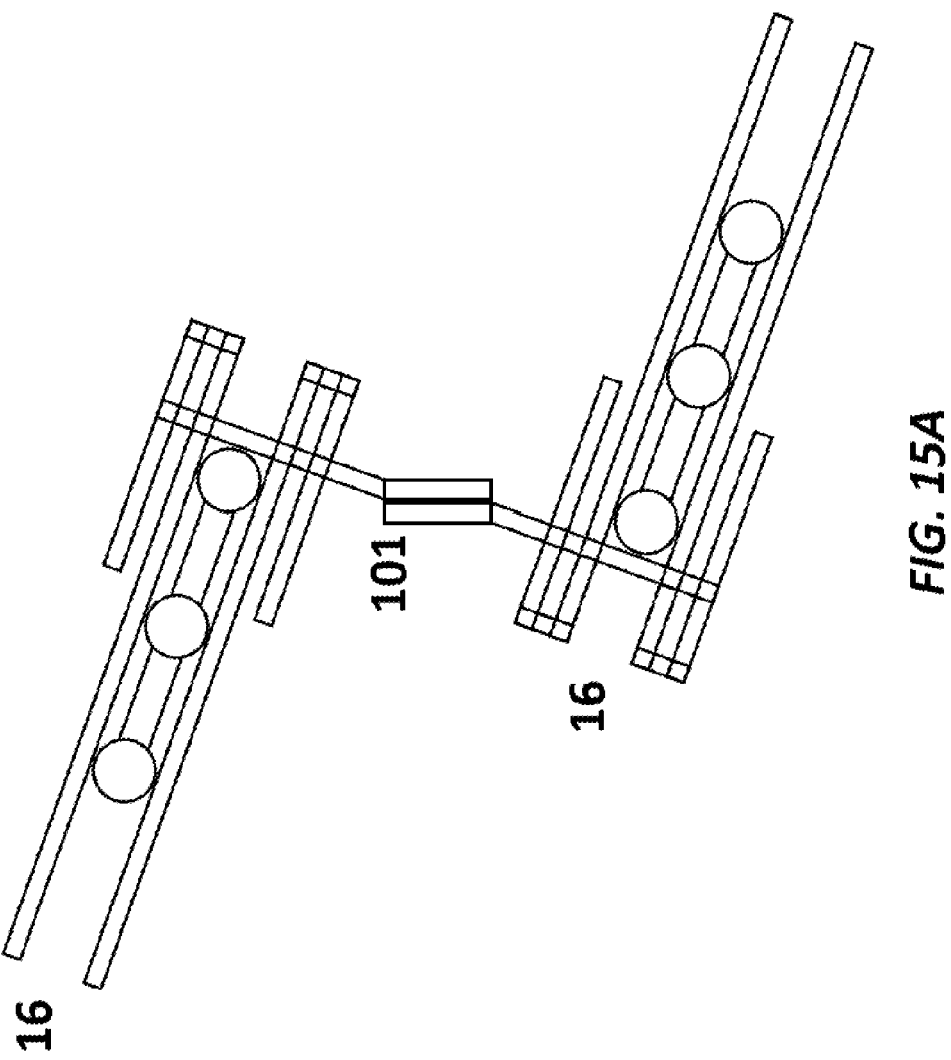
FIG. 15A is a cross-sectional view of a mechanical link that enables the two independent lines with offset axes to be mechanically linked with a flexible link to accommodate offset and/or non-parallel axes in the lines.

FIG. 15A depicts a similar arrangement of parallel lines 16 to that in FIGS. 14A to 14C, but with a flexible linkage 101 between the upper and lower lines 16. If the angle of the upper line 16 changes with respect to the lower line, the flexible linkage 101 can bend to accommodate such shifts. The flexible linkage 101 can be made of a rubber-like polymer or other flexible material.

Figure 15C:
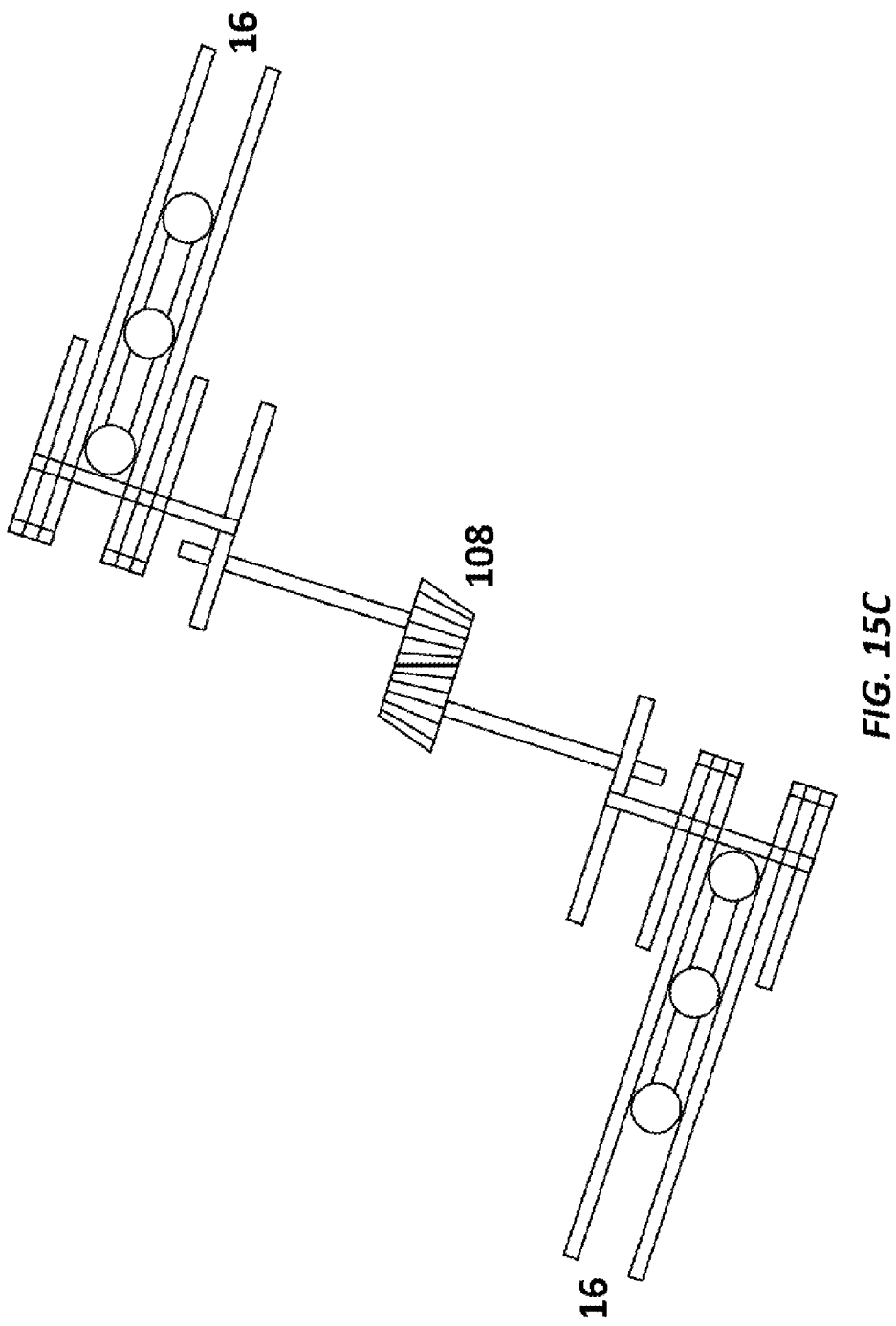

FIGS. 15B and 15C show angled gears 108 which can be angled to meet variations in the angle between the two sections of line 16 holding spheres 10.

Figure 16A:
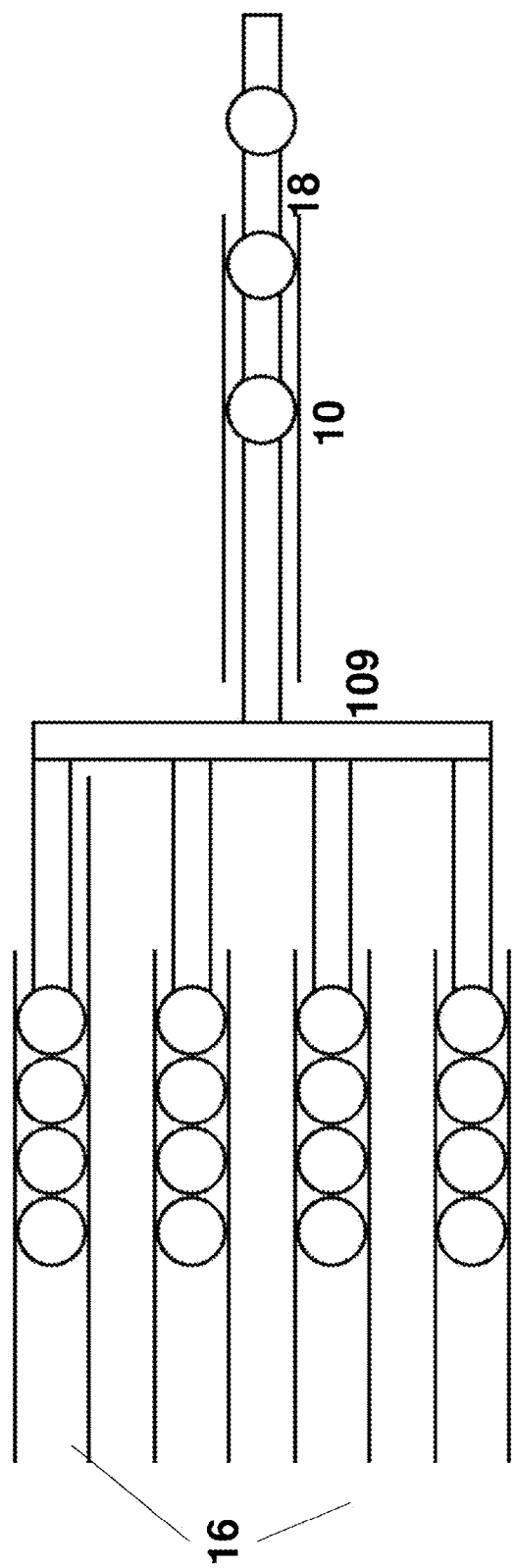
FIGS. 16A & 16B are cross-sectional views depicting a single piston with a single end disposed in a single transmission line mechanically linked to multiple pistons, each disposed in a separate transmission line.
Figure 16B:
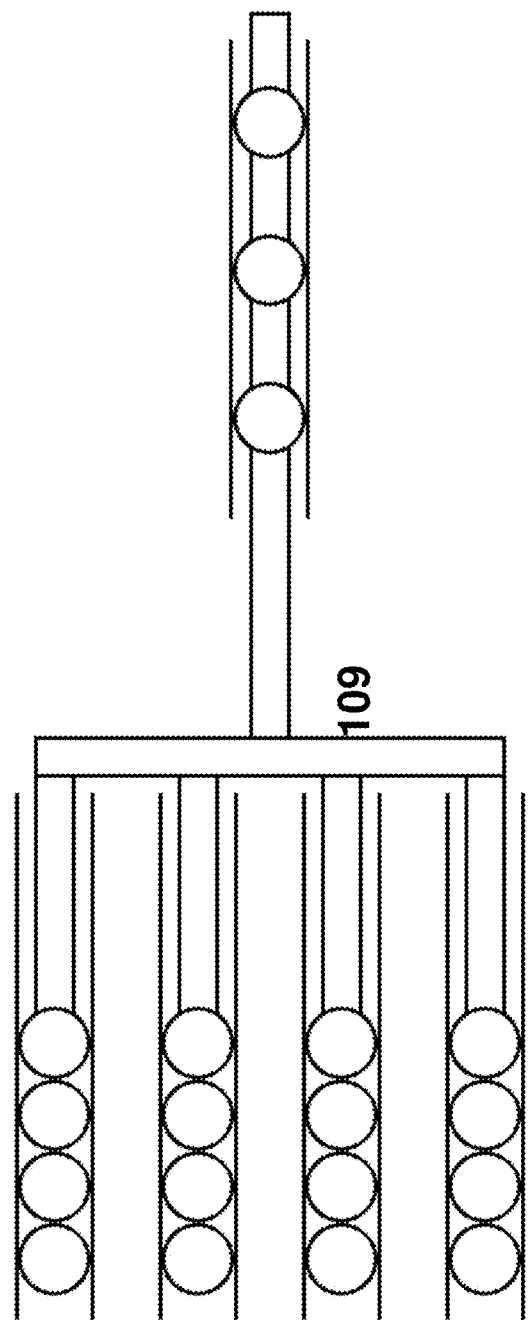

FIGS. 16A and 16B depict that one line with solid media (spheres 10 with spacers 18) can be linked with a linking device 109 as shown, to move spheres 10 in several lines (in this case, in four lines 16).

Figure 17A:
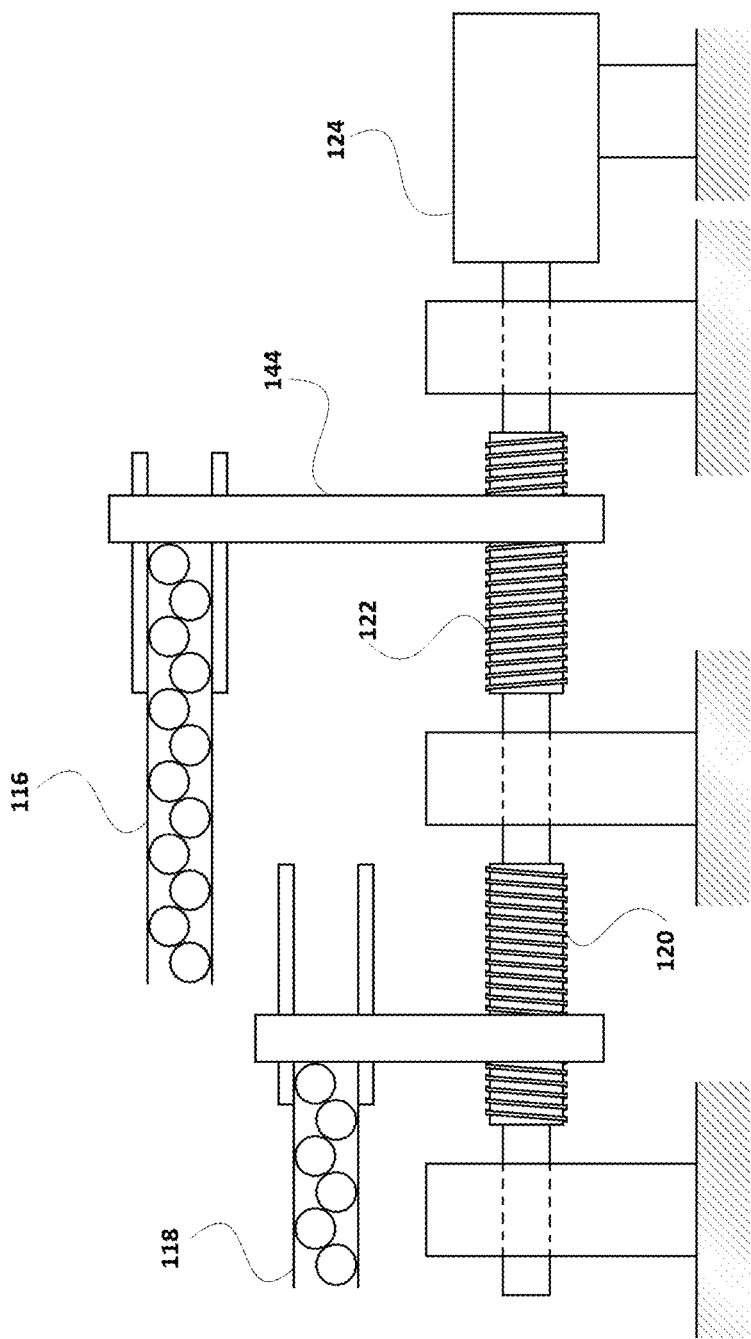
FIG. 17A illustrates a single motor and mechanism for driving media in two different lines in opposite directions.
Figure 17B:
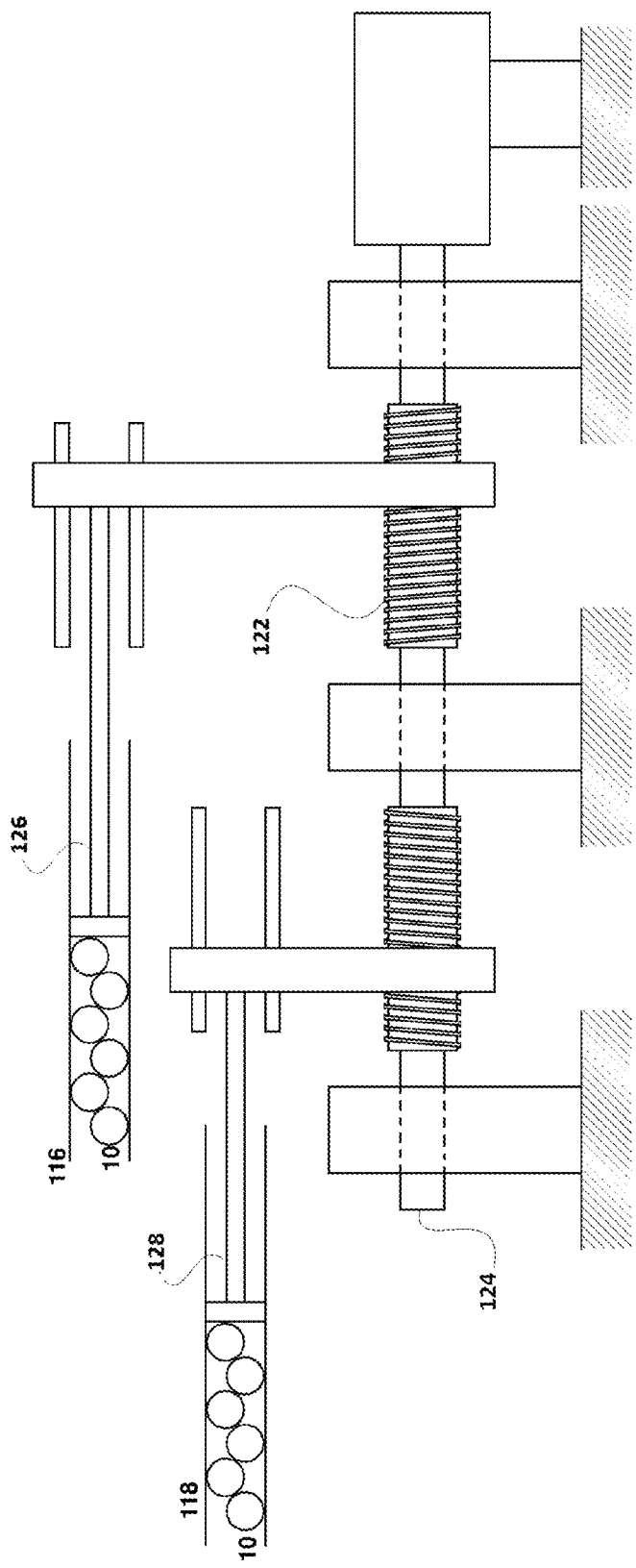
FIG. 17B illustrates a single motor driving media in two different lines in opposite directions with a piston in each line.

FIG. 17A shows that lines 116 and 118 move in opposite directions when the system is powered by motor 124. The opposite movement is provided by gearing shafts 120 and 122 to rotate in opposite directions. FIG. 17B illustrates a similar system to FIG. 17A, but also includes pistons 126, 128 which power the movement of spheres 10 in the lines 116 and 118.

Figure 18B:
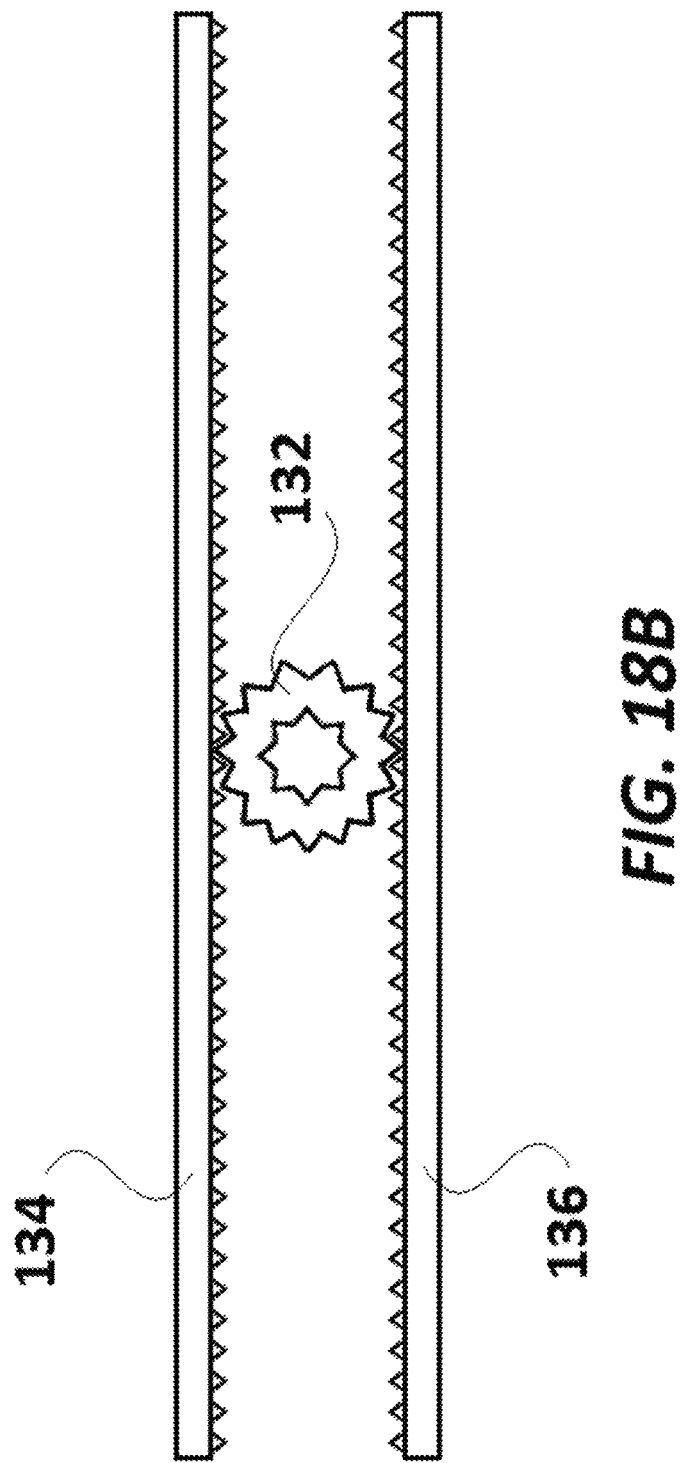

FIG. 18A depicts a hydraulic force multiplier system, wherein piston 130 acts on fluid in chamber 131 to multiply the force exerted on spheres 10 and spacers 18 from the left of piston 130. FIG. 18B depicts gear 132 used to power pistons 134 and 136. The gearing ratio on the mating gear surfaces can be used to multiply the force from gear 132 exerted on the pistons 134 and 136.

Figure 19F:
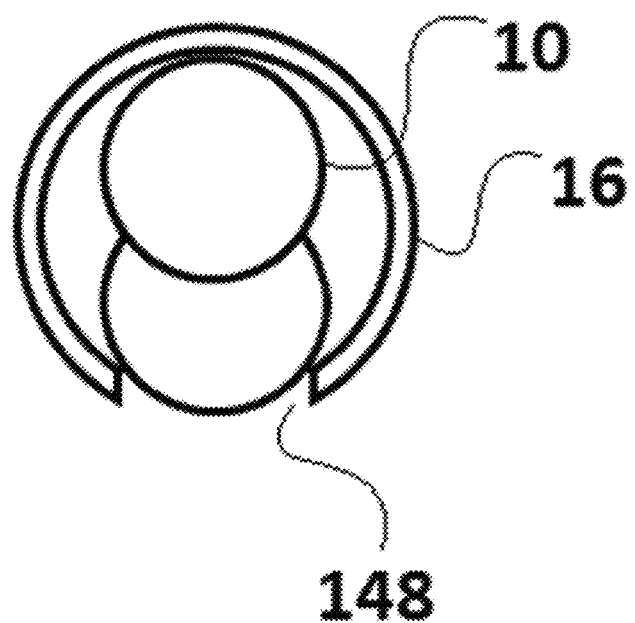

FIGS. 19A to 19C show cross-section of lines 16 with solid media 10 therein, to depict longitudinal inserts 140 inside the lines 16 in FIGS. 19A and 19C which aid in holding spheres 10 in place. Longitudinal channels 146 in FIG. 19C allow pressure equalization inside line 16 with the ambient pressure. This can be especially useful for deep sea applications. FIG. 19D shows slots 144 in the wall of line 16 to aid in holding spheres 10 in place. FIG. 19E depicts longitudinal inserts 148 which can house electrical power lines for motors in the system. FIG. 19F depicts spheres 10 being guided in line 16 using a single opening 148.

Figure 20A:
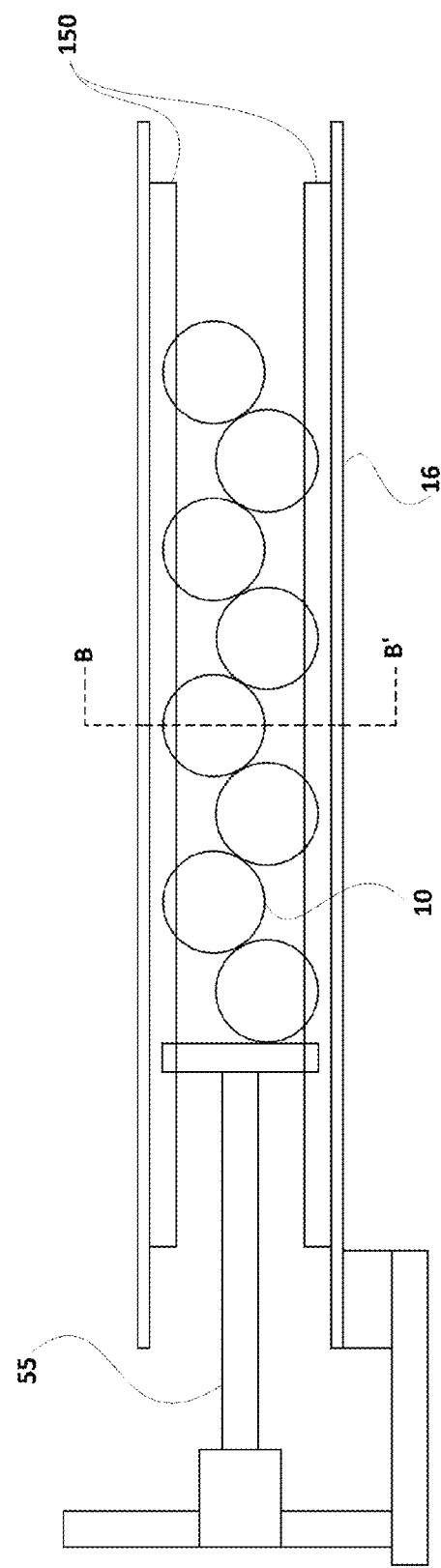
FIGS. 20A and 20B depict a channel composed of four rectangular bars, which are surrounded by a cylindrical line.
Figure 20B:
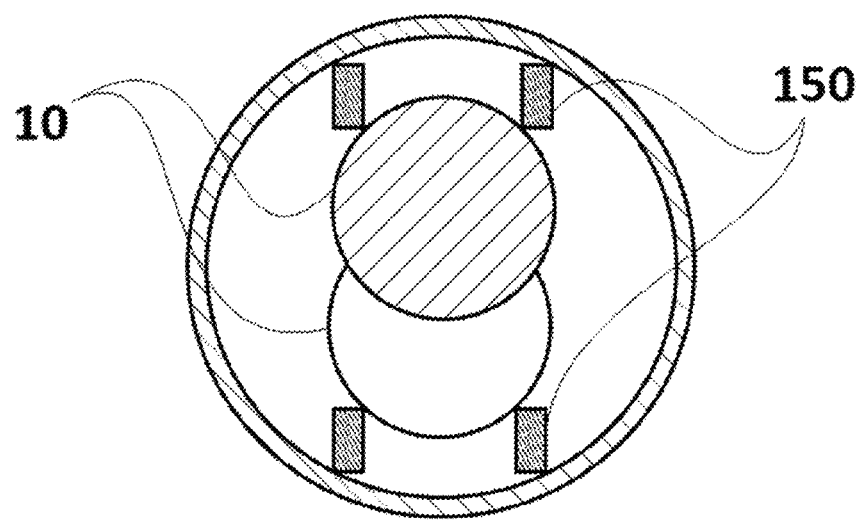

FIG. 20A shows rectangular-shaped longitudinal inserts 150 holding spheres 10 inside line 16. FIG. 20B shows the cross section of FIG. 20A along the line B-B.

Figure 21A:
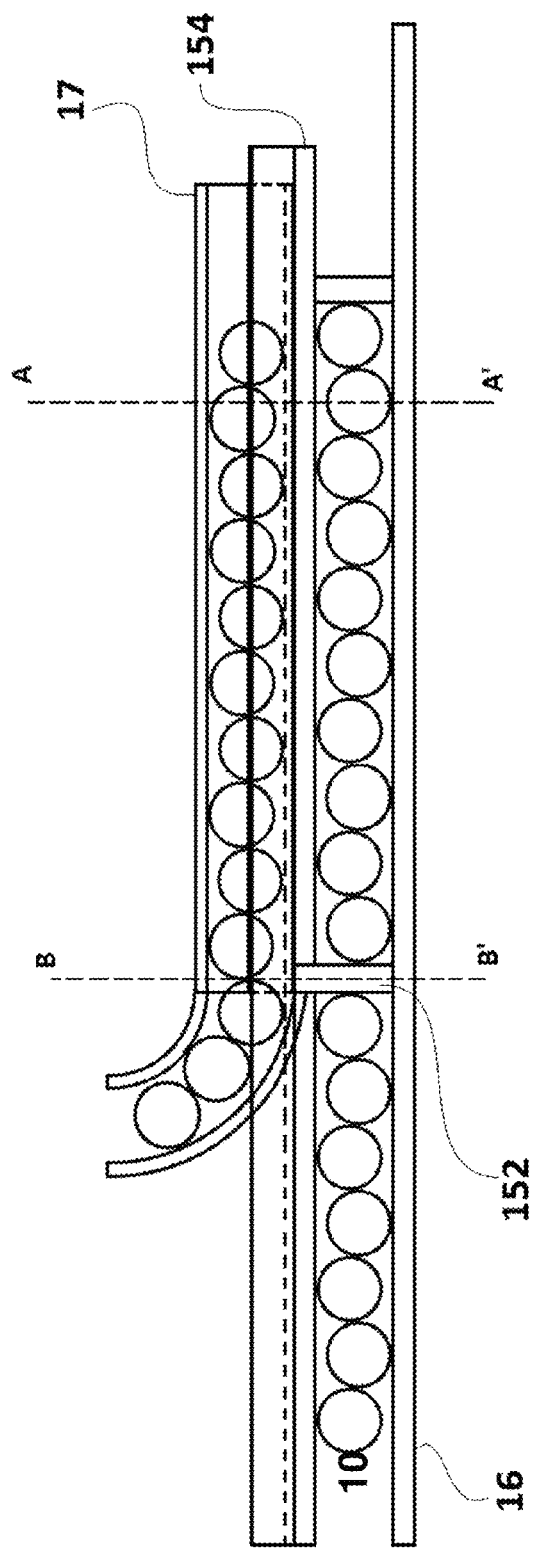
FIGS. 21A to 21J depict a mechanism for actuation of two units with two solid media channels, where the channel of the solid-media path of the second channel includes a substantially orthogonal bend to the path of the first channel.
Figure 21D:
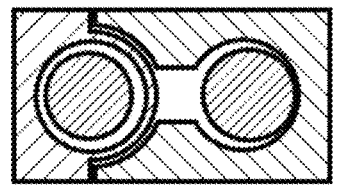
Figure 21C:
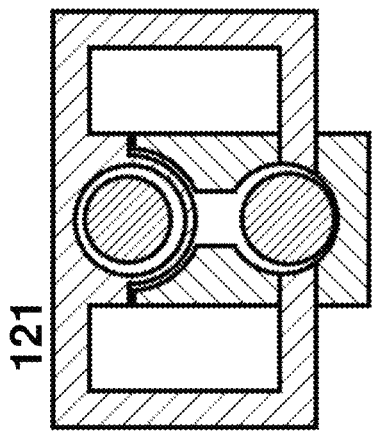
Figure 21B:
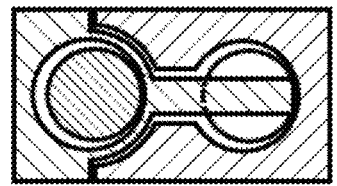
Figure 21E:
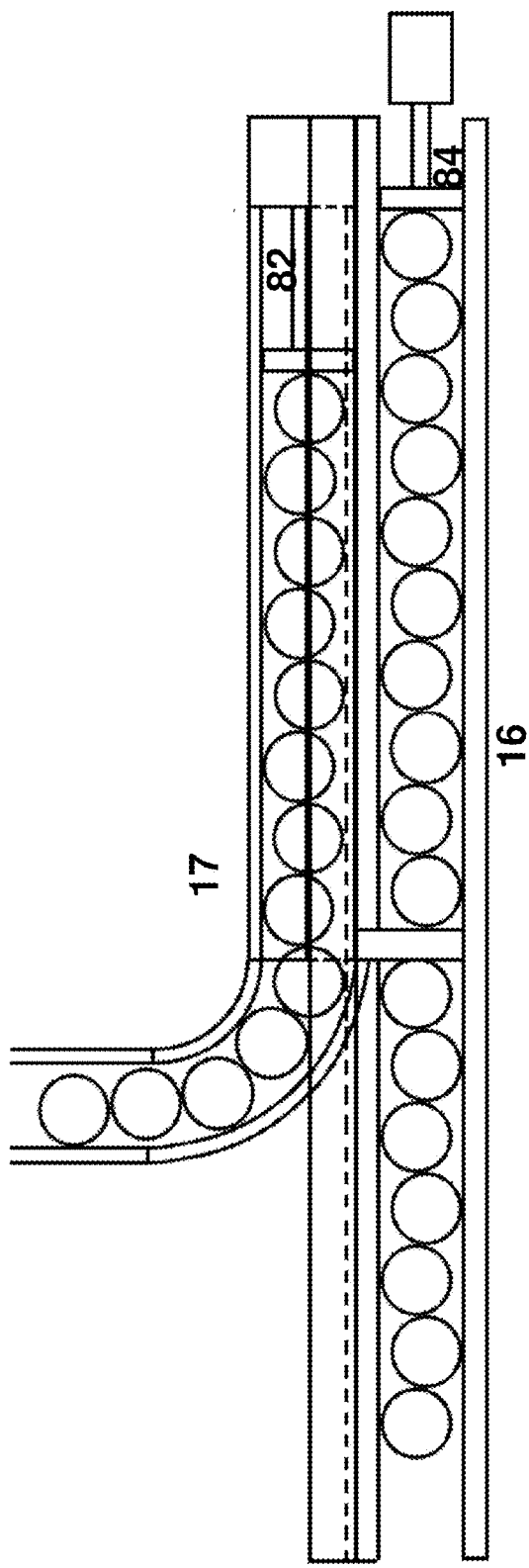
Figure 21F:
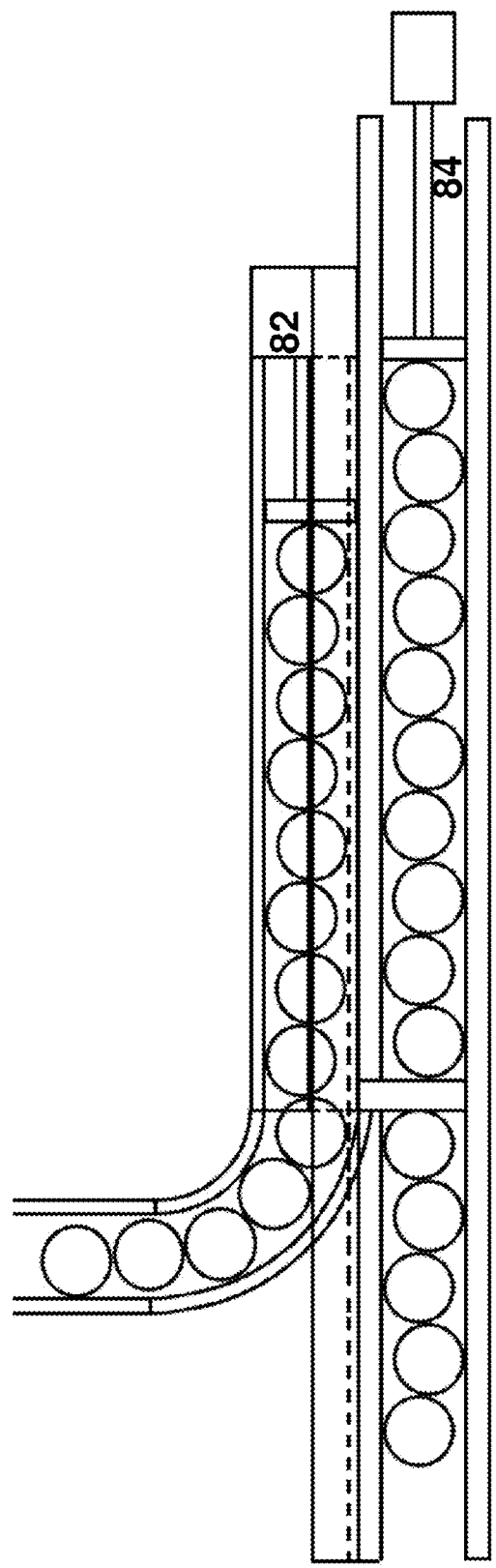
Figures 21G, 21H:
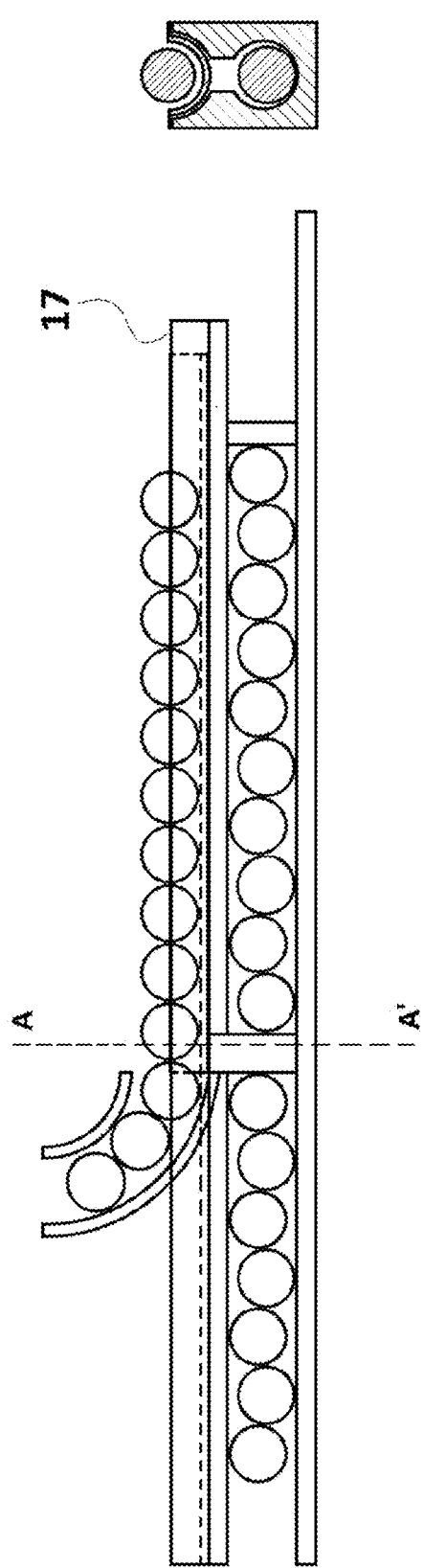
Figure 21I:
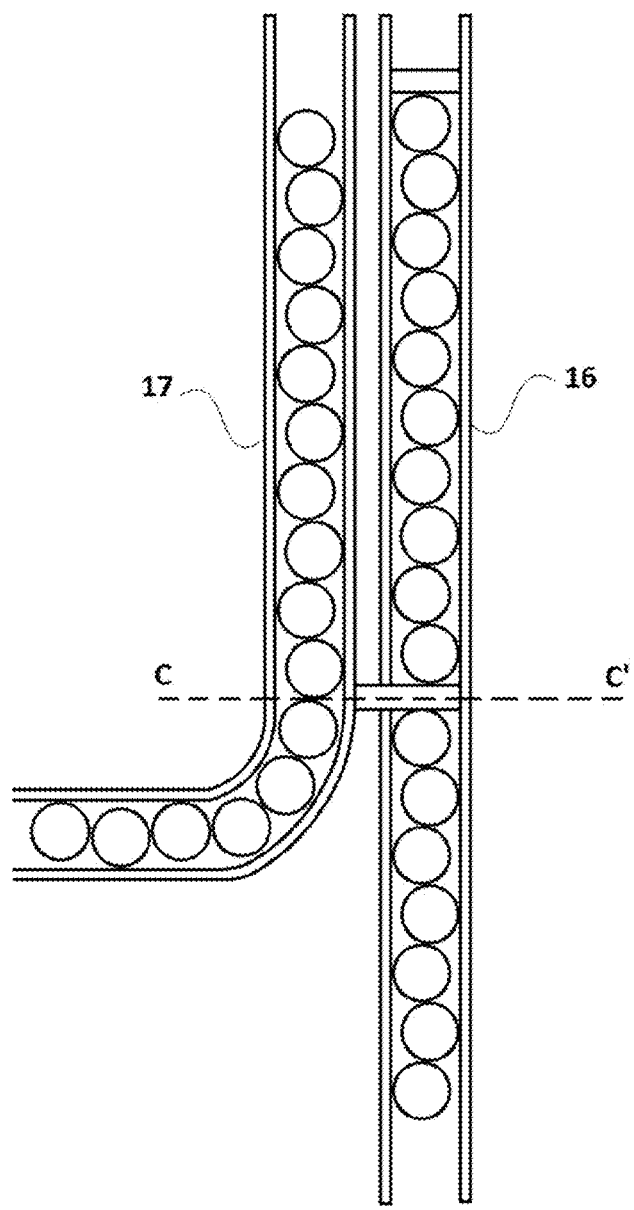
Figure 21J:
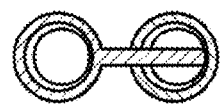

FIGS. 21A and 21B (sectional view along lines B-B) depict lines 16 and 17 filled with spheres 10, with line 17 atop 16, and including a scooping mechanism 152 which moves along a slot 154 in both lines 16 and 17. The mechanism 152 is pushed by spheres 10 in line 16 to a desired position, then stopped. At the stop points, spheres 10 are routed from line 16 up into line 17. The uppermost exit of line 17 can feed another line (not shown) for the spheres 10 to enter. FIG. 21C is a sectional view of a similar device but depicting a connection 121 between the upper and lower portions of mechanism 152 which runs outside of lines 16 and 17. FIG. 21D depicts a sectional view along lines A-A of FIG. 21A. FIGS. 21E and 21F depict the pistons 82, 84 pushing spheres 10 and extended by varying amounts to change the location of upper line 17 relative to lower line 16. FIGS. 21G and 21H depicts another similar mechanism to that in FIGS. 21A to 21F, with a one-half channel instead of a closed upper line 17, but with otherwise analogous portions. FIGS. 21I and 21J depict another similar arrangement to that in FIGS. 21A to 21F, but having the lines 16 and 17 lying side-by-side instead of one atop the other.

Figure 22A:
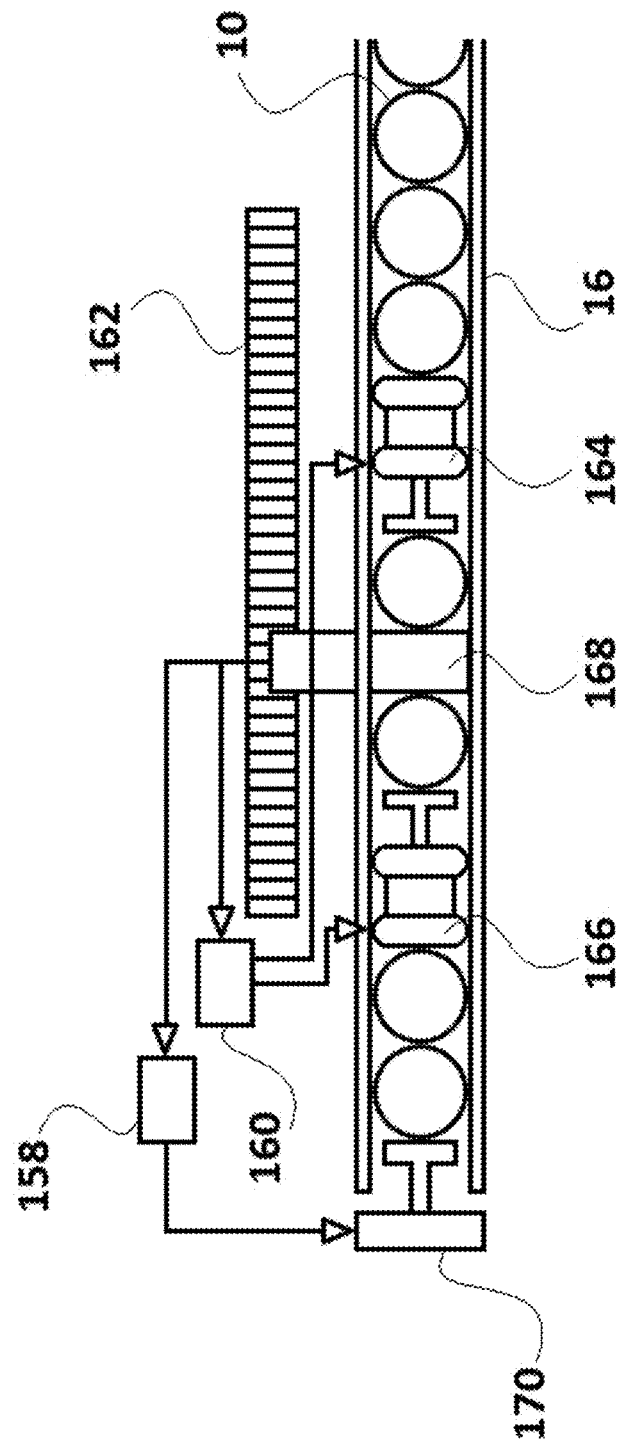
FIG. 22A illustrates use of two motors controlling respectively one of two drivers, where one driver is for larger movement control and the other controls fine tuning drivers, in a first position.
Figure 22B:
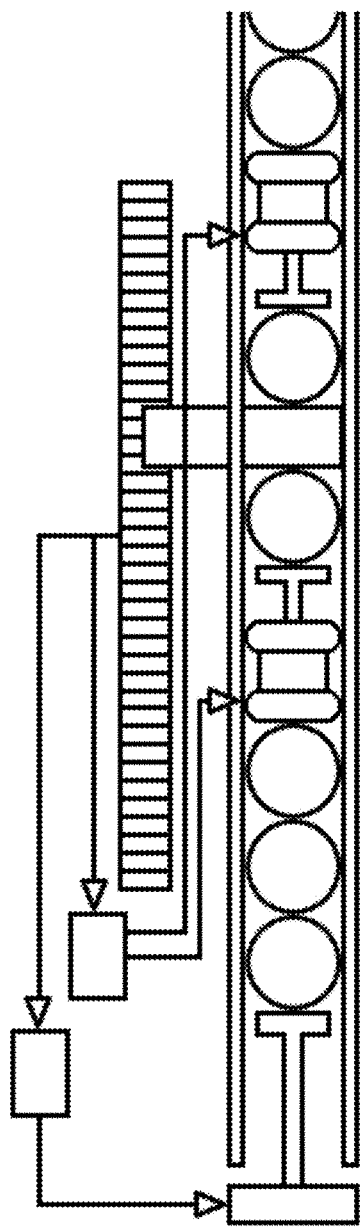
FIG. 22B illustrates the drivers of FIG. 22A in a second position.
Figure 22C:
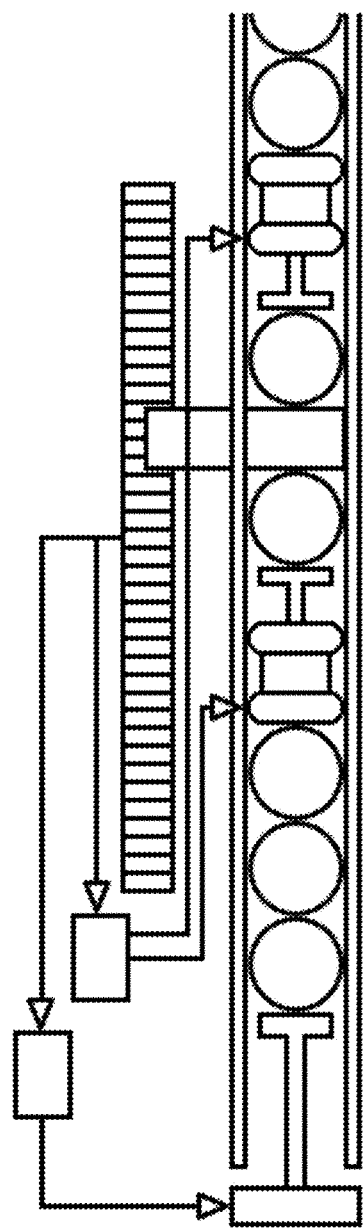
FIG. 22C illustrates the drivers of FIG. 22B in a different position.
Figure 22D:
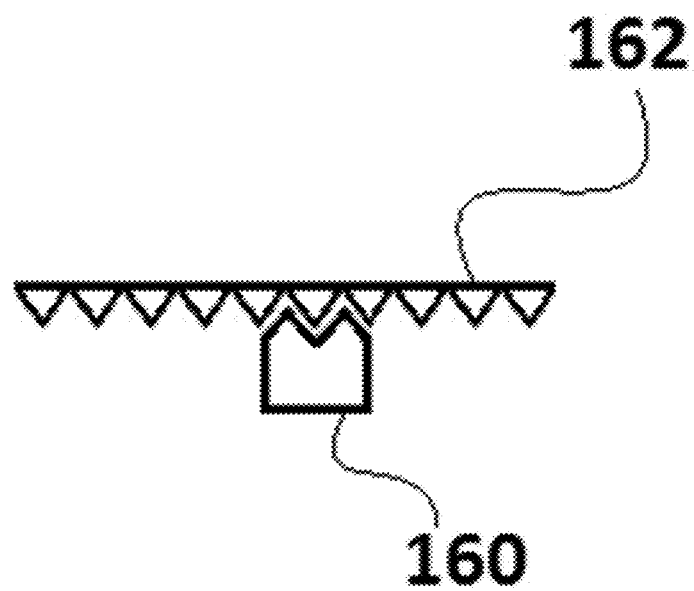
FIG. 22D is an enlarged view illustrating one aspect of the movement control, which is mating teeth.

In FIGS. 22A to 22C, a system which allows fine-tuning of the position of the spheres 10 (and therefore, any instrument attachment) using two motors, 158 and 160, where motor 158 powers the piston of main driver 170, and motor 160 powers internal piston-drivers 164, 166 (which move inside line 16 with the spheres 10). Main driver 170 ratchets member 168 along the horizontal bar 162 to near a desired position. Then drivers 164, 166 are actuated sequentially in order to guide the member 168 more precisely to the desired position. FIG. 22D shows the cross section of the mating of member 168 and bar 162. The system allows the drivers 164, 166 to position member 168 to a position between the mating portions of the teeth 161, 163.

Figure 23A:
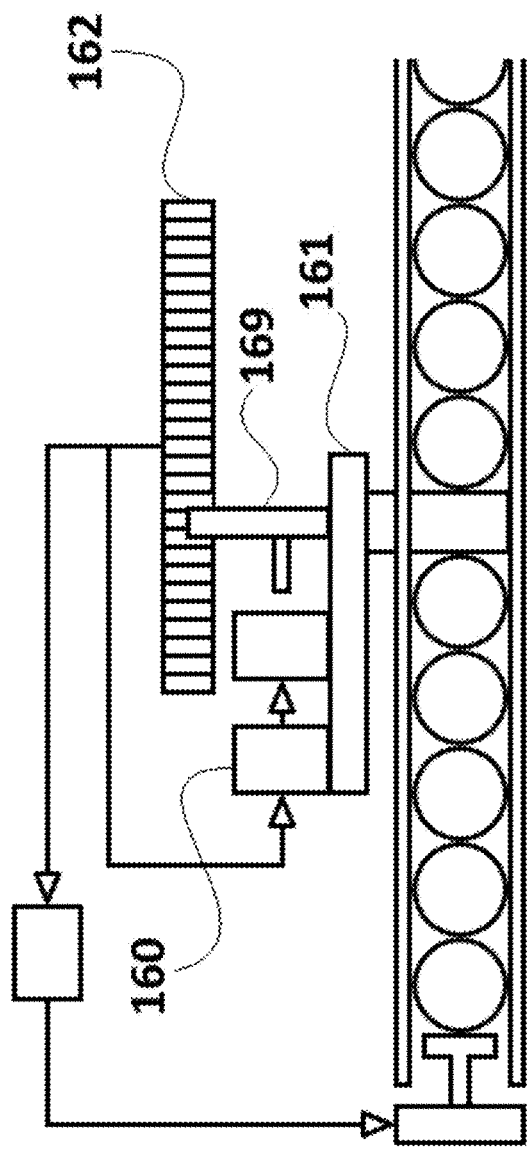
FIG. 23A illustrates a related but alternative arrangement of pistons and motors from that in FIGS. 22A to 22C.
Figure 23E:
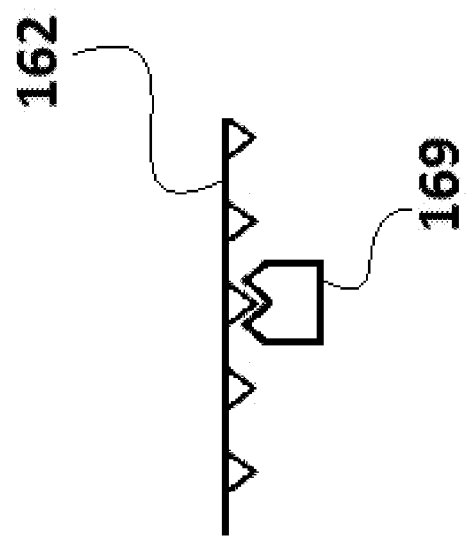
FIGS. 23D and 23E illustrate two different sets of interlocking teeth which can both be used to control coarser and finer movements in the arrangements of FIGS. 23A-23B.
Figure 23D:
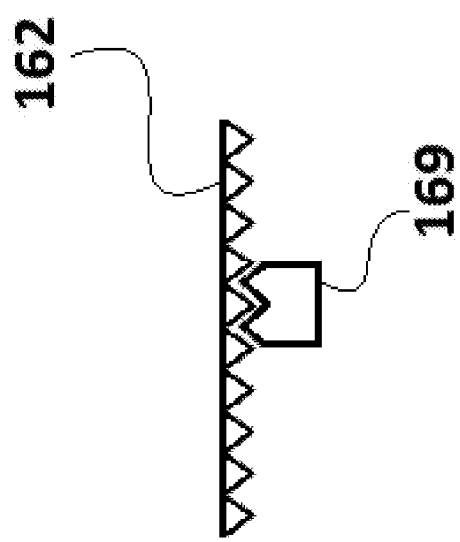

FIGS. 23A and 23B show a similar system to FIGS. 22A to 22D, except that motor 160 sits atop platform 161 which is attached to member 169 which ratchets along horizontal bar 162 to near a desired position. Driver 170 is used first for positioning, then 160 is actuated for finer movement control or to position the member 169 between the larger set of teeth (171 in FIG. 22D) and/or where another finer set of teeth 173 are in mating position.

Figure 24:
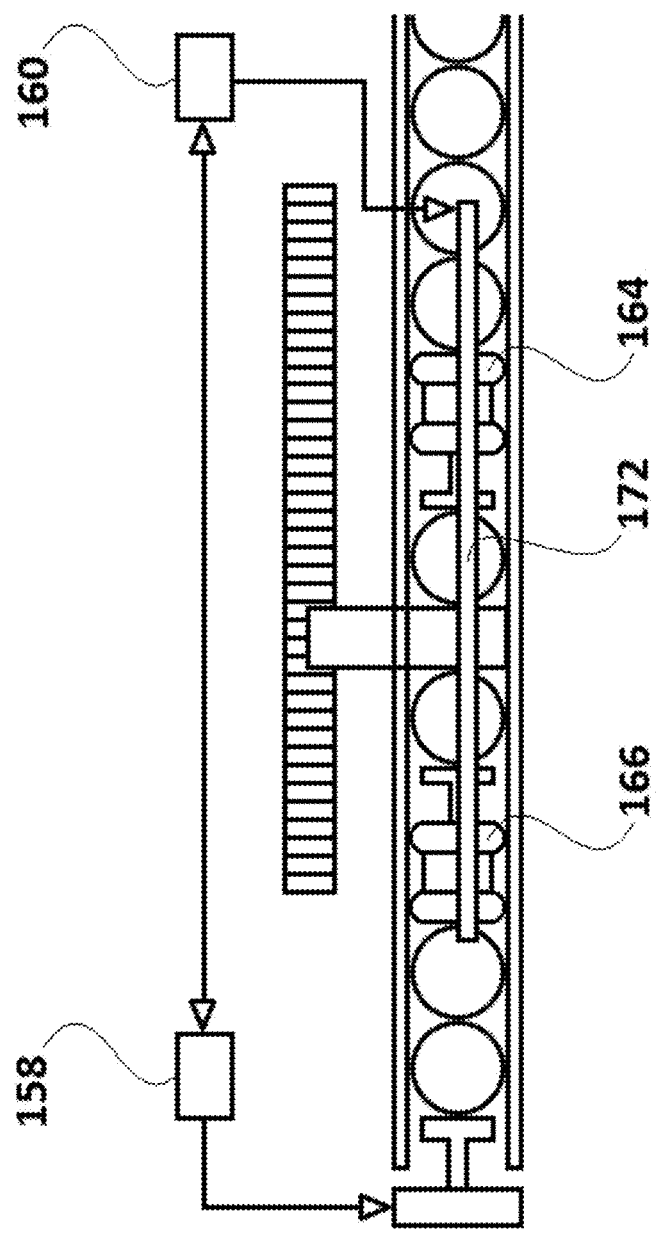
FIG. 24 illustrates a similar arrangement to that in FIGS. 22A-23C, but using a power source for the motor which lies inside the line.

FIG. 24 is similar to FIGS. 22A to 22C, but a power rail 172 provides power to drivers 164, 166. FIGS. 25A and 25B are also similar except that a docking re-charger station 174 is included. Motor 164 is shown in charging position at station 174 in FIG. 25B.

Control of movement of the spheres in the devices shown in FIGS. 22A to 25B is through multiple motors, as noted. To guide the final position of the spheres in the lines by positioning, e.g., member 168 in FIG. 22A and the analogous members in other figures, the movement of the spheres or of member 168 must be detected, fed back to a controller, and the information used to power further positioning steps. A number of mechanisms can be used for the positional location including the diode arrays of FIGS. 26A to 26F, or a sensor system located at intervals along the axis of line 16.

Figure 26A:
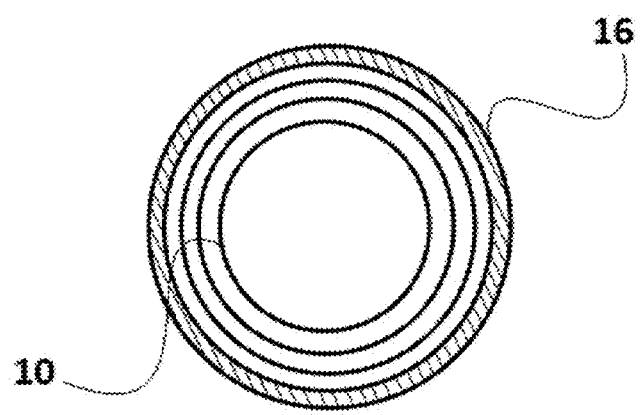
FIG. 26A depicts locating the position of solid media in the line as the media advances through the line, using a sensor system as shown in FIG. 26B.
Figure 26B:
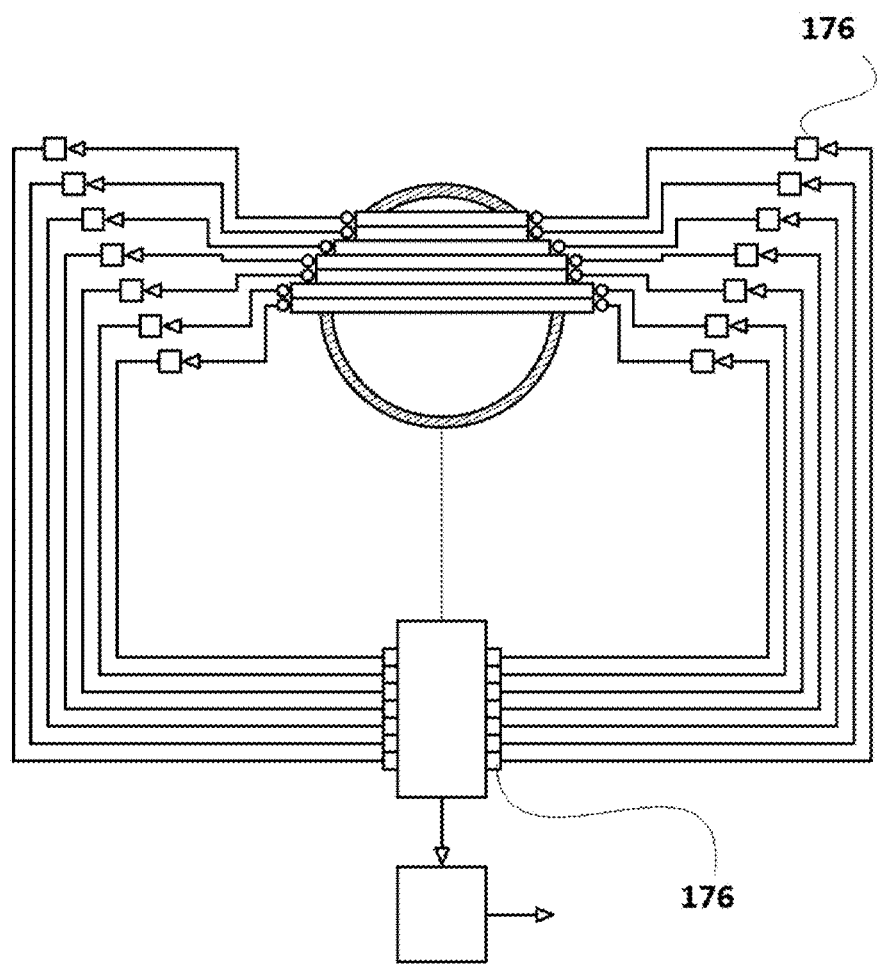
FIG. 26C shows a first distribution of the sensors relative to the axis of the line.
FIG. 26D shows another distribution of the sensors.
FIG. 26E shows distribution of three arrays of sensors.
FIG. 26F shows distribution of multiple arrays of sensors.
Figure 26F:
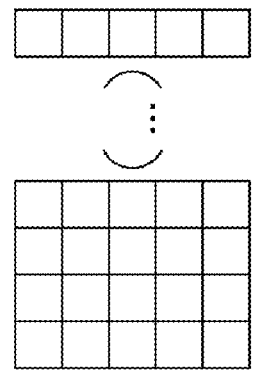
Figure 26E:
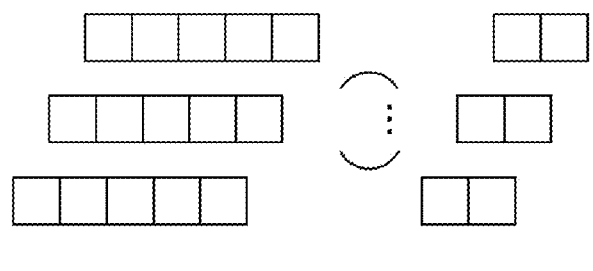
Figure 26D:
Figure 26C:
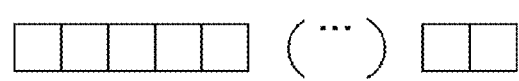

FIG. 26A is a sectional view of the view of a sphere 10 inside line 16 as illuminated by diode array 176. FIG. 26B is an exploded view of the lighting components of diode array 176. FIGS. 26C to 26E show some possible arrangements of lights in array 176. FIGS. 26E and 26F display panels of diodes, which could be wrapped around a section of the outside surface of line 16.

Figure 27A:
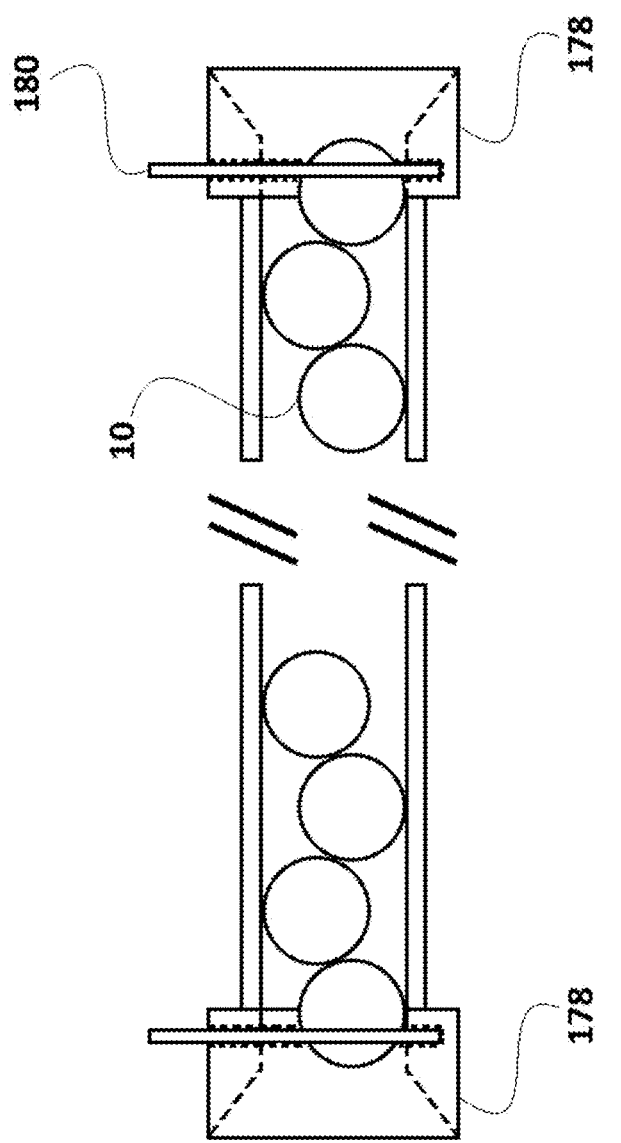
FIGS. 27A-27E illustrate a section of the line with connectors at its ends, and blocking units to contain the media.
Figure 27B:
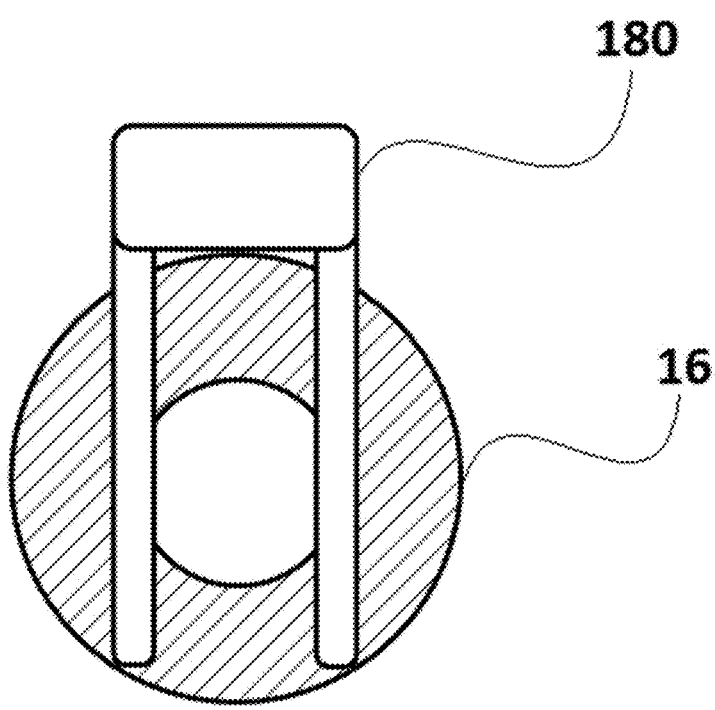
Figure 27C:
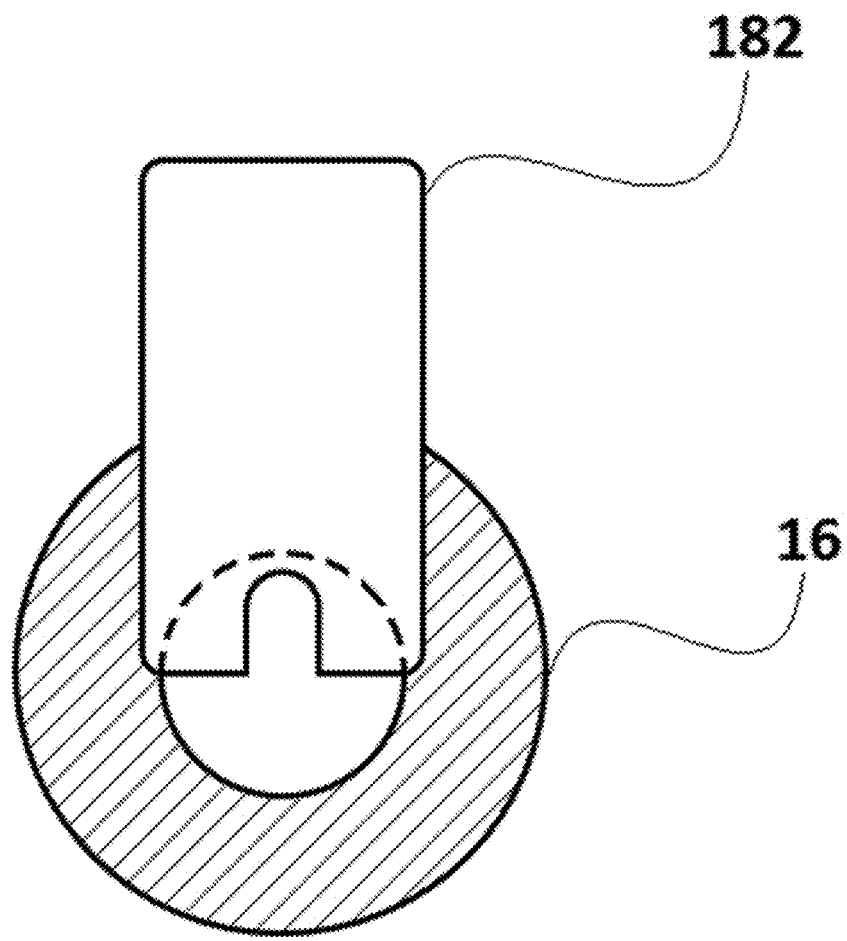
Figure 27D:
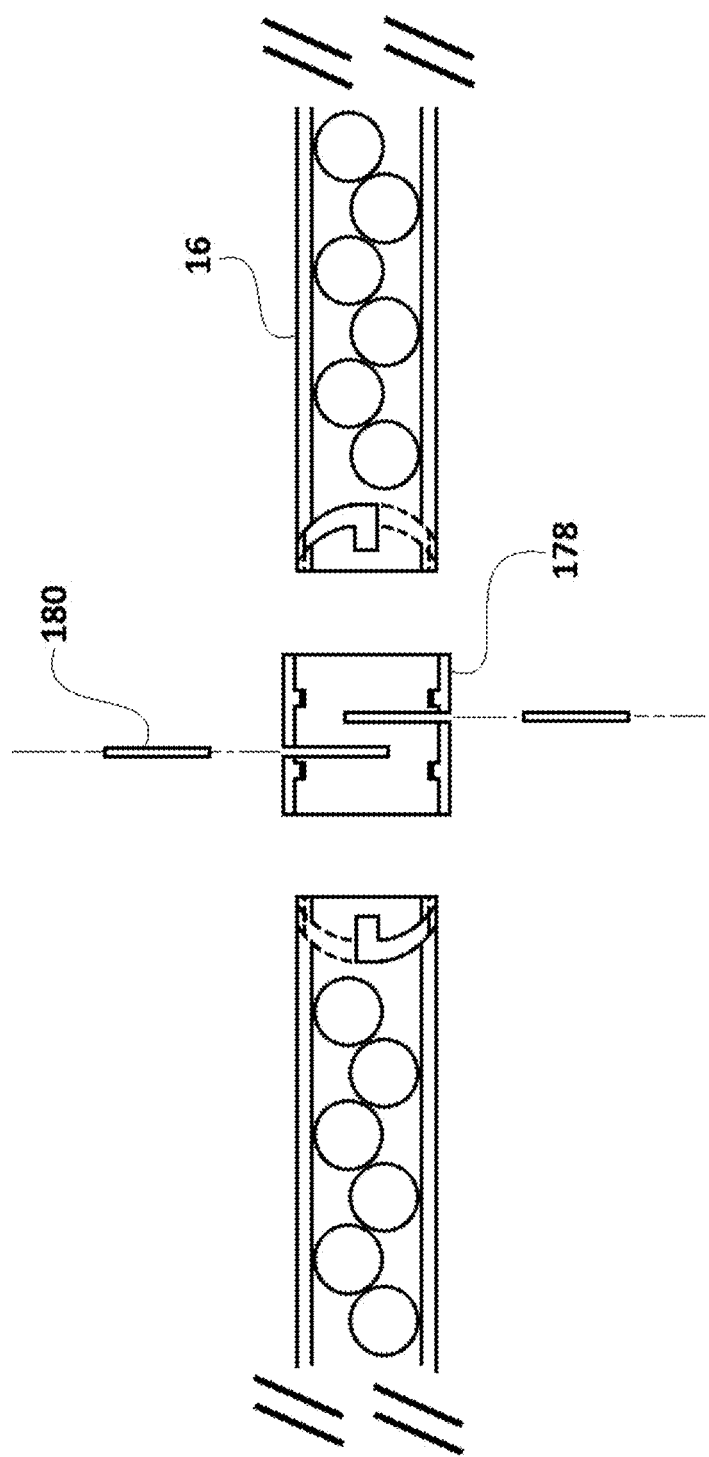
Figure 27E:
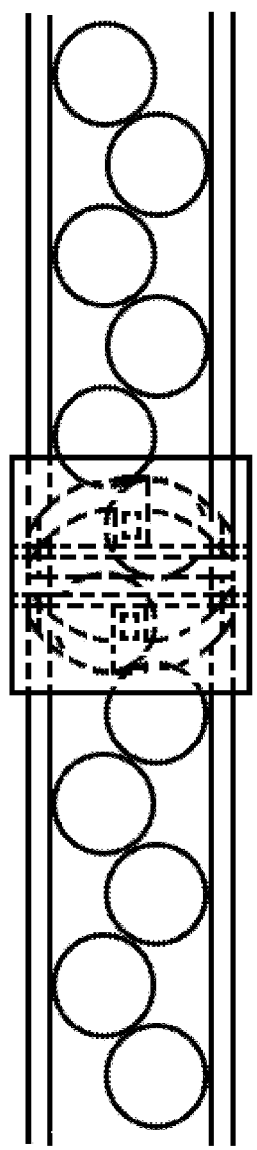

FIGS. 27A to 27D show mating end connectors 178 which twist-lock to an adjacent fitting, and blocking insert 180, which can obstruct travel of spheres 10 in line 16. Another type of blocking insert 182 is shown in FIG. 27C. FIG. 27D shows two connectors 178 locked together with insert 180 removed. Spheres 10 can freely move in line 16 after removal of insert 180.

Figure 28:
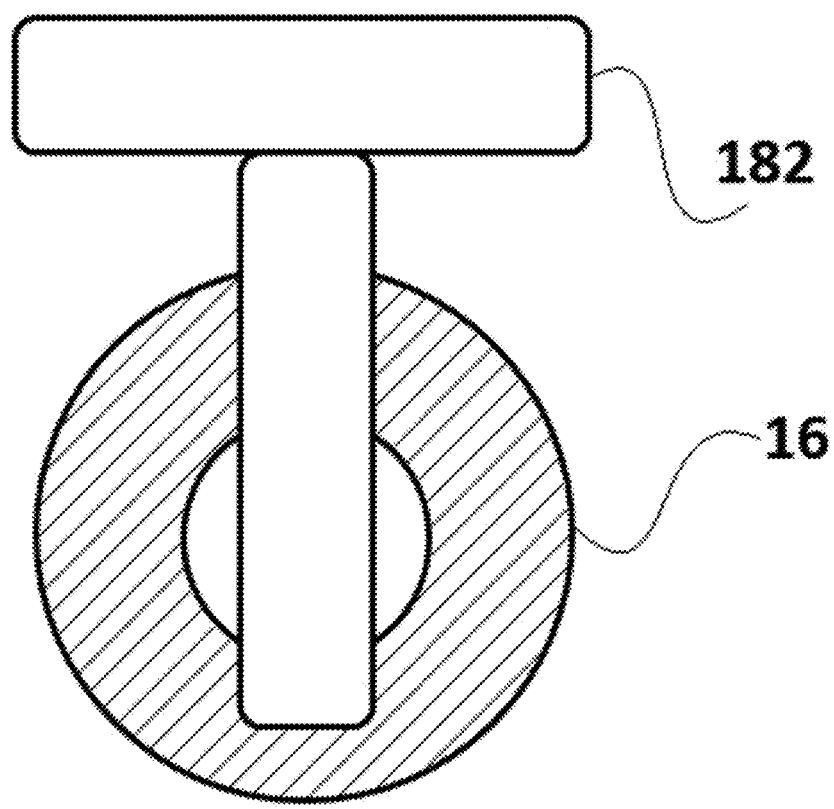
FIG. 28 illustrates another type of channel blocker, similar to FIGS. 27A to 7C.
Figure 29A:
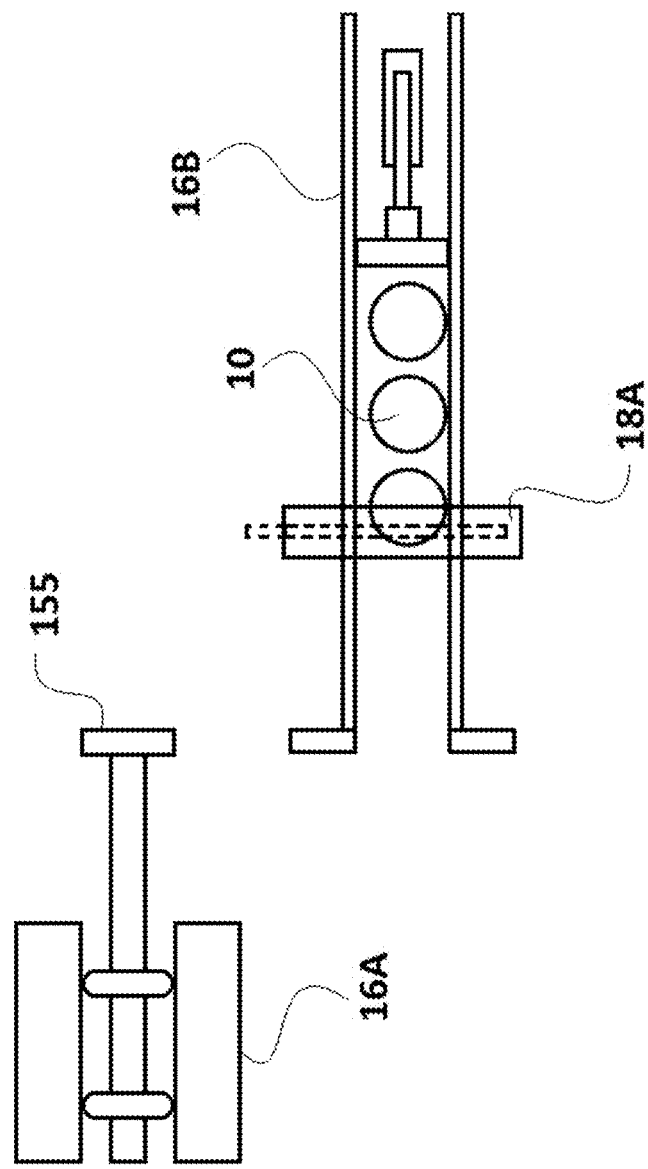

FIG. 28 illustrates another single-leg type of line 16 blocker, labeled 182. Blocker 182 is also removable. In FIGS. 29A to 29C, two sections of a line (16A, 16B) are joined, and then blocking insert 186 is removed after the joining. Piston 55 can push the spheres inside line 16 with the blocking insert 186 removed.

Figure 30A:
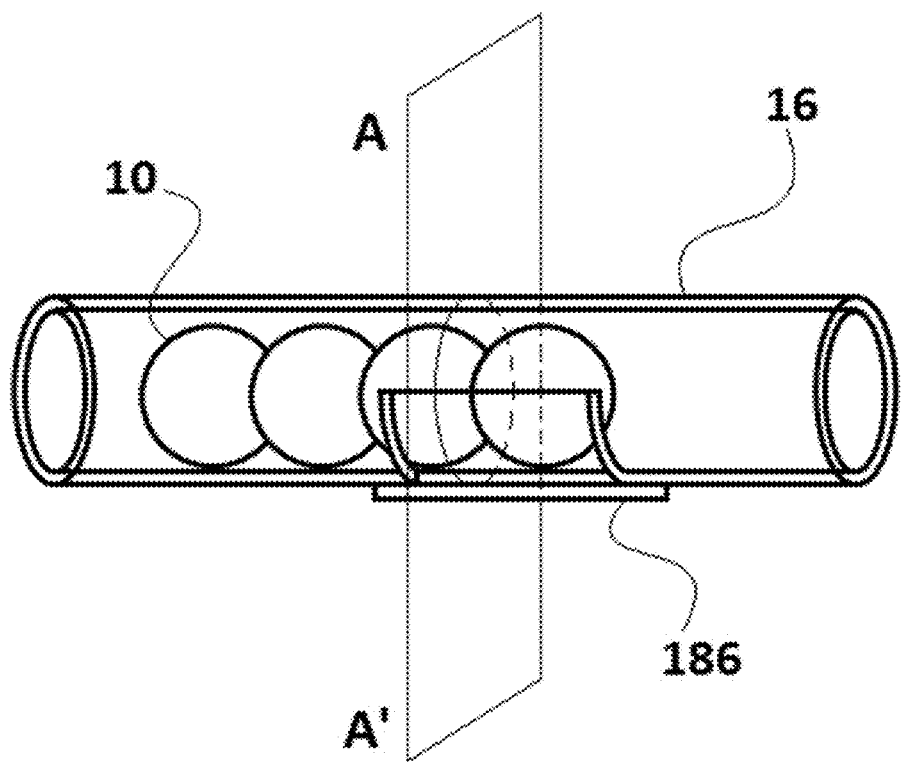
Figure 30B:
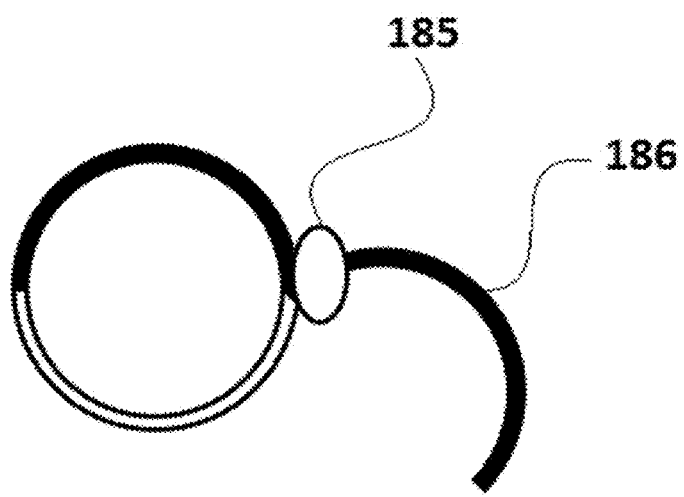
Figure 30C:
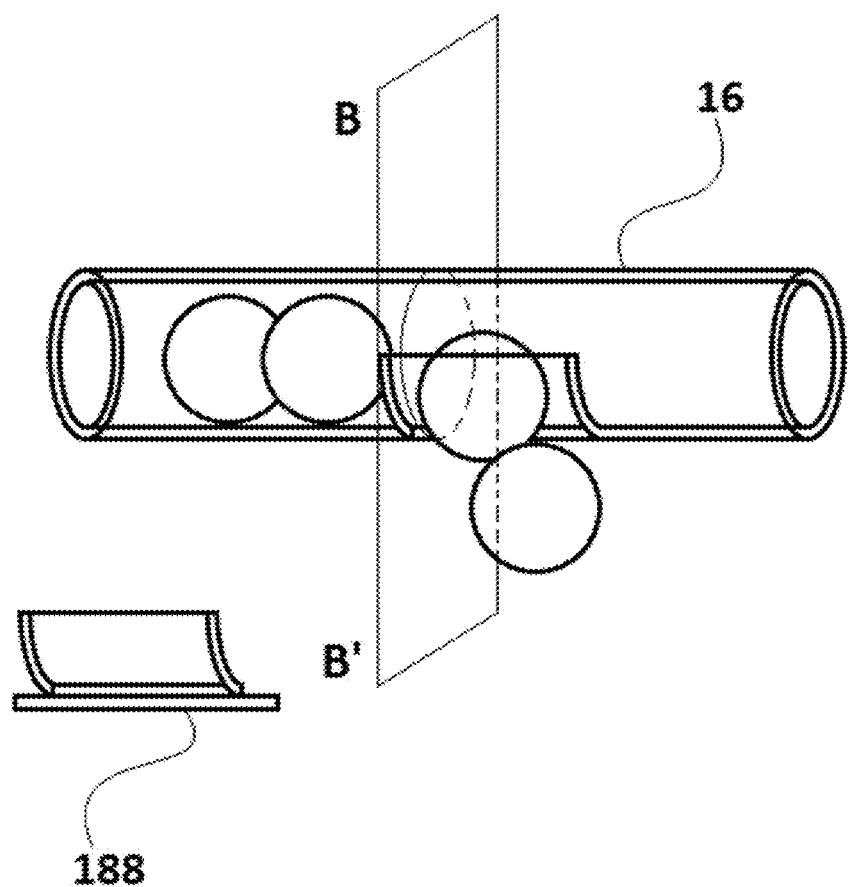
Figure 30D:
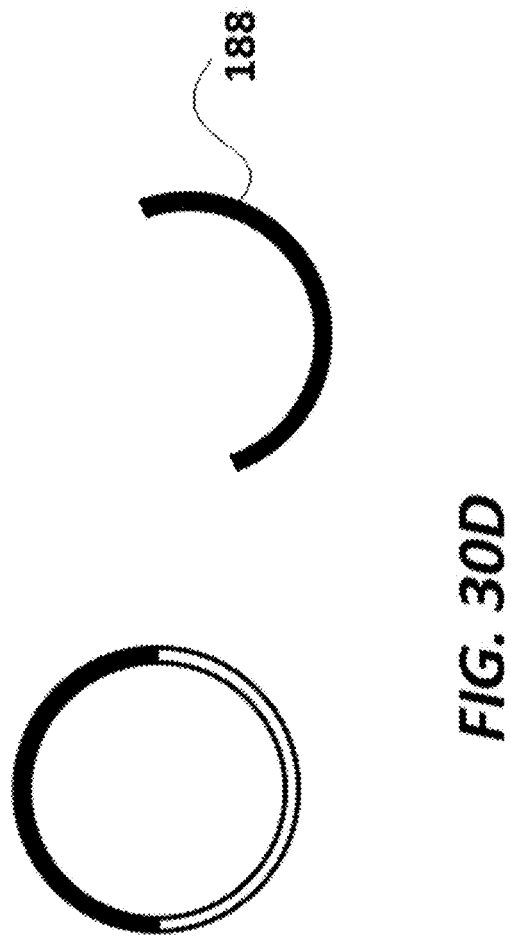

FIGS. 30A to 30F illustrate release mechanisms for spheres in line 10. In FIGS. 30A and 30B, a hinged door 186 can swing open to release spheres 10 on hinge 185. FIGS. 30C and 30D illustrate a removable door 188 which can open to release spheres 10.

Figure 30E:
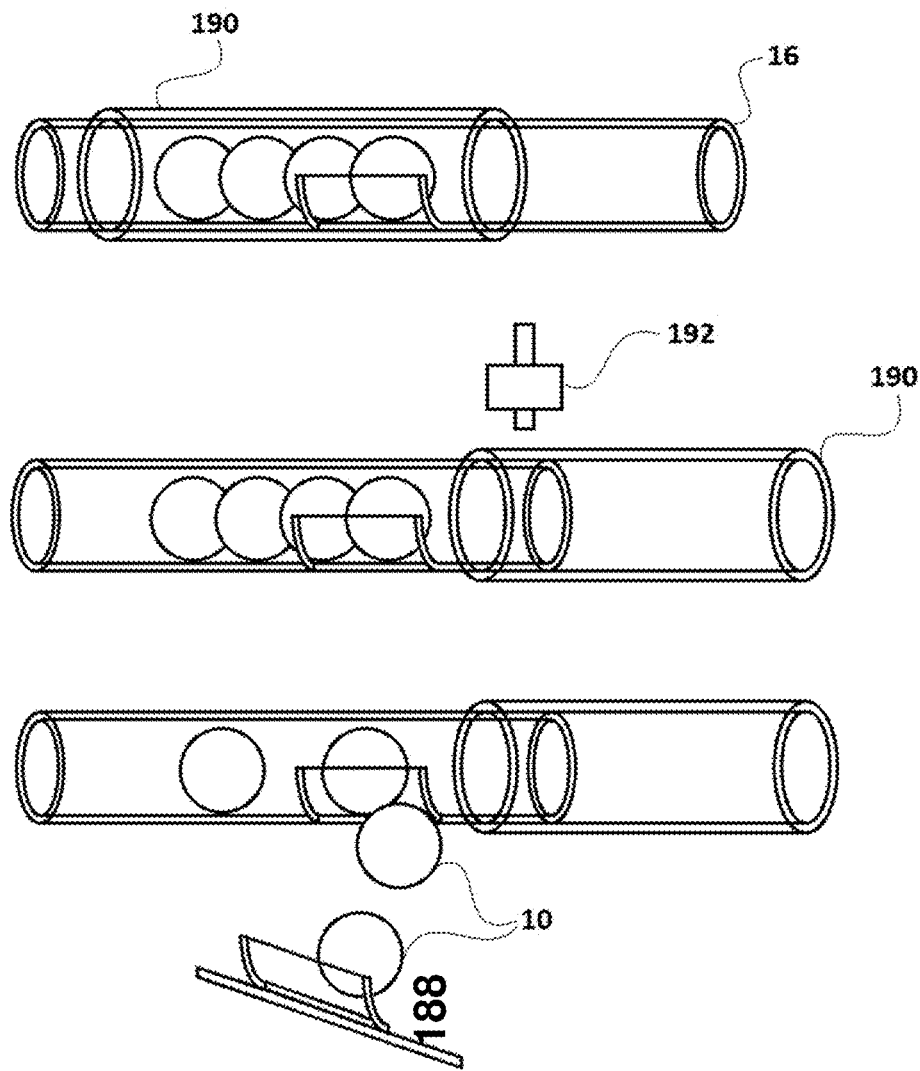

FIG. 30E illustrates a sleeve 190 around line 16, where sleeve 190 can be moved to the right manually or by actuator 192, whereupon door 188 falls open to release spheres 10.

Figure 30G:
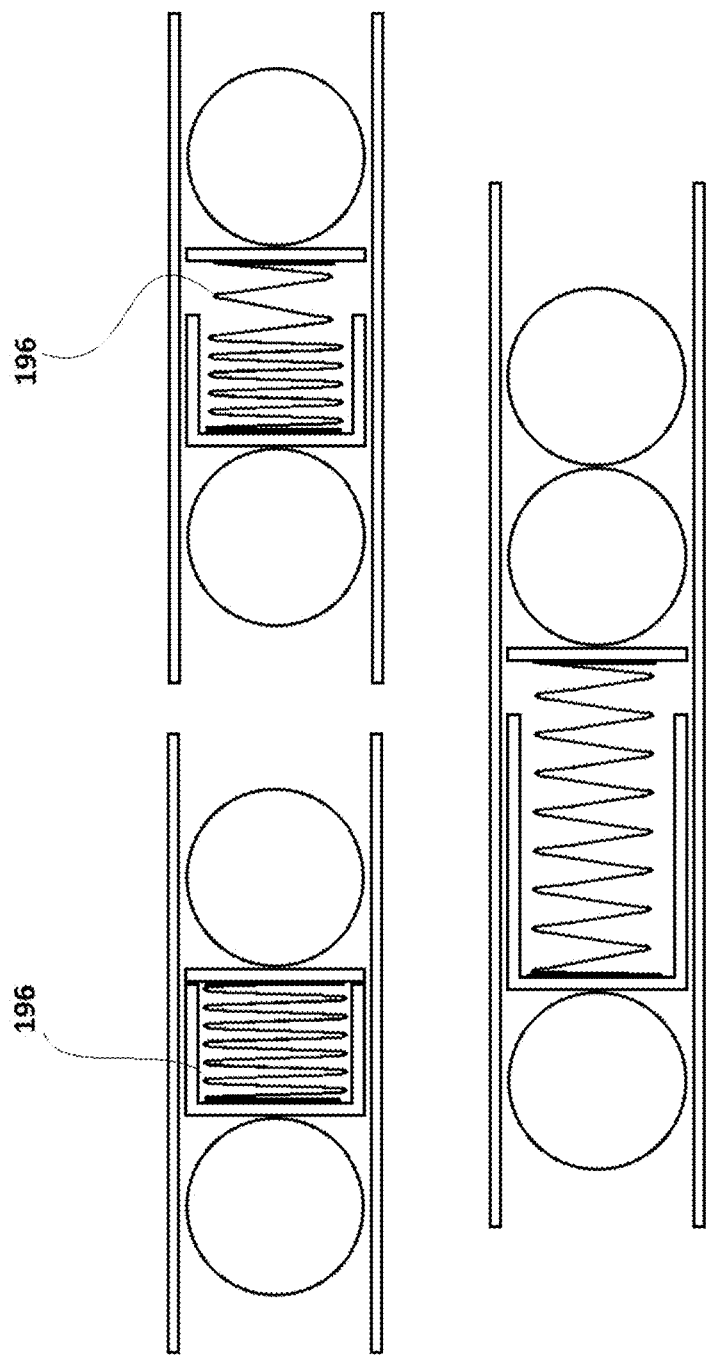

FIG. 30F schematically illustrates that line 16 can include sections which are normally connected (upper panel), but can be disconnected and opened to release spheres 10 and spacers 18. A movable blocking member 194 can be moved manually or under automatic actuation left to right in slot 192 to effect clearance of line 16. FIG. 30G illustrates that a spring-loaded mechanism 196 can be used, where the spring assists in clearance (instead of moving blocking member 194 as in FIG. 30F).

FIG. 31 is a plan view of a carriage 200 with a set of screws 202, 204 which can be adjusted to align the axis of carriage 200, or to set its position. Carriage 200 also includes self-aligning linear ball or flanged sleeve bearings 206.

FIGS. 32A and 32B show piston 55A held by supports 212 and guided by bearings 214, which acts on piston 55B. Piston 55B is held by supports 210 and guided by bearings 208, and acts on spheres 10. Flexible tubing 16 includes rigid sleeve 216, to hold tubing 16 aligned with piston 55B. Mobile block 218 is affixed to and moves with piston 55A on bearing 220, to provide support during travel of piston 55A. A similar support system (not shown) may be used for piston 55B. FIG. 32A shows the pistons in a starting position and FIG. 32B shows the pistons in a final position.

FIGS. 33A and 33B show a system which can be used with the system of the invention for neurosurgery. A patient's head 222 sits between (or can be screwed to) posts 224. Supports 228 include a rotating hinge where they attach to carriage 226. Supports 228 rest atop supports 230. Lines 16 housing solid media (not shown) extend through supports 230. FIG. 33B shows that carriage 226 can rotate on the hinges through an angle of at least about 110 degrees.

Figure 34A:
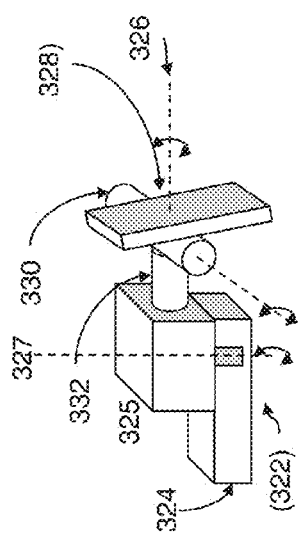
FIGS. 34A to 34C illustrate mechanisms compatible with the system of FIGS. 33A and 33B for fine control of an instrument.

FIG. 34A shows instrument platform 322, with plate 328 for holding a surgical instrument. Plate 328 can rotate on axis 326 of member 332, or on the axis of member 330, to allow multiple degrees of freedom to manipulate the surgical instrument. Upper block 325 can also rotate on axis 327 with respect to lower block 324. Lower block 324 is attached to carriage 226.

Figure 34B:
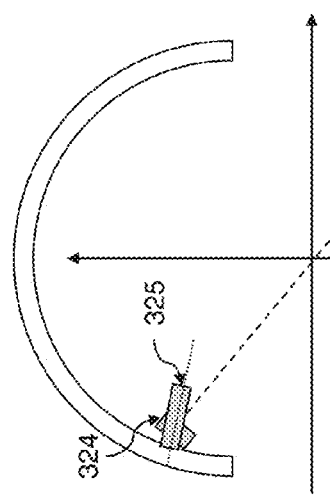
Figure 34C:
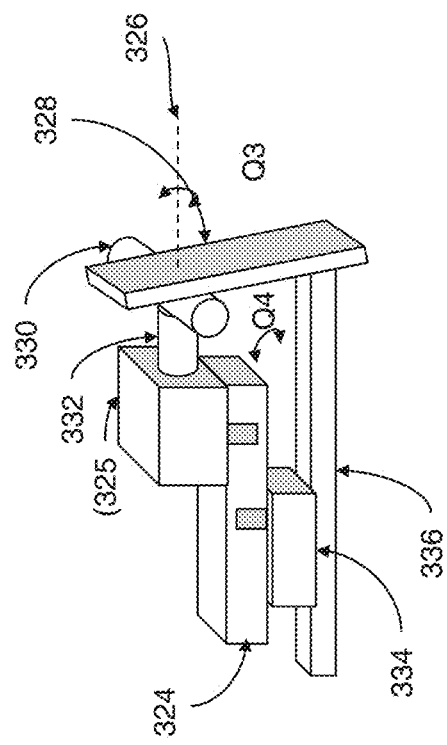

FIG. 34B shows that platform 322, attached to carriage 226 by lower block 324, rides on carriage 226 under actuation from movement of spheres 10 in lines 16 (FIGS. 33A & 33B). FIG. 34B shows that upper block 325 is rotated relative to lower block 324. FIG. 34C shows that platform 322 is further affixed to member 334, which can move left to right along rail 336 to change the angle of plate 328 (which is attached by hinges to rail 336).

FIGS. 35A to 35C shows mating fittings for lines 300, which have a locking position which locks when there is ½ turn of the lines 300 relative to each other, and which also has a first locking position which is ¼ turn of the lines 300 relative to each other. FIG. 35C is a cross section of FIG. 35A, taken along the lines A-A, showing spheres 10 held back by gate members 302. FIG. 35D shows the connector of FIGS. 35A to 35C connecting two orthogonal lines 300 and 304.

FIG. 36 depicts the position of the mating fittings in FIGS. 35A to 35D, where the fitting is rotated ½ turn to the fully closed and locked position. In this position, gate members 302 cannot block the line 304 because they cannot move past the obstruction from the mating fittings 306 and 308, as shown.

FIGS. 37A and 37B illustrate the position of the mating fittings in FIG. 36, where the fitting is rotated ¼ turn a partially closed and locked position. In this ¼ turn locked position, as shown, there is sufficient space between mating fittings 306 and 308 for gate members 302 to close on either side of spheres 10 and block the line 304 (provided spheres 10 are not too tightly packed in line 304). FIG. 37B shows the gate members 302 closed and blocking line 304.

FIGS. 38A and 38B depict a similar mating fitting as in FIGS. 36, 37A and 37B, except that line 304 now includes spacers 322 as well as spheres 10. Gate members 302 can now close and grab a spacer 322 to block line 304. Spacers 304 therefore, allow blocking of line 304 by the gate members 302 even if the spheres and spacers 322 are tightly packed in line 304.

The gate members 302 described above can close automatically, when, for example, the spheres are packed in the lines 304 too loosely. Similarly, gate members 302 can be triggered to open automatically, if the spheres are packed in the lines 304 too closely and under too much pressure. A pressure sensor can determine the inter-line pressure and automatically trigger closure when the pressure is too low, or opening when the pressure is too high.

All of the mechanisms above can be used with magnetic resonance image (MRI) guided robots for intervention procedures where at least one wired or wireless network links to a computer that has stored processor-executable instructions to operate the robot based on input from the magnetic resonance imaging system and the robot. Optionally, a plurality of contrast markers may be disposed on or around the robot to accurately register the same.

In another further embodiment the guided robot may comprise one or more imaging or non-imaging sensors internally or externally disposed in relationship to a patient's body, the sensors registrable with the robot.

Generally, the robotic system comprises an MRI-compatible robotic manipulator that can operate within the space constraints of imaging scanners, and an actuator that can operate in the very high magnetic field of the MR environment. The robotic system is useful for performing surgeries or interventions with real-time magnetic resonance imaging MRI. This technology facilitates performing the procedure with the patient inside the MRI scanner thereby offering the interventionist or surgeon the information-rich MRI data in real-time or at any point during the procedure.

Thus, also provided are imaging methods and software for the fast registration and monitoring the maneuvering of the robotic manipulator. More particularly, the robotic manipulator described herein is configured for performing procedures with real-time image guidance and in particular with magnetic resonance imaging MRI and moreover with real-time MRI. It is therefore designed to operate inside the bore of an MRI scanner while the patient resides inside the MRI scanner or any other object on which as example a simulated intervention is performed, such as a phantom, or in vivo on an animal model or ex vivo on a tissue sample. Within this context, intraoperatively real-time MRI is used to guide the operator to maneuver the robot and perform the particular procedures. As such preoperative images collected with MRI or other imaging modalities, such as, but not limited to computed tomography CT or positron emission tomography PET or ultrasound US, can be used preferentially to further enhance the information available for guiding the robot assisted procedure.

Moreover, intraoperatively, the robotic manipulator carries on its end-effector additional sensors to collect local information about the pathology, morphology and function of tissue to supplement real-time MRI. Those imaging or non-imaging sensors preferentially provide information about the pathology of tissue unavailable by conventional real-time MRI, such as assessment of the molecular signatures of cancer, and/or with higher specificity or signal sensitivity. Such examples of Intraoperative sensing are, but not limited to, ultrasound (US), optical spectroscopy, optical imaging (such as optical coherence tomography), MRI with micro-coils, tactile or haptic sensing, or video. The robotic manipulator functions as the means to co-register all of the different modalities or sensors. This is enabled because the location of the sensing element and, thus, of the interrogated tissue, is known relative to the robot by its particular design and manufacture, the position of the robot is known relative to the MR scanner coordinate system, since the robot is initially registered to the MR scanner, and each subsequent position also is known relative to the MR scanner coordinate system.

The robotic manipulator is a generic global positioner that can be easily adopted to carry and manipulate interventional or surgical implements of third party original equipment manufacturers OEM. As such it is not meant to compete with existing technologies, rather to be a tool that cooperates with them, such as by maneuvering the tool produced by an OEM. The robotic manipulator comprises an end-effector that has interchangeable interfaces suitable for attaching, carrying and manipulating virtually any currently used device or any device that may be produced in the future or any straight or bendable or steerable device. The robotic manipulator can be utilized with devices for procedures, such as, but not limited to, tissue cryo-ablation, thermal ablation by means of laser or radiofrequency, biopsy, including, but not limited to core, vacuum assisted or fine-needle aspiration FNA, multi-site FNA with the combination of a multi-sample holder, such as a rotating or linearly advancing carrousel, and/or local delivery of therapeutic or diagnostic agents.

Moreover, the robotic manipulator can be utilized in devices configured for scanning where the sensors are placed externally to the patient's body, such as for robot-mounted ultrasound. In this instance the robot is both the carrier and mechanical scanner of the robot-mounted sensors. The robot also is the mechanical link for co-registering the primary guidance modality, such as MRI, and the robot-mounted modality, such as US or optical, by means of an initial and/or intermittent registration of the robotic manipulator to the inherent coordinate system of the primary guidance modality. If such exists, and/or to an external means of spatial co-registration, such as optical tracking as is well-known in the art. The robotic manipulator also can be utilized in devices for scanning with sensors internally to the patient's body, such as robot-mounted US, optical imaging, optical spectroscopy, localized MRI, etc.

Furthermore, the robotic manipulator can carry surgical tools or other implements to perform single-port access surgical procedures. Multiple robotic manipulators may be combined, with each carrying complementary surgical or interventional tools, to perform multi-port access surgical procedures.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A flexible actuation transmission line for a medical-intervention robot, comprising:
    a channel containing solid media disposed inside that mechanically links a powering unit to an instrument or a component of the robot linked to the instrument;
    axial movement of said media inside the channel powered by the said powering unit actuates said instrument or actuated component; and
    gates which selectively block the channel.

2. The flexible actuation transmission line of claim 1 wherein the gates occlude the channel in whole or in part.

3. The flexible actuation transmission line of claim 1 wherein the gates automatically open when a specified inter-line pressure is exceeded.

4. The flexible actuation transmission line of claim 3 further including at least one connector to join different sections of said channel together, and wherein the gates are included as part of the connector.

5. The flexible actuation transmission line of claim 4 wherein the connector has two locking positions, such that at a first locking position, the gates cannot be closed, and at the second locking position, the gates can close.

6. The flexible actuation transmission line of claim 1 wherein the channel extends from the powering unit to said instrument or component.

7. The flexible actuation transmission line of claim 1 further including an opening in the channel other than at the ends of the various portions for the purpose of releasing said media from the channel.

8. The flexible actuation transmission line of claim 1 further including one or more ridges having a convex cross-section and longitudinally disposed on an inner wall thereof such that the ridges contact the media when the media are in the channel.

9. The flexible actuation transmission line of claim 1 further including openings in the line to equalize the pressure inside of the line with ambient pressure.

10. The flexible actuation transmission line of claim 1 further including one or more loaders for moving and packing the media axially inside the channel.

11. The flexible actuation transmission line of claim 10 wherein the loaders pack the media to a specified pressure.

12. The flexible actuation transmission line of claim 10 wherein the loaders are one or more pistons which each extend axially into an end of the channel.

13. The flexible actuation transmission line of claim 10 wherein the loaders are inside the channel and the channel includes an opening in its wall to access said loaders.

14. The flexible actuation transmission line of claim 10 wherein the loaders are powered by motors.

15. The flexible actuation transmission line of claim 1 further including a piston in a second channel which is advanced along the second channel by movement of the solid media in a first channel to thereby move the solid media in said second channel.

16. The flexible actuation transmission line of claim 15 wherein the piston includes stops which prevent its movement past particular points.

17. The flexible actuation transmission line of claim 15 further including a hydraulic system or a gear system which increases the force applied to media in the second portion to greater than the force applied to media in the first portion.

18. The flexible actuation transmission line of claim 15 wherein the media in said first portion moves in a direction substantially parallel to the media in said second portion.

19. The flexible actuation transmission line of claim 15 wherein the media in said first portion moves in a direction substantially opposite to the media in said second portion.

* * * * *